US008652788B2

(12) United States Patent
Adamczyk et al.

(10) Patent No.: US 8,652,788 B2
(45) Date of Patent: Feb. 18, 2014

(54) ASSAY FOR DIAGNOSIS OF CARDIAC MYOCYTE DAMAGE

(75) Inventors: Maciej Adamczyk, Gurnee, IL (US); Jefffrey R. Brashear, Mundelein, IL (US); Phillip G. Mattingly, Third Lake, IL (US)

(73) Assignee: Abbott Laboratories, Abbott Park, IL (US)

( * ) Notice: Subject to any disclaimer, the term of this patent is extended or adjusted under 35 U.S.C. 154(b) by 343 days.

(21) Appl. No.: 12/630,229

(22) Filed: Dec. 3, 2009

(65) Prior Publication Data

US 2011/0129854 A1    Jun. 2, 2011

Related U.S. Application Data

(63) Continuation-in-part of application No. 12/629,736, filed on Dec. 2, 2009.

(51) Int. Cl.
*G01N 33/53* (2006.01)
(52) U.S. Cl.
USPC .......................................... 435/7.1; 435/7.2
(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 5,006,309 A | 4/1991 | Khalil et al. | |
| 5,011,771 A * | 4/1991 | Bellet et al. | 435/7.94 |
| 5,063,081 A | 11/1991 | Cozzette et al. | |
| 5,089,424 A | 2/1992 | Khalil et al. | |
| 5,241,070 A | 8/1993 | Law | |
| 5,244,630 A | 9/1993 | Khalil et al. | |
| 5,434,087 A * | 7/1995 | Beggs et al. | 436/505 |
| 5,468,646 A | 11/1995 | Mattingly et al. | |
| 5,543,524 A | 8/1996 | Mattingly et al. | |
| 5,783,699 A | 7/1998 | Mattingly et al. | |
| 6,268,481 B1 * | 7/2001 | Morjana | 530/350 |
| 6,376,206 B1 | 4/2002 | Katus et al. | |
| 6,670,115 B1 | 12/2003 | Zhang | |
| 6,682,648 B1 | 1/2004 | MacPhee et al. | |
| 6,887,714 B2 | 5/2005 | Fritsch et al. | |
| 7,045,310 B2 | 5/2006 | Buck, Jr. et al. | |
| 7,045,364 B2 | 5/2006 | Limoges et al. | |
| 7,371,582 B2 * | 5/2008 | Nahm et al. | 436/514 |
| 7,776,605 B2 | 8/2010 | Mattingly et al. | |
| 2003/0170881 A1 | 9/2003 | Davis et al. | |
| 2004/0018577 A1 | 1/2004 | Emerson Campbell et al. | |
| 2005/0054078 A1 | 3/2005 | Miller et al. | |
| 2006/0160164 A1 | 7/2006 | Miller et al. | |
| 2008/0032929 A1 * | 2/2008 | Jin | 514/12 |
| 2009/0162876 A1 | 6/2009 | Adamczyk et al. | |
| 2010/0311079 A1 | 12/2010 | Mattingly et al. | |
| 2011/0085976 A1 * | 4/2011 | Yan et al. | 424/9.1 |

FOREIGN PATENT DOCUMENTS

| | | |
|---|---|---|
| CN | 2783324 Y | 5/2006 |
| EP | 425633 B1 | 7/1994 |
| EP | 273115 B1 | 9/1994 |
| EP | 424634 B1 | 6/1995 |
| EP | 406473 B1 | 9/1995 |
| EP | 326100 B1 | 9/1996 |
| EP | 1890154 A1 | 2/2008 |
| WO | WO2007138163 A2 | 12/2007 |

OTHER PUBLICATIONS

Henares T.G., et al., "Current Development in Microfluidic Immunosensing Chip," Analytica Chimica Acta, 2008, vol. 611 (1), pp. 17-30.
International Search Report and Written Opinion for Application No. PCT/US2010/056992, mailed on Jan. 31, 2011, 11 pages.
Marquette C.A., et al., "Disposable Screen-Printed Chemiluminescent Biochips for the Simultaneous Determination of Four Point-of-Care Relevant Proteins," Analytical and Bioanalytical Chemistry, 2009, vol. 393 (4), pp. 191-198.
Adamczyk et al., "Linker-Medicated Modulation of the Cheiluminescent Signal From N10-(3-Sulfopropyl)-N-Sulfonylacridinium-9-carboxamide Tracers," Bioconjugate Chem, 2000, pp. 714-724, vol. 11.
Adamczyk et al., "Modulation of the Chemiluminescent Signal From N10-(3-Sulfopropyl)-N-Sulfonylacridinium-9-carboxamides," Tetrahedron, 1999, pp. 10899-10914, vol. 55.
Adamczyk et al., "Neopentyl 3-Triflyloxypropanesulfaonate Areactive Sulfopropylation Reagent for the Preparation of Chemiluminescent Labels," J Org Chem, 1998, pp. 5636-5639, vol. 63.
Adamczyk et al., "Regiodependent Luminescence Quenching of Biotinylated N-Sulfonyl-acridinium-9-carboxamides by Avidin," Organic Letters, 2003, pp. 3779-3782, vol. 5 (21).
Adamczyk et al., "Synthesis of a Chemiluminescent Acridinium Hydroxylamine (AHA) for the Direct Detection of Abasic Sites in DNA," Organic Letters, 1999, pp. 779-781, vol. 1 (5).
Akerstrom et al., "Protein G: A Powerful Tool for Binding and Detection of Monoclonal and Polyclonal Antibodies'," Immunology, 1985, vol. 135 (4) pp. 2589-2592.
Amgad N. Makaryus, "Falsely Elevated Cardiac Troponin I Levels" Clin. Cardiol. 30, 92-94, 2007.
Clackson T., et al., "Making antibody fragments using phage display libraries," Nature,, 1991, 352, 624-628.
Coligan, A., Current Protocols in Protein Science, TOC, U.S. Appl. No. 12/443,492, filed Oct. 12, 2007.
Co-pending U.S. Appl. No. 06/921,979, filed 1986.
Co-pending U.S. Appl. No. 07/150,278, filed 1988.
Co-pending U.S. Appl. No. 07/375,029, filed 1988.
Daniel P. Stites, et al, "Basic and Clinical Immunology" LANGE medical book, 1991.
David J. Asai, et al, "Methods in Cell Biology" Antibodies in Cell Biology, vol. 37, 1993.
Goran Kronvall, et al, "A Surface Component in Group A, C, and G Streptococci With Non-Immune Reactivity for Immunoglobulin G" Boilinology, vol. 111 (5), 1973.

(Continued)

*Primary Examiner* — Jacob Cheu
(74) *Attorney, Agent, or Firm* — Cheryl L. Becker

(57) ABSTRACT

Assays are disclosed for diagnosing a clinical condition, assessing risk or predicting an outcome as a result of cardiac myocyte damage. Immunoassay methods and kits provide for the assessment of cardiac myocyte damage by determining the presence of multiple cardiac myocyte antigens in a test sample, and combining the multiple determinations in a single assay result.

12 Claims, 8 Drawing Sheets

(56) References Cited

OTHER PUBLICATIONS

Griffiths A. D., et al., "Human anti-self antibodies with high specificity from phage display libraries," The EMBO J, 1993, 12 (2), 725-734.

Hoogenboom H. R., et al., Multi-subunit proteins on the surface of filamentous phage: methodologies for displaying antibody (Fab) heavy and light chains, Nucleic Acids Research, 1991, 19 (15), Oxford University Press, 4133-4137.

Kenny, et al., Falsely elevated cardiac troponin-I in patients with seropositive rheumatoid arthritis, Journal of Rheumatology, 2005, vol. 32, pp. 1258-1260.

Knoblcok., et al., Arch Pathol Lab Med, 2002, 126, 606-609.

Kohler G., et al., "Continuous cultures of fused cells secreting antibody of predefined specificity," Nature, 1975, 256 (5517), 495-497.

Langone, et al, "Production of Antisera with Small Doses of Immunogen: Multiple Intradermal Injections", MethodsEnzymology, vol. 73, 46-52, 1981.

Marks J. D. et al., "By-passing immunization. Human antibodies from V-gene libraries displayed on phage," J Mol Biol, 1991, vol. 222, pp. 581-597.

Marks, J.D. et al. (1992). "By-Passing Immunization: Building High Affinity Human Antibodies by Chain Shuffling," Bio/Technol. 10:779:783.

Mattingly et al., "Chemiluminescent N-Sulfonylacridinium-9-Carboxamides and Their Application in Clinical Assays," Luminescence Biotechnology: Instruments and Applications (CRC Press: Boca Raton 2000), 2002, pp. 77-105.

Mattingly Phillip G., "Chemiluminescent 10-Methyl-Acridinium-9(N-Sulphonylcarboxamide) Salts. Synthesis and Kinetics of Light Emission," Journal of Bioluminescence and Chemiluminescence, 1991, pp. 107-114, vol. 6.

Mccafferty J., et al., "Phage antibodies: filamentous phage displaying antibody variable domains," Nature, 1990, 348, 552-554.

McCapra, et al., "Chemiluminescence Involving Peroxide Decompositions", Photochemistry and Photobiology, 1965, 4, 1111-1121.

Razavi, "Stable and versatile active acridinium esters I," Luminescence, 2000, pp. 239-244, vol. 15.

Razavi, "Stable and versatile active acridinium esters II," Luminescence, 2000, pp. 245-249, vol. 15.

Adamczyk M., et al., "Prevalence of Autoantibodies to Cardiac Troponin T Healthy Blood Donors," Clinical Chemistry, 2009, vol. 55 (8), pp. 1592-1593.

Cobbaert C., et al., "Do NIST SRM 2921 and Recombinant cTnI-based Serum Pools have Potential to Harmonize cTnI Results", Nederlands Tijdschrift Klinische Chemie LabGeneeskunde, 2007, vol. 32, pp. 175-178.

International Search Report and Written opinion for Application No. PCT/US2010/057004, mailed on Feb. 7, 2011, 11 pages.

Mahalingam M., et al., "False-Negative Qualitative Cardiac Troponin T in a 79-Year-Old Man With Myocardial Infarction," Journal of the American Medical Association, 1997, vol. 278 (24), pp. 2143-2144.

Murthy V.V., et al., "Troponin-T as a Serum Marker for Myocardial Infarction," Journal of Clinical Laboratory Analysis, 1997, vol. 11 (3), pp. 125-128.

O'Brien P.J., et al., "Cardiac Troponin I is a Sensitive, Specific Biomarker of Cardiac Injury in Laboratory Animals," Laboratory Animals, 2006, vol. 40 (2), pp. 153-171.

Scott B., et al., "Cardiac Troponin T and Malondialdehyde Modified Plasma Lipids in Haemodialysis Patients," Nephrology Dialysis Transplantation, 2003, vol. 18 (4), pp. 737-742.

Shayanfar N., et al., "False-Positive Cardiac Troponin T Due to Assay Interference with Heterophilic Antibodies," Swiss Medical Weekly, 2008, vol. 138, pp. 31-32.

Sodi R., et al., "Time for Troponin T? Implications from Newly Elucidated Structure," Clinical Chemistry, 2004, vol. 50 (4), pp. 786-787.

White G.H., et al., "Heterophilic Antibody Interference with CARDIAC T Quantitative Rapid Assay," Clinical Chemistry, 2002, vol. 48 (1), pp. 201-202.

\* cited by examiner

SDIEEVVEEY.EEEEQEEAAV EEEEDWREDE DEQEEAAEED AEAEAETEET
RAEEDEEEEE AKEAEDGPME ESKPKPRSFM PNLVPPKIPD GERVDFDDIH
RKRMEKDLNE LQALIEAHFE NRKKEEEELV SLKDRIERRR AERAEQQRIR
NEREKERQNR LAEERARREE EENRRKAEDE ARKKKALSNM MHFGGYIQKQ
AQTERKSGKR QTEREKKKKI LAERRKVLAI DHLNEDQLRE KAKELWQSIY
NLEAEKFDLQ EKFKQQKYEI NVLRNRINDN QKVSKTRGKA KVTGRWK (297 aa)

FIG. 2

ADGSSDAARE PRPAPAPIRR RSSNYRAYAT EPHAKKKSKI SASRKLQLKT
LLLQIAKQEL EREAEERRGE KGRALSTRCQ PLELAGLGFA ELQDLCRQLH
ARVDKVDEER YDIEAKVTKN ITEIADLTQK IFDLRGKFKR PTLRRVRISA
DAMMQALLGA RAKESLDLRA HLKQVKKEDT EKENREVGDW RKNIDALSGM
EGRKKKFES (209 aa)

FIG. 6

ASSAY FOR DIAGNOSIS OF CARDIAC MYOCYTE DAMAGE

RELATED APPLICATION INFORMATION

This application is a continuation-in-part application of U.S. application Ser. No. 12/629,736, filed Dec. 2, 2009.

INCORPORATION OF SEQUENCE LISTING

The entire contents of a paper copy of the "Sequence Listing" and a computer readable form of the sequence listing on diskette, containing the file named 404361_SequenceListing_ST25.txt, which is 36 kilobytes in size and was created on Feb. 9, 2010, are herein incorporated by reference.

TECHNICAL FIELD

The present disclosure relates generally to assays and kits for diagnosing cardiac myocyte damage in a subject, and in particular to methods and kits for detecting the presence of multiple cardiac myocyte antigens in a test sample, which also avoids the potential for interference from the presence of other substances in the test sample.

BACKGROUND OF THE INVENTION

Immunoassay techniques have been known for the last few decades and are now commonly used in medicine for a wide variety of diagnostic purposes to detect target analytes in a biological sample. Immunoassays exploit the highly specific binding of an antibody to its corresponding antigen, wherein the antigen is the target analyte. Typically, quantification of either the antibody or antigen is achieved through some form of labeling such as radio- or fluorescence-labeling. Sandwich immunoassays involve binding the target analyte in the sample to the antibody site (which is frequently bound to a solid support), binding labeled antibody to the captured analyte, and then measuring the amount of bound labeled antibody, wherein the label generates a signal proportional to the concentration of the target analyte inasmuch as labeled antibody does not bind unless the analyte is present in the sample.

Among the currently available assays for diagnosing a clinical condition, assessing risk or predicting an outcome resulting from cardiac myocyte damage are those determining the concentration of cardiac troponin-I, cardiac troponin-T, creatine phosphokinase MB (CKMB), myoglobin, myosin heavy chain, myosin light chain, B-type natriuretic peptide (including pro-BNP, NT-proBNP, and hBNP(1-32)), heart fatty-acid-binding protein (H-FABP), placenta growth factor (PLGF), and/or interleukin-6 (IL-6). Typically, such assays are conducted as a panel of immunoassays that are performed sequentially on a test sample from a patient and testing for each analyte thus requires additional increments of time, volume of sample and reagents for each assay result. Frequently, assays for the complete panel of analytes are not available on a single assay platform, from a single vendor, or even by a single detection technology, which adds to the complexity of assessing the clinical status of the patient. Further, when conducted separately and in series, the result for any single analyte in the panel may be unreliable, i.e. may or may not be erroneous. Which if any of the individual assay results are erroneous may be difficult or impractical to determine, thus leading to potentially conflicting results and correspondingly conflicting diagnosis, assessment of risk or prediction of outcome.

The example of two related antigens, cardiac troponin-T and cardiac troponin-I is illustrative. Cardiac troponin-I assays are readily commercially available from multiple vendors, but cardiac troponin-T assays are restricted to a single vendor, Roche Diagnostics, which means that no alternatives are available. Additionally, both assays are limited in terms of accuracy according to multiple reports of false-positive and false negative results. (See, e.g, P. R. Kenny et al., J. 32 Rheumatol, 1258-61, (2005); R. I. Knoblock et al., Archives of pathology & laboratory medicine 2002; 126:606-9; and A. N. Makaryus et al., Clin Cardiol 2007; 30:92-4). Moreover, while both cardiac troponin-I and cardiac troponin-T in theory are associated with cardiac myocyte damage, immunoassays for the determination of cardiac troponin-I and cardiac troponin-T in patient samples fail to correlate about 10% of the time. This discrepancy may be due to differences in antibody configurations, other biochemical differences or analytical among the different assays.

Further, such immunoassays for circulating antigens are known for being susceptible to interference from other substances that may be present in a test sample, such as heterophilic endogenous antibodies, and autoantibodies. Such interference is typically addressed by performing a second assay to identify problematic samples, which is time-consuming and costly. Another approach to addressing the autoantibody problem is to choose analyte-specific antibodies that bind to specific epitopes distinct from the analyte epitopes that react with the autoantibodies. Following this general approach, efforts have focused on exploring the use of thousands of different combinations of two, three and even four analyte-specific antibodies to avoid interference from autoantibodies. However, this effort has been largely unsuccessful. It is now evident that autoantibodies against complex protein analytes are likely to be polyclonal within a particular sample, and may be even more diverse among samples from different individuals. Interference from diverse polyclonal autoantibodies may explain the observation that as little as 25% or even less of an analyte protein sequence binds to analyte-specific antibodies, which may in turn explain the lack of success using this approach.

Thus, at least for the aforementioned reasons, initial tests of either cardiac troponin-I or cardiac troponin-T alone and using standard assays may be negative despite the occurrence of MI, i.e. may provide false negative results. While the available assays for cardiac troponin-I or cardiac troponin-T have improved the timeliness of diagnosis of MI, nevertheless many patients with MI symptoms are not positively diagnosed until several hours after presentation. This results in delayed or postponed treatment with potentially serious results.

A need exists in the art for new immunoassay methods that improve detection of cardiac myocyte damage including the timeliness of such detection, and also for methods that compensate for interference by heterophilic endogenous antibodies and autoantibodies that may be present in a test sample, and in particular, for such methods that achieve these results without redesign of the analyte detection or capture antibodies.

SUMMARY OF THE INVENTION

In one aspect, the present disclosure provides an immunoassay for detecting cardiac myocyte damage in a subject from a test sample, the immunoassay comprising the steps of:
a) contacting a test sample from a subject suspected of having cardiac myocyte damage with n antibodies ($A_{a^n}$) that bind to at least n epitopes on n' cardiac myocyte antigens ($a^{n'}$) to form n' (n-antibody:antigen) immuno-complexes $(A_{a_1^1})(A_{a_1^2})\ldots(A_{a_1^n})(a^1)$, $(A_{a_2^1})(A_{a_2^2})\ldots(A_{a_2^n})(a^2)$, $\ldots(A_{a_{n'}^1})(A_{a_{n'}^2})\ldots(A_{a_{n'}^n})(a^{n'})$ wherein n is an integer from 1 to 10; and n' is an integer from 2 to 10.

b) contacting said mixture comprising n' (n-antibody:antigen) immuno-complexes with n" antibodies ($B_{a_n^{n''}}$) that bind to n" epitopes on n' cardiac myocyte antigens ($a^{n'}$) to form n' ((n+n") antibody:antigen) measurable assemblies $((A_{a_1^1})(A_{a_1^2})\ldots(A_{a_1^n}))((B_{a_1^1})(B_{a_1^2})\ldots(B_{a_1^{n''}}))(a^1)$, $((A_{a_2^1})(A_{a_2^2})\ldots(A_{a_2^n}))((B_{a_2^1})(B_{a_2^2})\ldots(B_{a_2^{n''}}))(a^2)$, $\ldots((A_{a_{n'}^1})(A_{a_{n'}^2})\ldots(A_{a_{n'}^n}))((B_{a_{n'}^1})(B_{a_{n'}^2})\ldots(B_{a_{n'}^{n''}}))(a^{n'})$ wherein n and n" are independently an integer from 1 to 10, and n' is an integer from 2 to 10, and antibodies A and B bind to (n+n") different epitopes of a cardiac myocyte antigen.

c) measuring an optical, electrical, or change-of-state signal of the measurable assembly; and d) detecting cardiac myocyte damage by determining whether the measurement in step (c) exceeds a predetermined level.

The cardiac myocyte antigens (a') can be selected from the group consisting of cardiac troponin-I, cardiac troponin-T, creatine phosphokinase MB (CKMB), myoglobin, myosin heavy chain, myosin light chain, B-type natriuretic peptide (including pro-BNP, NT-proBNP, and hBNP(1-32)), heart fatty-acid-binding protein (H-FABP), placenta growth factor (PLGF), and interleukin-6 (IL-6). In an exemplary embodiment of the immunoassay, n'=2 and the cardiac myocyte antigens ($a^{n'}$) are for example cardiac troponin-I (cTnI) and cardiac troponin-T (cTnT)). The antibodies $A_{a_n^{n'}}$, antibodies $B_{a_n^{n''}}$, or antibodies $A_{a_n^{n'}}$ and $B_{a_n^{n''}}$ can comprise humanized antibodies.

In the above immunoassay, the antibodies $B_{a_n^{n''}}$ can be bound through covalent or non-covalent bonds to a detectable label, such as an enzyme, oligonucleotide, nanoparticle chemiluminophore, fluorophore, fluorescence quencher, chemiluminescence quencher, or biotin. The optical signal can be measured as an antigens ($a^{n'}$) concentration dependent change in chemiluminescence, fluorescence, phosphorescence, electrochemiluminescence, ultraviolet absorption, visible absorption, infrared absorption, refraction, surface plasmon resonance. The electrical signal can be measured as an antigens ($a^{n'}$) concentration dependent change in current, resistance, potential, mass to charge ratio, or ion count. The change-of-state signal can be measured as an antigens ($a^{n'}$) concentration dependent change in size, solubility, mass, or resonance.

In the above immunoassay, antibodies $B_{a_n^{n''}}$ may comprise humanized antibodies complexed with an anti-human IgG antibody, said anti-human IgG antibody being conjugated to a detectable label, wherein the detectable label is an enzyme, oligonucleotide, nanoparticle chemiluminophore, fluorophore, fluorescence quencher, chemiluminescence quencher, or biotin.

In the above immunoassay, the antibodies $A_{a_n^{n'}}$ can be immobilized on a solid phase. The solid phase can be selected from the group consisting of a magnetic particle, bead, test tube, microtiter plate, cuvette, membrane, a scaffolding molecule, quartz crystal, film, filter paper, disc and chip.

In another aspect, the present disclosure provides an immunoassay for detecting cardiac myocyte damage in a subject from a test sample, the immunoassay comprising the steps of:

a) contacting a test sample from a subject suspected of having cardiac myocyte damage with n antibodies ($A_{a_n^{n'}}$) that bind to at least n epitopes on n' cardiac myocyte antigens ($a^{n'}$) to form n' (n-antibody:antigen) immuno-complexes $(A_{a_1^1})(A_{a_1^2})\ldots(A_{a_1^n})(a^1)$, $(A_{a_2^1})(A_{a_2^2})\ldots(A_{a_2^n})(a^2)$, $\ldots(A_{a_{n'}^1})(A_{a_{n'}^2})\ldots(A_{a_{n'}^n})(a^{n'})$ wherein n is an integer from 1 to 10; and n' is an integer from 2 to 10.

b) contacting said mixture comprising n' (n-antibody:antigen) immuno-complexes with n" antibodies ($B_{a_n^{n''}}$) that bind to n" epitopes on n' cardiac myocyte antigens ($a^{n'}$) to form n' ((n+n") antibody:antigen) measurable assemblies $((A_{a_1^1})(A_{a_1^2})\ldots(A_{a_1^n}))((B_{a_1^1})(B_{a_1^2})\ldots(B_{a_1^{n''}}))(a^1)$, $((A_{a_2^1})(A_{a_2^2})\ldots(A_{a_2^n}))((B_{a_2^1})(B_{a_2^2})\ldots(B_{a_2^{n''}}))(a^2)$, $\ldots((A_{a_{n'}^1})(A_{a_{n'}^2})\ldots(A_{a_{n'}^n}))((B_{a_{n'}^1})(B_{a_{n'}^2})\ldots(B_{a_{n'}^{n''}}))(a^{n'})$ wherein n and n" are independently an integer from 1 to 10, and n' is an integer from 2 to 10, and antibodies $A_{a_n^{n'}}$ and $B_{a_n^{n''}}$ bind to (n+n") different epitopes of a cardiac myocyte antigen, wherein antibodies $B_{a_n^{n''}}$ are labeled with a detectable label comprising at least one acridinium compound;

c) generating or providing a source of hydrogen peroxide to the mixture of step (b);

d) adding a basic solution to the mixture of step (c) to generate a light signal;

e) measuring the light signal generated by or emitted in step (d); and f) detecting cardiac myocyte damage by determining whether the measurement in step (e) exceeds a predetermined level.

In the above immunoassay, the cardiac myocyte antigens ($a^{n'}$) can be selected from the group consisting of cardiac troponin-I, cardiac troponin-T, creatine phosphokinase MB (CKMB), myoglobin, myosin heavy chain, myosin light chain, B-type natriuretic peptide (including pro-BNP, NT-proBNP, and hBNP(1-32)), heart fatty-acid-binding protein (H-FABP), placenta growth factor (PLGF), and interleukin-6 (IL-6). In an exemplary embodiment of the immunoassay, n'=2 and the cardiac myocyte antigens ($a^{n'}$) are cardiac troponin-I (cTnI) and cardiac troponin-T (cTnT). The antibodies $A_{a_n^{n'}}$, antibodies $B_{a_n^{n''}}$, or antibodies $A_{a_n^{n'}}$ and $B_{a_n^{n''}}$ can comprise humanized antibodies.

In the above immunoassay, the antibodies $B_{a_n^{n''}}$ can be bound through covalent or non-covalent bonds to a detectable label, such as an enzyme, oligonucleotide, nanoparticle chemiluminophore, fluorophore, fluorescence quencher, chemiluminescence quencher, or biotin. The optical signal can be measured as an antigens ($a^{n'}$) concentration dependent change in chemiluminescence, fluorescence, phosphorescence, electrochemiluminescence, ultraviolet absorption, visible absorption, infrared absorption, refraction, surface plasmon resonance. The electrical signal can be measured as an antigens ($a^{n'}$) concentration dependent change in current, resistance, potential, mass to charge ratio, or ion count. The change-of-state signal can be measured as an antigens ($a^{n'}$) concentration dependent change in size, solubility, mass, or resonance.

In the above immunoassay, antibodies $B_{a_n^{n''}}$ my comprise humanized antibodies complexed with an anti-human IgG antibody, said anti-human IgG antibody being conjugated to a detectable label, wherein the detectable label is an enzyme, oligonucleotide, nanoparticle chemiluminophore, fluorophore, fluorescence quencher, chemiluminescence quencher, or biotin.

In the above immunoassay, the antibodies $A_{a_n^{n'}}$ can be immobilized on a solid phase. The solid phase can be selected from the group consisting of a magnetic particle, bead, test tube, microtiter plate, cuvette, membrane, a scaffolding molecule, quartz crystal, film, filter paper, disc and chip.

In the above immunoassay, the acridinium compound can be an acridinium-9-carboxamide having a structure according to formula I:

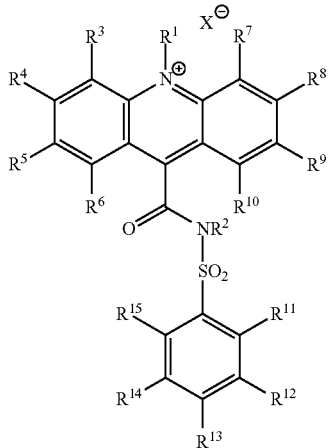

I wherein R1 and R2 are each independently selected from the group consisting of: alkyl, alkenyl, alkynyl, aryl or aralkyl, sulfoalkyl, carboxyalkyl and oxoalkyl, and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\ominus}$ is an anion.

Alternatively, in the above immunoassay the acridinium compound can be an acridinium-9-carboxylate aryl ester having a structure according to formula II:

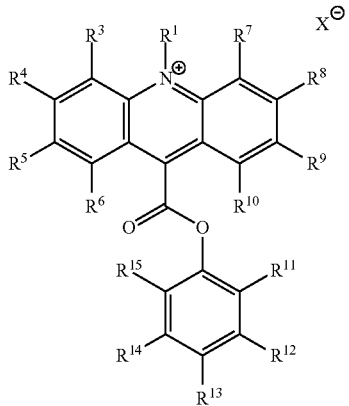

II wherein R1 is an alkyl, alkenyl, alkynyl, aryl or aralkyl, sulfoalkyl, carboxyalkyl and oxoalkyl; and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\ominus}$ is an anion.

In the above immunoassay, the antibodies $A_{a''}{}^{n}$ can be selected from the group consisting of a polyclonal antibody, a monoclonal antibody, a chimeric antibody, a human antibody, and an affinity maturated antibody. The antibodies $B_{a''}{}^{n'''}$ can be selected from the group consisting of a polyclonal antibody, a monoclonal antibody, a chimeric antibody, a human antibody, and an affinity maturated antibody.

In the above immunoassay, the hydrogen peroxide can be provided by adding a buffer or a solution containing hydrogen peroxide. The hydrogen peroxide can be generated for example by adding a hydrogen peroxide generating enzyme to the test sample. The hydrogen peroxide generating enzyme can be selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

In the above immunoassay, the basic solution can be for example a solution having a pH of at least about 10.

In the above immunoassay, the step f) of detecting cardiac myocyte damage by determining whether the measurement in step (e) exceeds a predetermined level comprises relating the amount of light signal in step (e) to the amount of cardiac myocyte antigens $a^{n'}$ in the test sample either by use of a standard curve for each cardiac myocyte antigen $a^{n'}$ or by comparison to a reference standard for each cardiac myocyte antigen $a^{n'}$. The reference standard for each cardiac myocyte antigen $a^{n'}$ can comprise an anti-idiotypic antibody. The reference standard can comprise a derivatized cardiac myocyte antigen, such as a cardiac myocyte antigen derivatized with a polyethylene glycol.

Any of the above immunoassays can be adapted for use in an automated system or semi-automated system.

In any of the above immunoassays, the test sample can be whole blood, serum, or plasma.

In another aspect, the present disclosure provides a kit for detecting cardiac myocyte damage from a test sample, the kit comprising: n antibodies ($A_{a_n''}$) that bind to at least n epitopes on n' cardiac myocyte antigens ($a^{n'}$) to form n' (n-antibody: antigen) immuno-complexes $(A_{a_1}^1)(A_{a_1}^2) \ldots (A_{a_1}^{n''})(a^1)$, $(A_{a_2}^1)(A_{a_2}^2) \ldots (A_{a_2}^{n''})(a^2), \ldots (A_{a_{n'}}^1)(A_{a_{n'}}^2) \ldots (A_{a_{n'}}^{n''})(a^{n'})$ wherein n is an integer from 1 to 10; and n' is an integer from 2 to 10; and n" antibodies ($B_{a_{n'}''}$) that bind to n" epitopes on n' cardiac myocyte antigens ($a^{n'}$) to form n' ((n+n") antibody: antigen) measurable assemblies $((A_{a_1}^1)(A_{a_1}^2) \ldots (A_{a_1}^{n''})$ $((B_{a_1}^1)(B_{a_1}^2) \ldots (B_{a_1}^{n''})(a^1), ((A_{a_2}^1)(A_{a_2}^2) \ldots (A_{a_2}^{n''})((B_{a_2}^1)$ $(B_{a_2}^2) \ldots (B_{a_2}^{n''})(a^2), \ldots ((A_{a_{n'}}^1)(A_{a_{n'}}^2) \ldots (A_{a_{n'}}^{n''})(B_{a_{n'}}^{n''})$ $(B_{a_{n'}}^2) \ldots (B_{a_{n'}}^{n''}))(a^{n'})$, wherein n and n" are independently an integer from 1 to 10, and n' is an integer from 2 to 10, and antibodies A and B bind to (n+n") different epitopes of a cardiac myocyte antigen, and instructions for determining whether the total amount of cardiac antigens ($a^{n'}$) in the test sample exceeds a predetermined level. In the kit, the cardiac myocyte antigens ($a^{n'}$) can be selected from the group consisting of cardiac troponin-I, cardiac troponin-T, creatine phosphokinase MB (CKMB), myoglobin, myosin heavy chain, myosin light chain, B-type natriuretic peptide, wherein the first cardiac specific antigen and the second cardiac specific antigen are different antigens. In an exemplary embodiment of the kit, n'=2 and the cardiac myocyte antigens ($a^{n'}$) are cardiac troponin-I (cTnI) and cardiac troponin-T (cTnT).

The above kit may further comprise a solid phase wherein the antibodies $A_{a_{n''}}$ are bound to the solid phase. The solid phase can be selected from the group consisting of a magnetic particle, a bead, a test tube, a microtiter plate, a cuvette, a membrane, a scaffolding molecule, a quartz crystal, a film, a filter paper, a disc and a chip.

The above kit may further comprise a detectable label, to which the antibodies $B_{a_{n''}}$ are bound through covalent or non-covalent bonds. The detectable label can be an enzyme, oligonucleotide, nanoparticle chemiluminophore, fluorophore, fluorescence quencher, chemiluminescence quencher, or biotin.

In certain embodiments of the kit, the detectable label can be an acridinium compound. The acridinium compound can be an acridinium-9-carboxamide having a structure according to formula I:

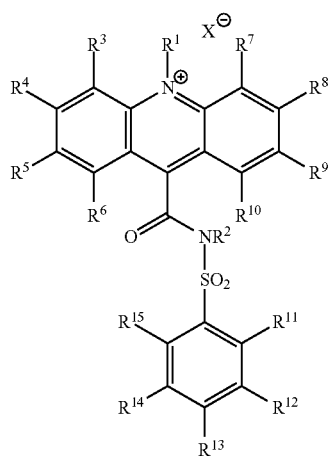

I wherein R1 and R2 are each independently selected from the group consisting of: alkyl, alkenyl, alkynyl, aryl or aralkyl, sulfoalkyl, carboxyalkyl and oxoalkyl, and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

Alternatively, in the above kit the acridinium compound can be an acridinium-9-carboxylate aryl ester having a structure according to formula II:

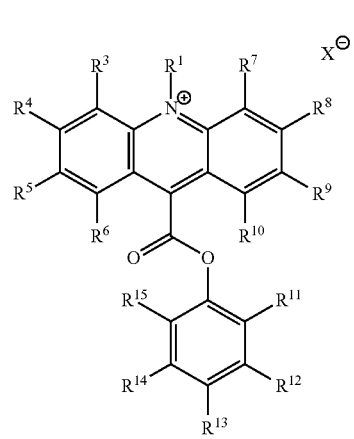

II wherein R1 is an alkyl, alkenyl, alkynyl, aryl or aralkyl, sulfoalkyl, carboxyalkyl and oxoalkyl; and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

The kit may further comprise a basic solution, such as for example a solution having a pH of at least about 10. The kit may further comprise a hydrogen peroxide source. The hydrogen peroxide source can comprise a buffer or a solution containing hydrogen peroxide. The hydrogen peroxide source can comprise a hydrogen peroxide generating enzyme. The hydrogen peroxide generating enzyme can be selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD (P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

In the above kit, the antibodies $A_{a^n}{}^n$, antibodies $B_{a^n}{}^{n'''}$, or antibodies $A_{a^n}{}^n$ and $B_{a^n}{}^{n'''}$ can comprise humanized antibodies. In an exemplary embodiment of the kit, the antibodies $B_{a^n}{}^{n'''}$ comprise anti-human IgG antibodies.

The above kit may further comprise one or more cardiac antigen reference standards. Each cardiac antigen reference standard can comprise an anti-idiotypic antibody. Each cardiac antigen reference standard can comprise a derivatized cardiac antigen, such as the cardiac antigen derivatized with a polyethylene glycol.

BRIEF DESCRIPTION OF THE DRAWINGS

FIG. 2 is the amino acid sequence of Human cardiac troponin-T (cTnT);

FIG. 6 is the amino acid sequence of Human cardiac troponin-I (cTnI);

DETAILED DESCRIPTION

Figure 1:
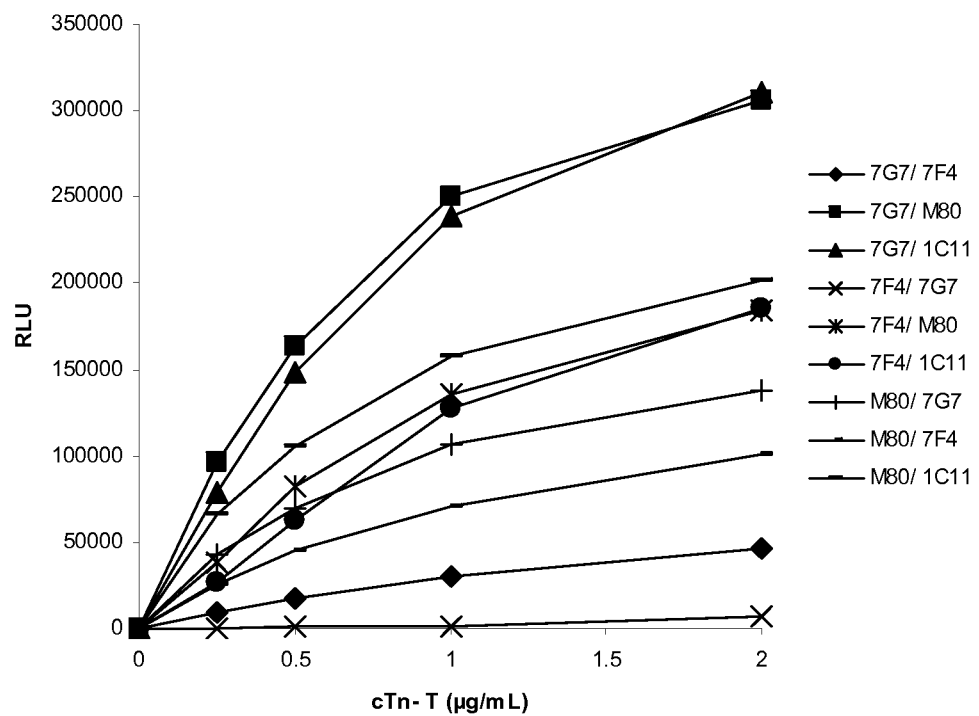
FIG. 1 is a graph of dose-response of different combinations of detection and capture antibodies.

The present disclosure provides an improved assay for detecting cardiac myocyte damage in a subject from a test sample. The assays are useful for diagnosing a clinical condition, assessing risk or predicting an outcome related to cardiac myocyte damage. According to the disclosed immunoassay methods and kits, cardiac myocyte damage can be diagnosed even to the extent of cardiac myocyte death. Additionally, the immunoassay methods and kits are especially useful for detecting cardiac myocyte damage based on a test sample from a subject wherein the test sample may also contain other substances that may interfere with the determination of cardiac damage indicators, particularly where such a determination is reported as a single assay result. In contrast, the methods and kits as disclosed herein provide a new approach to enhancing assays of cardiac myocyte damage, by combining results from at least two different indicators of cardiac myocyte damage and reporting the signal as a single result, wherein the indicators are cardiac myocyte antigens.

The results from determinations of the different cardiac myocyte antigens can be performed in sequence or in parallel.

Thus, the present disclosure provides methods and kits for increased analytical and clinical sensitivity over methods based on a single indicator of cardiac myocyte damage, such as those that rely on determinations of cardiac troponin-I (cTnI) alone, or of cardiac troponin-T (cTnT) alone. Accordingly, the presently disclosed methods and kits provide for a more reliable diagnosis of MI, risk stratification, and prognosis. The methods and kits are useful in the diagnosis and care of patients suffering from cardiac pathologies such as congestive heart failure, acute coronary syndrome, myocardial infarction, myocarditis, and the like, and also renal disease, kidney injury and the like.

The methods are based in part on the use of more than one capture phase antibody and more than one detection antibody to improve specificity. This assay approach also compensates for the presence of other substances such as heterophilic endogenous antibodies, and autoantibodies that may be present in the test sample, without redesign of the analyte-specific detection antibodies or the capture antibodies, and avoids the need of a second assay to identify problematic samples. Additionally, the methods provide for the use of humanized immunoreagents to overcome heterophilic antibody interferences. Use of antihuman IgG detection antibody corrects for endogeneous autoantibodies and when used in conjunction with humanized immunoreagents provides a "universal" signal generator. Derivatized cardiac myocyte antigens are also described as reference standards suitable for assay standardization.

A. Definitions

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Acyl (and Other Chemical Structural Group Definitions)

As used herein, the term "acyl" refers to a —C(O)R$_a$ group where R$_a$ is hydrogen, alkyl, cycloalkyl, cycloalkylalkyl, phenyl or phenylalkyl. Representative examples of acyl include, but are not limited to, formyl, acetyl, cylcohexylcarbonyl, cyclohexylmethylcarbonyl, benzoyl, benzylcarbonyl and the like.

As used herein, the term "alkenyl" means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

As used herein, the term "alkyl radical" means any of a series of univalent groups of the general formula $C_nH_{2n+1}$ derived from straight or branched chain hydrocarbons.

As used herein, the term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkynyl" means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

As used herein, the term "amido" refers to an amino group attached to the parent molecular moiety through a carbonyl group (wherein the term "carbonyl group" refers to a —C(O)— group).

As used herein, the term "amino" means —$NR_bR_c$, wherein $R_b$ and $R_c$ are independently selected from the group consisting of hydrogen, alkyl and alkylcarbonyl.

As used herein, the term "aralkyl" means an aryl group appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

As used herein, the term "aryl" means a phenyl group, or a bicyclic or tricyclic fused ring system wherein one or more of the fused rings is a phenyl group. Bicyclic fused ring systems are exemplified by a phenyl group fused to a cycloalkenyl group, a cycloalkyl group, or another phenyl group. Tricyclic fused ring systems are exemplified by a bicyclic fused ring system fused to a cycloalkenyl group, a cycloalkyl group, as defined herein or another phenyl group. Representative examples of aryl include, but are not limited to, anthracenyl, azulenyl, fluorenyl, indanyl, indenyl, naphthyl, phenyl, and tetrahydronaphthyl. The aryl groups of the present disclosure can be optionally substituted with one-, two, three, four, or five substituents independently selected from the group consisting of alkoxy, alkyl, carboxyl, halo, and hydroxyl.

As used herein, the term "carboxy" or "carboxyl" refers to —$CO_2H$ or —$CO_2^-$.

As used herein, the term "carboxyalkyl" refers to a —$(CH_2)$—$CO_2H$ or —$(CH_2)$—$CO_2^-$ group where n is from 1 to 10.

As used herein, the term "cyano" means a —CN group.

As used herein, the term "cycloalkenyl" refers to a non-aromatic cyclic or bicyclic ring system having from three to ten carbon atoms and one to three rings, wherein each five-membered ring has one double bond, each six-membered ring has one or two double bonds, each seven- and eight-membered ring has one to three double bonds, and each nine- to ten-membered ring has one to four double bonds. Representative examples of cycloalkenyl groups include cyclohexenyl, octahydronaphthalenyl, norbornylenyl, and the like. The cycloalkenyl groups can be optionally substituted with one, two, three, four, or five substituents independently selected from the group consisting of alkoxy, alkyl, carboxyl, halo, and hydroxyl.

As used herein, the term "cycloalkyl" refers to a saturated monocyclic, bicyclic, or tricyclic hydrocarbon ring system having three to twelve carbon atoms. Representative examples of cycloalkyl groups include cyclopropyl, cyclopentyl, bicyclo[3.1.1]heptyl, adamantyl, and the like. The cycloalkyl groups of the present disclosure can be optionally substituted with one, two, three, four, or five substituents independently selected from the group consisting of alkoxy, alkyl, carboxyl, halo, and hydroxyl.

As used herein, the term "cycloalkylalkyl" means a —$R_dR_e$ group where $R_d$ is an alkylene group and $R_e$ is cycloalkyl group. A representative example of a cycloalkylalkyl group is cyclohexylmethyl and the like.

As used herein, the term "halogen" means a —Cl, —Br, —I or —F; the term "halide" means a binary compound, of which one part is a halogen atom and the other part is an element or radical that is less electronegative than the halogen, e.g., an alkyl radical.

As used herein, the term "hydroxyl" means an —OH group.

As used herein, the term "nitro" means a —$NO_2$ group.

As used herein, the term "oxoalkyl" refers to —$(CH_2)$—C(O)$R_a$, where $R_a$ is hydrogen, alkyl, cycloalkyl, cycloalkylalkyl, phenyl or phenylalkyl and where n is from 1 to 10.

As used herein, the term "phenylalkyl" means an alkyl group which is substituted by a phenyl group.

As used herein, the term "sulfo" means a —$SO_3H$ group.

As used herein, the term "sulfoalkyl" refers to a —$(CH_2)_n$—$SO_3H$ or —$(CH_2)_n$—$SO_3^-$ group where n is from 1 to 10.

b) Anion

As used herein, the term "anion" refers to an anion of an inorganic or organic acid, such as, but not limited to, hydrochloric acid, hydrobromic acid, sulfuric acid, methane sulfonic acid, formic acid, acetic acid, oxalic acid, succinic acid, tartaric acid, mandelic acid, fumaric acid, lactic acid, citric acid, glutamic acid, aspartic acid, phosphate, trifluoromethansulfonic acid, trifluoroacetic acid and fluorosulfonic acid and any combinations thereof.

c) Antibody

As used herein, the term "antibody" refers to a protein consisting of one or more polypeptides substantially encoded by immunoglobulin genes or fragments of immunoglobulin genes, and encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. As represented here the notation format "$A_{a^n}^{n'}$" is meant to indicate an antibody that binds to epitope n on antigen n'. For example, $A_{a^1}^1$ may be an antibody that binds to one epitope on antigen $a^1$ where antigen $a^1$ is cardiac troponin-I and $A_{a^2}^1$ may be an antibody that binds to one epitope on antigen $a^2$ where antigen $a^2$ is cardiac troponin-T.

d) Hydrogen Peroxide Generating Enzyme

As used herein, the term "hydrogen peroxide generating enzyme" refers to an enzyme that is capable of producing as a reaction product the chemical compound having the molecular formula $H_2O_2$, i.e. hydrogen peroxide. Non-limiting examples of hydrogen peroxide generating enzymes are listed below in Table A-1.

TABLE A-1

| ACCEPTED COMMON NAME | IUBMB ENZYME NOMENCLATURE | PREFERRED SUBSTRATE |
|---|---|---|
| (R)-6-hydroxynicotine oxidase | EC 1.5.3.6 | (R)-6-hydroxynicotine |
| (S)-2-hydroxy acid oxidase | EC 1.1.3.15 | S)-2-hydroxy acid |
| (S)-6-hydroxynicotine oxidase | EC 1.5.3.5 | (S)-6-hydroxynicotine |
| 3-aci-nitropropanoate oxidase | EC 1.7.3.5 | 3-aci-nitropropanoate |
| 3-hydroxyanthranilate oxidase | EC 1.10.3.5 | 3-hydroxyanthranilate |
| 4-hydroxymandelate oxidase | EC 1.1.3.19 | (S)-2-hydroxy-2-(4-hydroxyphenyl)acetate |
| 6-hydroxynicotinate dehydrogenase | EC 1.17.3.3 | 6-hydroxynicotinate |
| Abscisic-aldehyde oxidase | EC 1.2.3.14 | abscisic aldehyde |
| acyl-CoA oxidase | EC 1.3.3.6 | acyl-CoA |
| Alcohol oxidase | EC 1.1.3.13 | a primary alcohol |
| Aldehyde oxidase | EC 1.2.3.1 | an aldehyde |
| amine oxidase | | |
| amine oxidase (copper-containing) | EC 1.4.3.6 | primary monoamines, diamines and histamine |
| amine oxidase (flavin-containing) | EC 1.4.3.4 | a primary amine |
| aryl-alcohol oxidase | EC 1.1.3.7 | an aromatic primary alcohol (2-naphthyl)methanol 3-methoxybenzyl alcohol |
| aryl-aldehyde oxidase | EC 1.2.3.9 | an aromatic aldehyde |
| Catechol oxidase | EC 1.1.3.14 | Catechol |
| cholesterol oxidase | EC 1.1.3.6 | Cholesterol |
| Choline oxidase | EC 1.1.3.17 | Choline |
| columbamine oxidase | EC 1.21.3.2 | Columbamine |
| cyclohexylamine oxidase | EC 1.4.3.12 | Cyclohexylamine |
| cytochrome c oxidase | EC 1.9.3.1 | |
| D-amino-acid oxidase | EC 1.4.3.3 | a D-amino acid |
| D-arabinono-1,4-lactone oxidase | EC 1.1.3.37 | D-arabinono-1,4-lactone |
| D-arabinono-1,4-lactone oxidase | EC 1.1.3.37 | D-arabinono-1,4-lactone |
| D-aspartate oxidase | EC 1.4.3.1 | D-aspartate |
| D-glutamate oxidase | EC 1.4.3.7 | D-glutamate |
| D-glutamate(D-aspartate) oxidase | EC 1.4.3.15 | D-glutamate |
| dihydrobenzophenanthridine oxidase | EC 1.5.3.12 | dihydrosanguinarine |
| dihydroorotate oxidase | EC 1.3.3.1 | (S)-dihydroorotate |
| dihydrouracil oxidase | EC 1.3.3.7 | 5,6-dihydrouracil |
| dimethylglycine oxidase | EC 1.5.3.10 | N,N-dimethylglycine |
| D-mannitol oxidase | EC 1.1.3.40 | Mannitol |
| Ecdysone oxidase | EC 1.1.3.16 | Ecdysone |
| ethanolamine oxidase | EC 1.4.3.8 | Ethanolamine |
| Galactose oxidase | EC 1.1.3.9 | D-galactose |
| Glucose oxidase | EC 1.1.3.4 | β-D-glucose |
| glutathione oxidase | EC 1.8.3.3 | Glutathione |
| Glycerol-3-phosphate oxidase | EC 1.1.3.21 | sn-glycerol 3-phosphate |
| Glycine oxidase | EC 1.4.3.19 | Glycine |
| glyoxylate oxidase | EC 1.2.3.5 | Glyoxylate |
| hexose oxidase | EC 1.1.3.5 | D-glucose, D-galactose D-mannose maltose lactose cellobiose |
| hydroxyphytanate oxidase | EC 1.1.3.27 | L-2-hydroxyphytanate |
| indole-3-acetaldehyde oxidase | EC 1.2.3.7 | (indol-3-yl)acetaldehyde |
| lactic acid oxidase | | Lactic acid |
| L-amino-acid oxidase | EC 1.4.3.2 | an L-amino acid |
| L-aspartate oxidase | EC 1.4.3.16 | L-aspartate |
| L-galactonolactone oxidase | EC 1.3.3.12 | L-galactono-1,4-lactone |
| L-glutamate oxidase | EC 1.4.3.11 | L-glutamate |
| L-gulonolactone oxidase | EC 1.1.3.8 | L-gulono-1,4-lactone |
| L-lysine 6-oxidase | EC 1.4.3.20 | L-lysine |
| L-lysine oxidase | EC 1.4.3.14 | L-lysine |
| long-chain-alcohol oxidase | EC 1.1.3.20 | A long-chain-alcohol |
| L-pipecolate oxidase | EC 1.5.3.7 | L-pipecolate |
| L-sorbose oxidase | EC 1.1.3.11 | L-sorbose |
| malate oxidase | EC 1.1.3.3 | (S)-malate |
| methanethiol oxidase | EC 1.8.3.4 | Methanethiol |
| monoamino acid oxidase | | |
| N$^6$-methyl-lysine oxidase | EC 1.5.3.4 | 6-N-methyl-L-lysine |
| N-acylhexosamine oxidase | EC 1.1.3.29 | N-acetyl-D-glucosamine N-glycolylglucosamine N-acetylgalactosamine N-acetylmannosamine. |
| NAD(P)H oxidase | EC 1.6.3.1 | NAD(P)H |
| nitroalkane oxidase | EC 1.7.3.1 | a nitroalkane |
| N-methyl-L-amino-acid oxidase | EC 1.5.3.2 | an N-methyl-L-amino acid |
| nucleoside oxidase | EC 1.1.3.39 | Adenosine |
| Oxalate oxidase | EC 1.2.3.4 | Oxalate |
| polyamine oxidase | EC 1.5.3.11 | 1-N-acetylspermine |
| polyphenol oxidase | EC 1.14.18.1 | |

TABLE A-1-continued

| ACCEPTED COMMON NAME | IUBMB ENZYME NOMENCLATURE | PREFERRED SUBSTRATE |
|---|---|---|
| Polyvinyl-alcohol oxidase | EC 1.1.3.30 | polyvinyl alcohol |
| prenylcysteine oxidase | EC 1.8.3.5 | an S-prenyl-L-cysteine |
| Protein-lysine 6-oxidase | EC 1.4.3.13 | peptidyl-L-lysyl-peptide |
| putrescine oxidase | EC 1.4.3.10 | butane-1,4-diamine |
| Pyranose oxidase | EC 1.1.3.10 | D-glucose D-xylose L-sorbose D-glucono-1,5-lactone |
| Pyridoxal 5'-phosphate synthase | EC 1.4.3.5 | pyridoxamine 5'-phosphate |
| pyridoxine 4-oxidase | EC 1.1.3.12 | Pyridoxine |
| pyrroloquinoline-quinone synthase | EC 1.3.3.11 | 6-(2-amino-2-carboxyethyl)-7,8-dioxo-1,2,3,4,5,6,7,8-octahydroquinoline-2,4-dicarboxylate |
| Pyruvate oxidase | EC 1.2.3.3 | Pyruvate |
| Pyruvate oxidase (CoA-acetylating) | EC 1.2.3.6 | Pyruvate |
| Reticuline oxidase | EC 1.21.3.3 | Reticuline |
| retinal oxidase | EC 1.2.3.11 | Retinal |
| Rifamycin-B oxidase | EC 1.10.3.6 | rifamycin-B |
| Sarcosine oxidase | EC 1.5.3.1 | Sarcosine |
| secondary-alcohol oxidase | EC 1.1.3.18 | a secondary alcohol |
| sulfite oxidase | EC 1.8.3.1 | Sulfite |
| superoxide dismutase | EC 1.15.1.1 | Superoxide |
| superoxide reductase | EC 1.15.1.2 | Superoxide |
| tetrahydroberberine oxidase | EC 1.3.3.8 | (S)-tetrahydroberberine |
| Thiamine oxidase | EC 1.1.3.23 | Thiamine |
| tryptophan α,β-oxidase | EC 1.3.3.10 | L-tryptophan |
| urate oxidase (uricase, uric acid oxidase) | EC 1.7.3.3 | uric acid |
| Vanillyl-alcohol oxidase | EC 1.1.3.38 | vanillyl alcohol |
| Xanthine oxidase | EC 1.17.3.2 | Xanthine |
| xylitol oxidase | EC 1.1.3.41 | Xylitol | e) Autoantibody

As used herein, the phrase "autoantibody" refers to an antibody that binds to an analyte that is endogenously produced in the subject in which the antibody is produced.

f) n' (n-Antibody:Antigen) Immuno-Complexes

As used herein, the phrase "n' (n-antibody:antigen) immuno-complexes" refers to a combination of n antibodies A and n' cardiac myocyte antigens a, wherein the antibodies and antigens are bound by specific, noncovalent interactions between at least one antigen-combining site on each antibody and at least one epitope on each of n' cardiac myocyte antigen $a^{n'}$, wherein n is an integer from 1 to 10 and n' is an integer from 2 to 10. As represented here the notation format $(A_{a^1}^1)(A_{a^1}^2) \ldots (A_{a^1}^n)(a^1)$, $(A_{a^2}^1)(A_{a^2}^2) \ldots (A_{a^2}^n)(a^2)$, $\ldots (A_{a^{n'}}^1)(A_{a^{n'}}^2) \ldots (A_{a^{n'}}^n)(a^{n'})$ is meant to indicate two or more antibody:antigen immuno-complexes. For example, $(A_{a^1}^1)(A_{a^1}^2) \ldots (A_{a^1}^n)(a^1)$ is a first antibody:antigen immuno-complex, wherein $A_{a^1}^1$ is a first antibody that binds to one epitope on antigen $a^1$, and optionally, $A_{a^1}^2$ is a second antibody that binds to a second epitope on antigen $a^1$ and so on up to $A_{a^1}^n$, which is a nth antibody that binds to a nth epitope on antigen $a^1$ where the antigen $a^1$ is cardiac troponin-I; and $(A_{a^2}^1)(A_{a^2}^2) \ldots (A_{a^2}^n)(a^2)$ is a second antibody:antigen immuno-complex, wherein $A_{a^2}^1$ is a first antibody that binds to one epitope on antigen $a^2$, and optionally, $A_{a^2}^2$ is a second antibody that binds to a second epitope on antigen $a^2$ and so on up to $A_{a^2}^n$, which is a nth antibody that binds to a nth epitope on antigen $a^2$ where the antigen $a^2$ is cardiac troponin-T.

g) n' ((n+n") Antibody:Antigen) Measurable Assemblies

As used herein, the term "n' ((n+n") antibody:antigen) measurable assemblies" refers to a combination of n antibodies A, n" antibodies B and n' cardiac myocyte antigens a to form n' (n+n") measurable antibody:antigen immuno-complexes, wherein n and n" are independently an integer from 1 to 10, n' is an integer from 2 to 10, and antibodies A and B bind to (n+n") different epitopes of a cardiac myocyte antigen. The combination of antibodies and cardiac myocyte antigens produces an optical, electrical, or change-of-state signal that can be detected and quantified and thus the combination is "measurable". As represented here the notation format $((A_{a^1}^1)(A_{a^1}^2) \ldots (A_{a^1}^n)((B_{a^1}^1)(B_{a^1}^2) \ldots (B_{a^1}^n)(a^1)$, $((A_{a^2}^1)(A_{a^2}^2) \ldots (A_{a^2}^n))((B_{a^2}^1)(B_{a^2}^2) \ldots (B_{a^2}^n))(a^2)$, $\ldots ((A_{a^{n'}}^1)(A_{a^{n'}}^2) \ldots (A_{a^{n'}}^n))((B_{a^{n'}}^1)(B_{a^{n'}}^2) \ldots (B_{a^{n'}}^n))(a^{n'})$ is meant to indicate two or more antibody:antigen measurable assemblies. For example, $((A_{a^1}^1)(A_{a^1}^2) \ldots (A_{a^1}^n)((B_{a^1}^1)(B_{a^1}^2) \ldots (B_{a^1}^n)(a^1)$ is a first measurable assembly wherein $A_{a^1}^1$ is a first antibody that binds to one epitope on antigen $a^1$, and optionally, $A_{a^1}^2$ is a second antibody that binds to a second epitope on antigen $a^1$ and so on up to $A_{a^1}^n$, which is a nth antibody that binds to a nth epitope on antigen $a^1$, and $B_{a^1}^1$ is a first antibody that binds to one epitope on antigen $a^1$, and optionally, $B_{a^1}^2$ is a second antibody that binds to a second epitope on antigen $a^1$ and so on up to $B_{a^1}^n$, which is a nth antibody that binds to a nth epitope on antigen $a^1$, where the antigen $a^1$ is cardiac troponin-I; and $(A_{a^1}^2)(A_{a^2}^2) \ldots (A_{a^2}^n)((B_{a^2}^1)(B_{a^2}^2) \ldots (B_{a^2}^n)(a^2)$ is a second measurable assembly, wherein $A_{a^2}^1$ is a first antibody that binds to one epitope on antigen $a^2$, and optionally, $A_{a^2}^2$ is a second antibody that binds to a second epitope on antigen $a^2$ and so on up to $A_{a^2}^n$ which is a nth antibody that binds to a nth epitope on antigen $a^2$ and wherein $B_{a^2}^1$ is a first antibody that binds to one epitope on antigen $a^2$, and optionally, $B_{a^2}^2$ is a second antibody that binds to a second epitope on antigen $a^2$ and so on up to $B_{a^2}^n$ which is a nth antibody that binds to a nth epitope on antigen $a^2$ where the antigen $a^2$ is cardiac troponin-T.

h) Detectable Label

As used herein the term "detectable label" refers to any moiety that generates a measurable signal via optical, electrical, or other physical indication of a change of state of a molecule or molecules coupled to the moiety. Such physical indicators encompass spectroscopic, photochemical, biochemical, immunochemical, electromagnetic, radiochemical, and chemical means, such as but not limited to fluorescence, chemifluorescence, chemiluminescence, and the like. Preferred detectable labels include acridinium compounds such as an acridinium-9-carboximide having a structure according to Formula I as set forth in section B herein below, and an acridinium-9-carboxylate aryl ester having a structure according to Formula II as also set forth in section B herein below.

i) Subject

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc) and a human). Preferably, the subject is a human.

j) Test Sample

As used herein, the term "test sample" generally refers to a biological material being tested for and/or suspected of containing an analyte of interest and which may also include autoantibodies to the analyte or analytes of interest. The biological material may be derived from any biological source but preferably is a biological fluid likely to contain cardiac myocyte antigens. Examples of biological materials include, but are not limited to, stool, whole blood, serum, plasma, red blood cells, platelets, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, soil, etc. The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. If such methods of pretreatment are employed with respect to the test sample, such pretreatment methods are such that cardiac myocyte antigens remain in the test sample at a concentration proportional to that in an untreated test sample (e.g., namely, a test sample that is not subjected to any such pretreatment method(s)).

B. Immunoassay for Detecting Cardiac Myocyte Antigens in a Test Sample

The present disclosure relates to an immunoassay for detecting cardiac myocyte antigens in a test sample, which is particularly useful for use with test samples that may contain other substances that may interfere with immunodetection of the cardiac myocyte antigens. Such substances include for example, heterophilic endogeneous antibodies, and autoantibodies against the cardiac myocyte antigens. The immunoassay of the present disclosure involves obtaining a test sample from a subject and then detecting the presence of cardiac myocyte antigens using immunodetection while compensating for the presence of any such substances that may be present in the sample. This is achieved in part by providing n antibodies $(A_{a^n}{}'')$ that bind to n' cardiac myocyte antigens $(a'')$ to form n' antibody:antigen immuno-complexes $(A_{a^1}{}^1)(A_{a^1}{}^2)\ldots(A_{a^1}{}^n)(a^1), (A_{a^2}{}^1)(A_{a^2}{}^2)\ldots(A_{a^2}{}^n)(a^2), \ldots (A_{a^n}{}^n)(a^{n'})$ and n" antibodies $(B_{a^n}{}'')$ that bind to n' cardiac myocyte antigens $(a'')$ to form a measurable assembly of n' antibody: antigen immuno-complexes $((A_{a^1}{}^1)(A_{a^1}{}^2)\ldots(A_{a^1}{}'')((B_{a^1}{}^1)(B_{a^1}{}^2)\ldots(B_{a^1}{}'')(a^1), ((A_{a^2}{}^1)(A_{a^2}{}^2)\ldots(A_{a^2}{}''))((B_{a^2}{}^1)(B_{a^2}{}^2)\ldots(B_{a^2}{}''))(a^2), \ldots ((A_{a^n}{}^1)(A_{a^n}{}^2)\ldots(A_{a^n}{}''))((B_{a^n}{}^1)(B_{a^n}{}^2)\ldots(A_{a^n}{}''))(a^{n'})$, wherein each cardiac myocyte antigen $a^{n'}$ is independently comprised of at least two epitopes, wherein the antibodies $A_{a^n}{}''$ and $B_{a^n}{}''$ bind to n different epitopes on the antigen all, and wherein n is an integer from 1 to 10. In other words, each of n antibodies $A_{a^n}{}''$ binds to at least one epitope on cardiac myocyte antigen $a''$, and each of n antibodies $B_n$ binds to at least one epitope on cardiac myocyte antigen $a''$ that is different than any of the epitopes to which any of the n antibodies $A_{a^n}{}''$ bind. The antibodies $B_{a^n}{}''$ can be for example "detection antibodies" labeled with a detectable label. The antibodies can be provided on a solid phase, which can be a solid support, on which for example the antibodies $A_{a^n}{}''$ or $B_{a^n}{}''$ are immobilized.

Immunoassay Methods

The immunoassay methods of the present disclosure can be carried out in any of a wide variety of formats. A general review of immunoassays is available in METHODS IN CELL BIOLOGY VOLUME 37: ANTIBODIES IN CELL BIOLOGY, Asai, ed. Academic Press, Inc. New York (1993), and BASIC AND CLINICAL IMMUNOLOGY 7TH EDITION, Stites & Terr, eds. (1991), which are herein incorporated by reference in its entirety. A typical heterogeneous sandwich immunoassay employs a solid phase (as a solid support) to which is bound a first (capture) antibody reactive with at least one epitope on an analyte of interest that is an antigen. A second (detection) antibody is also reactive with at least one epitope on the analyte of interest that is an antigen. The second antibody may be conjugated to a detectable label that provides a signal that is measured after the detection antibody binds to the captured analyte. When a test sample containing the analyte contacts the first antibody, the first antibody captures the analyte of interest. The analyte of interest is contacted with the second antibody resulting in the formation of an immunodetection complex consisting of the first antibody, analyte of interest and second antibody, and the complex is bound to the solid phase. The signal generated by the second (detection) antibody is proportional to the concentration of the analyte of interest as determined by the rate of formation $(k_1)$ of the immunodetection complex versus the rate of dissociation of the immunodetection complex $(k_2)$. Heterophilic endogenous antibodies and any autoantibodies, which if present are unpredictable as to exactly where on the analyte of interest they will bind, can substantially interfere with binding of the first and/or second antibody, and thus with the resulting signal.

In contrast to known immunoassays, immunoassays of the present disclosure are based on combining the results of immunodetection of at least two analytes of interest, which are cardiac myocyte antigens. The cardiac myocyte antigens a can be any antigen for which an association has been established between elevated in vivo levels of the antigen, and cardiac myocyte damage. Known such antigens include for example cardiac troponin-I, cardiac troponin-T, creatine phosphokinase MB (CKMB), myoglobin, myosin heavy chain, myosin light chain, B-type natriuretic peptide (including pro-BNP, NT-proBNP, and hBNP(1-32)), heart fatty-acid-binding protein (H-FABP), placenta growth factor (PLGF), and interleukin-6 (IL-6). In an exemplary embodiment of the immunoassay, two cardiac myocyte antigens are used and are for example troponin I (cTnI) and cardiac troponin-T (cTnT).

Also in contrast to a typical immunoassay format, and as described elsewhere herein, immunoassays according to an exemplary embodiment of the present disclosure employ multiple antibodies $A_{a^n}$ and multiple antibodies $B_{a^n}$ wherein each antibody $A_{a^n}$ binds to at least one epitope on a cardiac myocyte antigen $a^{n'}$ that is different than any of the epitopes to which the antibodies $B_{a^n}$ bind. The use of multiple antibodies $A_{a^n}$ and $B_{a^n}$ wherein $A_{a^n}$ and $B_{a^n}$ are distinguished by a lack of binding specificity for the same epitopes on any given cardiac myocyte antigen $a^{n'}$, improves the specificity of the detection, improves the quality of signal and therefore its accuracy as to cardiac myocyte damage, and also decreases noise in the signal from nonspecific binding due to the presence of any heterophilic endogenous antibodies and/or autoantibodies. A signal generated by the antibodies $B_{a^n}$ remains proportional to the combined concentrations of the n' cardiac myocyte antigens $a^{n'}$, but is determined by the rate of formation of new immunodetection complexes: $((A_{a^1})(A_{a^1}^2) \ldots (A_{a^1}^{n})((B_{a^1}^1)(B_{a^1}^2) \ldots (B_{a^1}^{n})(a^1), ((A_{a^2}^1)(A_{a^2}^2) \ldots (A_{a^2}^{n})((B_{a^2}^1)(B_{a^2}^2) \ldots (B_{a^2}^{n})(a^2), \ldots ((A_{a^{n'}}^1)(A_{a^{n'}}^2) \ldots (A_{a^{n'}}^{n}))((B_{a^{n'}}^1)(B_{a^{n'}}^2) \ldots (B_{a^{n'}}^{n})(a^{n'})$, versus the rate of dissociation of the new immunodetection complexes. Use of more than one antibody $A_{a^n}$ and more than one antibody, $B_{a^n}$ thus improves accuracy of the immunoassay by increasing the signal from specific binding to each cardiac myocyte antigen $a^{n'}$. The methods also provide for the use of humanized immunoreagents, which overcomes any interference from heterophilic antibodies that may be present in the test sample. Additionally, antihuman IgG antibody can be used for the antibodies $B_{a^n}$ to correct for endogenous autoantibodies to each cardiac myocyte antigens $a^{n'}$. Moreover, when used in conjunction with humanized immunoreagents, antihuman IgG provides a "universal" signal generator. Derivatized cardiac myocyte antigens, such as for example derivatized cardiac troponin-I or derivatized cardiac troponin-T can be used to provide a soluble reagent suitable for assay standardization. For example, the cardiac myocyte antigens can be suitable derivatized with a polyethylene glycol.

Thus, according to one embodiment, an immunoassay of the present disclosure to detect the presence of at least two cardiac myocyte antigens $a^{n'}$ is a heterogeneous assay, which can employ a solid phase, which can be a solid support. The immunoassay can be performed for example by immobilizing one or more antibodies $(A_{a^1}^1), (A_{a^1}^2), \ldots (A_{a^n}^{n})$ on the solid phase, wherein each antibody $A_{a^n}$ is an exogenous antibody that is reactive with at least one epitope on cardiac myocyte antigen $a^{n'}$. Under conditions sufficient for specific binding of each antibody $A_{a^n}$ to $a^{n'}$, the test sample suspected of containing cardiac myocyte antigens $(a^1), (a^2), \ldots (a^{n'})$, and which may or may not contain other interfering substances, is contacted with the antibodies $(A_{a^1}^1), (A_{a^1}^2), \ldots (A_{a^n}^{n})$, thus forming the immune complex $(A_{a^1}^1)(A_{a^1}^2) \ldots (A_{a^1}^{n})(a^1), (A_{a^2}^1)(A_{a^2}^2) \ldots (A_{a^2}^{n})(a^2), \ldots (A_{a^{n'}}^1)(A_{a^{n'}}^2) \ldots (A_{a^{n'}}^{n})(a^{n'})$. The immune complex $(A_{a^1}^1)(A_{a^1}^2) \ldots (A_{a^1}^{n})(a^1), (A_{a^2}^1)(A_{a^2}^2) \ldots (A_{a^2}^{n})(a^2), \ldots (A_{a^{n'}}^1)(A_{a^{n'}}^2) \ldots (A_{a^{n'}}^{n})(a^{n'})$, is contacted with antibodies $(B_{a^1}^1), (B_{a^1}^2), \ldots (B_{a^n}^{n})$, to form the measurable assembly of n' antibody:antigen immuno-complexes $((A_{a^1}^1)(A_{a^1}^2) \ldots (A_{a^1}^{n})((B_{a^1}^1)(B_{a^1}^2) \ldots (B_{a^1}^{n}))(a^1), ((A_{a^2}^1)(A_{a^2}^2) \ldots (A_{a^2}^{n}))((B_{a^2}^1)(B_{a^2}^2) \ldots (B_{a^2}^{n}))(a^2), \ldots (A_{a^{n'}}^1)(A_{a^{n'}}^2) \ldots (A_{a^{n'}}^{n}))((B_{a^{n'}}^1)(B_{a^{n'}}^2) \ldots (B_{a^{n'}}^{n})(a^{n'})$, wherein each cardiac myocyte antigen $a^{n'}$ is independently comprised of at least two epitopes, and wherein the antibodies $A_{a^n}$ and $B_{a^n}$ bind to n different epitopes on the antigen $a^{n'}$, wherein n' is an integer from 2 to 10. This step is carried out under conditions sufficient for specific binding of the antibodies $B_{a^n}$ to any of the cardiac myocyte antigen $a^{n'}$ that is present in the test sample.

By "measurable assembly" is meant a configuration of molecules that when formed generates a signal susceptible to physical detection and/or quantification. In certain embodiments for example, the antibodies $B_{a^n}$ may be labeled with a detectable label. Depending on the detection approach used, an optical, electrical, or change-of-state signal of the assembly is measured. Additionally, antihuman IgG antibody can be used for the detection antibodies, which corrects for endogeneous autoantibodies to the cardiac myocyte antigen $a^{n'}$.

Although the immunoassay is described above as including a sequence of steps for illustrative purposes, the test sample may be contacted with the antibodies A and the detection antibodies B simultaneously or sequentially, in any order.

In one format of a sandwich immunoassay according to the present disclosure, detecting comprises detecting a signal from the solid phase-affixed immunodetection complex which is n' antibody:antigen immuno-complexes $((A_{a^1}^1)(A_{a^1}^2) \ldots (A_{a^1}^{n})((B_{a^1}^1)(B_{a^1}^2) \ldots (B_{a^1}^{n})(a^1), ((A_{a^2}^1)(A_{a^2}^2) \ldots (A_{a^2}^{n}))((B_{a^2}^1)(B_{a^2}^2) \ldots (B_{a^2}^{n}))(a^2), \ldots (A_{a^{n'}}^1)(A_{a^{n'}}^2) \ldots (A_{a^{n'}}^{n}))((B_{a^{n'}}^1)(B_{a^{n'}}^2) \ldots (B_{a^{n'}}^{n}))(a^{n'})$. In one embodiment, the immunodetection complexes are separated from the solid phase, typically by washing, and the signal from the bound label is detected. In another format of a sandwich immunoassay according to the present disclosure, the immunodetection complexes remain as solid phase-affixed complexes, which are then detected.

Antibodies

In the immunoassays according to the present disclosure, each antibody $A_{a^n}$ can be a polyclonal antibody, a monoclonal antibody, a chimeric antibody, a human antibody, an affinity maturated antibody or an antibody fragment. Similarly, each antibody $B_{a^n}$ can be a polyclonal antibody, a monoclonal antibody, a chimeric antibody, a human antibody, an affinity maturated antibody or an antibody fragment.

While monoclonal antibodies are highly specific to the analyte/antigen, a polyclonal antibody can preferably be used as each antibody $A_{a^n}$ to immobilize as much of the analyte/antigen as possible. A monoclonal antibody with inherently higher binding specificity for the analyte/antigen may then preferably be used for each antibody $B_{a^n}$. In any case, the antibodies $A_{a^n}$ and $B_{a^n}$ recognize non-overlapping epitopes on each cardiac myocyte antigen $a^{n'}$, and in an exemplary embodiment are capable of binding simultaneously to different epitopes on each cardiac myocyte antigen, each without interfering with the binding of the other.

Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen.

If desired, the cardiac myocyte antigen(s) may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies (see, e.g., Coligan, et al. (1991) Unit 9, Current Protocols in Immunology, Wiley Interscience).

For many applications, monoclonal antibodies (mAbs) are preferred. The general method used for production of hybridomas secreting mAbs is well known (Kohler and Milstein (1975) Nature, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552-554; Hoogenboom et al. (1991) Nucleic Acids Res. 19: 4133-4137).

Since the antibody fragments on the surface of the phage are functional, phage-bearing antigen-binding antibody fragments can be separated from non-binding phage by antigen affinity chromatography (McCafferty et al. (1990) Nature, 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) Nature, 348: 552-554). Thus, even when enrichments are low (Marks et al. (1991) J. Mol. Biol. 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen. Human antibodies can be produced without prior immunization by displaying very large and diverse V-gene repertoires on phage (Marks et al. (1991) J. Mol. Biol. 222: 581-597). In one embodiment, natural VH and VL repertoires present in human peripheral blood lymphocytes are isolated from unimmunized donors by PCR. The V-gene repertoires can be spliced together at random using PCR to create a scFv gene repertoire which can be cloned into a phage vector to create a library of 30 million phage antibodies (Id.). From a single "naïve" phage antibody library, binding antibody fragments have been isolated against more than 17 different antigens, including haptens, polysaccharides, and proteins (Marks et al. (1991) J. Mol. Biol. 222: 581-597; Marks et al. (1993). Bio/Technology. 10: 779-783; Griffiths et al. (1993) EMBO J. 12: 725-734; Clackson et al. (1991) Nature. 352: 624-628). Antibodies have been produced against self proteins, including human thyroglobulin, immunoglobulin, tumor necrosis factor, and CEA (Griffiths et al. (1993) EMBO J. 12: 725-734). The antibody fragments are highly specific for the antigen used for selection and have affinities in the 1 nM to 100 nM range (Marks et al. (1991) J. Mol. Biol. 222: 581-597; Griffiths et al. (1993) EMBO J. 12: 725-734). Larger phage antibody libraries result in the isolation of more antibodies of higher binding affinity to a greater proportion of antigens.

As those of skill in the art readily appreciate, antibodies can be prepared by any of a number of commercial services (e.g., Berkeley Antibody Laboratories, Bethyl Laboratories, Anawa, Eurogenetec, etc.).

Solid Phase

A solid phase can be any suitable material with sufficient surface affinity to bind an antibody, for example each antibody $A_{a^n}{}^n$ or each antibody $B_{a^n}{}^n$, or each antibody $A_{a^n}{}^n$ and each antibody $B_{a^n}{}^n$. In an exemplary embodiment, each $A_{a^n}{}^n$ is bound to a solid phase. The solid phase can take any of a number of forms, such as a magnetic particle, bead, test tube, microtiter plate, cuvette, membrane, a scaffolding molecule, quartz crystal, film, filter paper, disc or a chip. Useful solid phase materials include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, tubes, particulates, or plates, or they may be coated onto, bonded, or laminated to appropriate inert carriers, such as paper, glass, plastic films, fabrics, or the like. Nitrocellulose has excellent absorption and adsorption qualities for a wide variety of reagents including monoclonal antibodies. Nylon also possesses similar characteristics and also is suitable.

Alternatively, the solid phase can constitute microparticles. Microparticles useful in the present disclosure can be selected by one skilled in the art from any suitable type of particulate material and include those composed of polystyrene, polymethylacrylate, polypropylene, latex, polytetrafluoroethylene, polyacrylonitrile, polycarbonate, or similar materials. Further, the microparticles can be magnetic or paramagnetic microparticles, so as to facilitate manipulation of the microparticle within a magnetic field. In an exemplary embodiment the microparticles are carboxylated magnetic microparticles.

Microparticles can be suspended in the mixture of soluble reagents and test sample or can be retained and immobilized by a support material. In the latter case, the microparticles on or in the support material are not capable of substantial movement to positions elsewhere within the support material. Alternatively, the microparticles can be separated from suspension in the mixture of soluble reagents and test sample by sedimentation or centrifugation. When the microparticles are magnetic or paramagnetic the microparticles can be separated from suspension in the mixture of soluble reagents and test sample by a magnetic field.

The methods of the present disclosure can be adapted for use in systems that utilize microparticle technology including automated and semi-automated systems wherein the solid phase comprises a microparticle. Such systems include those described in pending U.S. application Ser. No. 425,651 and U.S. Pat. No. 5,089,424, which correspond to published EPO App. Nos. EP 0 425 633 and EP 0 424 634, respectively, and U.S. Pat. No. 5,006,309.

In particular embodiments, the solid phase includes one or more electrodes. For example, antibodies $A_{a''}^n$ can be affixed for example, directly or indirectly, to the electrode(s). In one embodiment, for example, antibodies $A_{a''}^n$ can be affixed to magnetic or paramagnetic microparticles, which are then positioned in the vicinity of the electrode surface using a magnet. Systems in which one or more electrodes serve as the solid phase are useful where detection is based on electrochemical interactions. Exemplary systems of this type are described, for example, in U.S. Pat. No. 6,887,714 (issued May 3, 2005). The basic method is described further below with respect to electrochemical detection.

The antibodies $A_{a''}^n$ or $B_{a''}^n$ can be attached to the solid phase by adsorption, where they are retained by hydrophobic forces. Alternatively, the surface of the solid phase can be activated by chemical processes that cause covalent linkage of the antibodies to the support.

To change or enhance the intrinsic charge of the solid phase, a charged substance can be coated directly onto the solid phase. Ion capture procedures for immobilizing an immobilizable reaction complex with a negatively charged polymer, described in U.S. application Ser. No. 150,278, corresponding to EP Publication No. 0326100, and U.S. application Ser. No. 375,029 (EP Publication No. 0406473), can be employed according to the present disclosure to affect a fast solution-phase immunochemical reaction. In these procedures, an immobilizable immune complex is separated from the rest of the reaction mixture by ionic interactions between the negatively charged polyanion/immune complex and the previously treated, positively charged matrix and detected by using any of a number of signal-generating systems, including, e.g., chemiluminescent systems, as described in U.S. application Ser. No. 921,979, corresponding to EPO Publication No. 0 273,115.

If the solid phase is silicon or glass, the surface must generally be activated prior to attaching each antibody $A_{a''}^n$ or $B_{a''}^n$. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the antibodies directly (in the cases of amino or thiol), or the activated surface can be further reacted with linkers such as glutaraldehyde, bis(succinimidyl) suberate, SPPD 9 succinimidyl 3-[2-pyridyldithio]propionate), SMCC (succinimidyl-4-[Nmaleimidomethyl]cyclohexane-1-carboxylate), SIAB (succinimidyl[4iodoacetyl]aminobenzoate), and SMPB (succinimidyl 4-[1 maleimidophenyl]butyrate) to separate the antibody from the surface. Vinyl groups can be oxidized to provide a means for covalent attachment. Vinyl groups can also be used as an anchor for the polymerization of various polymers such as poly-acrylic acid, which can provide multiple attachment points for specific antibodies. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, polyelectrolyte interactions can be used to immobilize a specific antibody on a solid phase using techniques and chemistries described U.S. application Ser. No. 150,278, filed Jan. 29, 1988, and U.S. application Ser. No. 375,029, filed Jul. 7, 1989, each of which is incorporated herein by reference.

Other considerations affecting the choice of solid phase include the ability to minimize non-specific binding of labeled entities and compatibility with the labeling system employed. For, example, solid phases used with fluorescent labels should have sufficiently low background fluorescence to allow signal detection.

Following attachment of a specific antibody, the surface of the solid support may be further treated with materials such as serum, proteins, or other blocking agents to minimize non-specific binding.

Detection Systems in General

As discussed above, immunoassays according to the present disclosure employ one or more antibodies $B_{a''}^n$, each of which is specific to a cardiac myocyte antigen $a''$. In certain embodiments, each antibody $B_{a''}^n$ is bound to a detectable label.

Detectable labels suitable for use in the detection antibodies of the present disclosure include any compound or composition having a moiety that is detectable by spectroscopic, photochemical, biochemical, immunochemical, electrical, optical, or chemical means. Such labels include, for example, an enzyme, oligonucleotide, nanoparticle chemiluminophore, fluorophore, fluorescence quencher, chemiluminescence quencher, or biotin. Thus for example, in an immunoassay employing an optical signal, the optical signal is measured as an analyte concentration dependent change in chemiluminescence, fluorescence, phosphorescence, electrochemiluminescence, ultraviolet absorption, visible absorption, infrared absorption, refraction, surface plasmon resonance. In an immunoassay employing an electrical signal, the electrical signal is measured as an analyte concentration dependent change in current, resistance, potential, mass to charge ratio, or ion count. In an immunoassay employing a change-of-state signal, the change of state signal is measured as an analyte concentration dependent change in size, solubility, mass, or resonance.

Useful labels according to the present disclosure include magnetic beads (e.g., Dynabeads™), fluorescent dyes (e.g., fluorescein, Texas Red, rhodamine, green fluorescent protein) and the like (see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., $^3H$, $^{125}I$, $^{35}S$, $^{14}C$, or $^{32}P$), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.)

beads. Patents teaching the use of such labels include U.S. Pat. Nos. 3,817,837; 3,850,752; 3,939,350; 3,996,345; 4,277,437; 4,275,149; and 4,366,241.

The label can be attached to each antibody $B_{a^n}{''}$ prior to, or during, or after contact with the biological sample. The label can be attached by covalent or non-covalent interactions with the antibody. So-called "direct labels" are detectable labels that are directly attached to or incorporated into the detection antibody prior to use in the assay. Direct labels can be attached to or incorporated into the antibody $B_{a^n}{''}$ any of a number of means well known to those of skill in the art.

In contrast, so-called "indirect labels" typically bind to each antibody $B_{a^n}{''}$ at some point during the assay. Often, the indirect label binds to a moiety that is attached to or incorporated into the detection agent prior to use. Thus, for example, each antibody $B_{a^n}{''}$ can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542). Such polypeptides can thus be labeled and added to the assay mixture, where they will bind to each antibody $A_{a^n}{''}$ and $B_{a^n}{''}$, as well as to the autoantibodies, labeling all and providing a composite signal attributable to analyte and autoantibody present in the sample.

Some labels useful in the present disclosure may require the use of an additional reagent(s) to produce a detectable signal. In an ELISA, for example, an enzyme label (e.g., beta-galactosidase) will require the addition of a substrate (e.g., X-gal) to produce a detectable signal. In immunoassays using an acridinium compound as the direct label, a basic solution and a source of hydrogen peroxide are added.

Detection Systems—Exemplary Formats

Chemiluminescence Immunoassay: In an exemplary embodiment, a chemiluminescent compound is used in the above-described methods as a direct label conjugated to each antibody $B_{a^n}{''}$. The chemiluminescent compound can be for example an acridinium compound. When an acridinium compound is used as the detectable label, then the above-described method may further include generating or providing a source of hydrogen peroxide to the mixture resulting from contacting the test sample with antibodies A and the antibodies $B_{a^n}{''}$, and adding at least one basic solution to the mixture to generate a light signal. The light signal generated or emitted by the mixture is then measured to detect the cardiac myocyte antigens $a^{n'}$ in the test sample.

The source of hydrogen peroxide may be a buffer solution or a solution containing hydrogen peroxide or an enzyme that generates hydrogen peroxide when added to the test sample. The basic solution serves as a trigger solution, and the order in which the at least one basic solution and detectable label are added is not critical. The basic solution used in the method is a solution that contains at least one base and that has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate. The amount of basic solution added to the test sample depends on the concentration of the basic solution used in the assay. Based on the concentration of the basic solution used, one skilled in the art could easily determine the amount of basic solution to be used in the method described herein.

In a chemiluminescence immunoassay according to the present disclosure and using an acridinium compound as the detectable label, preferably the acridinium compound is an acridinium-9-carboxamide. Specifically, the acridinium-9-carboxamide has a structure according to formula I:

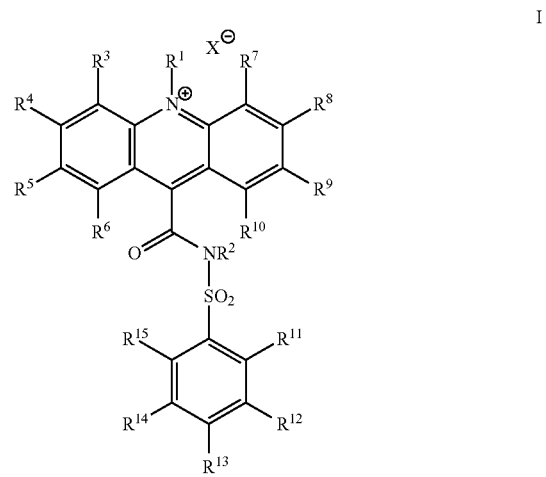

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^\ominus$ is an anion.

Methods for preparing acridinium 9-carboxamides are described in Mattingly, P. G. *J. Biolumin. Chemilumin.*, 6, 107-14; (1991); Adamczyk, M.; Chen, Y.-Y., Mattingly, P. G.; Pan, Y. *J. Org. Chem.*, 63, 5636-5639 (1998); Adamczyk, M.; Chen, Y.-Y.; Mattingly, P. G.; Moore, J. A.; Shreder, K. *Tetrahedron*, 55, 10899-10914 (1999); Adamczyk, M.; Mattingly, P. G.; Moore, J. A.; Pan, Y. *Org. Lett.*, 1, 779-781 (1999); Adamczyk, M.; Chen, Y.-Y.; Fishpaugh, J. R.; Mattingly, P. G.; Pan, Y.; Shreder, K.; Yu, Z. *Bioconjugate Chem.*, 11, 714-724 (2000); Mattingly, P. G.; Adamczyk, M. In *Luminescence Biotechnology: Instruments and Applications*; Dyke, K. V. Ed.; CRC Press: Boca Raton, pp. 77-105 (2002); Adamczyk, M.; Mattingly, P. G.; Moore, J. A.; Pan, Y. *Org. Lett.*, 5, 3779-3782 (2003); and U.S. Pat. Nos. 5,468,646, 5,543,524 and 5,783,699 (each incorporated herein by reference in their entireties for their teachings regarding same).

Alternatively, the acridinium compound can be an acridinium-9-carboxylate aryl ester; the acridinium-9-carboxylate aryl ester can have a structure according to formula II:

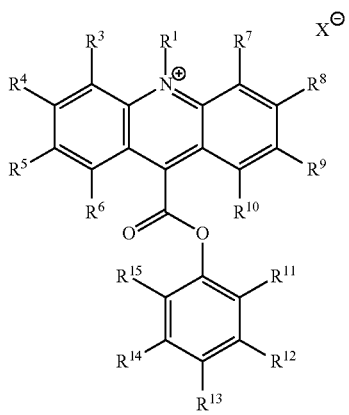

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

Examples of acridinium-9-carboxylate aryl esters having the above formula II that can be used in the present disclosure include, but are not limited to, 10-methyl-9-(phenoxycarbonyl)acridinium fluorosulfonate (available from Cayman Chemical, Ann Arbor, Mich.). Methods for preparing acridinium 9-carboxylate aryl esters are described in McCapra, F., et al., *Photochem. Photobiol.*, 4, 1111-21 (1965); Razavi, Z et al., *Luminescence,* 15:245-249 (2000); Razavi, Z et al., *Luminescence,* 15:239-244 (2000); and U.S. Pat. No. 5,241,070 (each incorporated herein by reference in their entireties for their teachings regarding same).

In addition to the at least one acridinium compound, the indicator solution can also contain at least one surfactant. Any surfactant that when dissolved in water, lowers the surface tension of the water and increases the solubility of organic compounds, can be used in the present invention. Examples of surfactants that can be used are one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-β-D-maltoside, polyoxyethylene (10) dodecyl ether (Genapol C-100), isotridecanol polyglycol ether (Genapol X-80), isotridecanol polyglycol ether (Genapol X-100), Heptane-1,2,3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Optionally, the test sample may be treated prior to the addition of any one or more of the at least one basic solution, hydrogen peroxide source and detectable label. Such treatment may include dilution, ultrafiltration, extraction, precipitation, dialysis, chromatography and digestion. Such treatment may be in addition to and separate from any pretreatment that the test sample may receive or be subjected to as discussed previously herein. Moreover, if such treatment methods are employed with respect to the test sample, such treatment methods are such that cardiac myocyte antigens remains in the test sample at a concentration proportional to that in an untreated test sample (e.g., namely, a test sample that is not subjected to any such treatment method(s)).

As mentioned briefly previously herein, the time and order in which the test sample, the at least one basic solution, source of hydrogen peroxide and the detectable label are added to form a mixture is not critical. Additionally, the mixture formed by the at least one basic solution, hydrogen peroxide source and the detectable label, can optionally be allowed to incubate for a period of time. For example, the mixture can be allowed to incubate for a period of time of from about 1 second to about 60 minutes. Specifically, the mixture can be allowed to incubate for a period of from about 1 second to about 18 minutes.

The detectable label used for each antibody $B_{a^{n'}}$ can be the same, provided that a suitable standard curve or reference standard is obtained for each antigen $a^{n'}$, the signal from each is measured separately and a calibrated measurement antigen amount for each antigen determined and then combined with those for each other antigen $a^{n'}$, to avoid confounding the results for each antigen. Different detectable labels for each antibody $B_{a^{n'}}$ may be used, and depending on the labeling compounds selected, may allow for the simultaneous measurement of signal from more than antigen $a^{n'}$ if the signals are readily distinguishable from one another. For example, different fluorescent labels having different emission spectra may be used.

When a chemiluminescent detectable label is used, after the addition of the at least one basic solution, hydrogen peroxide source, and the detectable label to the test sample, a detectable signal, namely, a chemiluminescent signal, is generated. The signal generated by the mixture is detected for a fixed duration of time. Preferably, the mixture is formed and the signal is detected concurrently. The duration of the detection may range from about 0.01 to about 360 seconds, more preferably from about 0.1 to about 30 seconds, and most preferably from about 0.5 to about 5 seconds. Chemiluminescent signals generated can be detected using routine techniques known to those skilled in the art.

Thus, in a chemiluminescent immunoassay according to the present disclosure, a chemiluminescent detectable label is used and added to the test sample, the chemiluminescent signal generated after the addition of the basic solution and the detectable label indicates the presence of each cardiac myocyte antigen $a^{n'}$ in the test sample, which signal can be detected. The amount or concentration of each cardiac myocyte antigen $a_n$ in the test sample can be quantified based on the intensity of the signal generated. Specifically, for each cardiac myocyte antigen $a^{n'}$, the amount of cardiac myocyte antigen $a^{n'}$ contained in a test sample is proportional to the intensity of the signal generated. Specifically, the amount of cardiac myocyte antigen $a^{n'}$ present can be quantified based on comparing the amount of light generated to a standard curve for the cardiac myocyte antigen $a^{n'}$ or by comparison to a reference standard specific to the cardiac myocyte antigen $a^{n'}$. Each of such reference standards may comprise, for example, an anti-idiotypic antibody. Each reference standard may comprise for example a derivatized cardiac myocyte antigen, such as for example a cardiac myocyte antigen derivatized with a polyethylene glycol. For example a suitable reference standard for cardiac troponin-I is a derivatized cardiac troponin-I such as cardiac troponin-I derivatized with a polyethylene glycol. Similarly, a suitable reference standard for cardiac troponin-T is a derivatized cardiac troponin-T such as cardiac troponin-T derivatized with a polyethylene glycol. It will be understood that other cardiac myocyte antigens as described elsewhere herein are also readily derivatized to obtain appropriate reference standards depending on the cardiac myocyte antigens selected for the immunoassay. Suitable standard curves for each cardiac myocyte antigen can be generated using serial dilutions, or solutions of cardiac myocyte antigens of known concentration, by mass spectroscopy, gravimetrically and by other techniques known in the art.

Fluorescence Polarization Immunoassay (FPIA): In an exemplary embodiment, a fluorescent label is employed in a fluorescence polarization immunoassay (FPIA) according to the invention. Generally, fluorescent polarization techniques are based on the principle that a fluorescent label, when excited by plane-polarized light of a characteristic wavelength, will emit light at another characteristic wavelength (i.e., fluorescence) that retains a degree of the polarization relative to the incident light that is inversely related to the rate of rotation of the label in a given medium. As a consequence of this property, a label with constrained rotation, such as one bound to another solution component with a relatively lower rate of rotation, will retain a relatively greater degree of polarization of emitted light than when free in solution.

This technique can be employed in immunoassays according to the invention, for example, by selecting reagents such that binding of the fluorescently labeled entities forms a complex sufficiently different in size such that a change in the intensity light emitted in a given plane can be detected. For example, when a labeled cardiac troponin antibody is bound by one or more cardiac troponin antigens captured by the capture antibody and/or autoantibodies reactive with the cardiac troponin, the resulting complex is sufficiently larger, and its rotation is sufficiently constrained, relative to the free labeled cardiac troponin antibody that binding is easily detected.

Fluorophores useful in FPIA include fluorescein, aminofluorescein, carboxyfluorescein, and the like, preferably 5 and 6-aminomethylfluorescein, 5 and 6-aminofluorescein, 6-carboxyfluorescein, 5-carboxyfluorescein, thioureafluorescein, and methoxytriazinolyl-aminofluorescein, and similar fluorescent derivatives. Examples of commercially available automated instruments with which fluorescence polarization assays can be conducted include: the IMx system, the TDx system, and TDxFLx system (all available from Abbott Laboratories, Abbott Park, Ill.).

Scanning Probe Microscopy (SPM): The use of scanning probe microscopy (SPM) for immunoassays also is a technology to which the immunoassay methods of the present disclosure are easily adaptable. In SPM, in particular in atomic force microscopy, the capture antibody is affixed to the solid phase that in addition to being capable of binding autoantibodies, has a surface suitable for scanning. An antibody $A_{a^{n''}}$, for example, can be adsorbed to a plastic or metal surface. Alternatively, an antibody $A_n$ can be covalently attached to, e.g., derivatized plastic, metal, silicon, or glass according to methods known to those of ordinary skill in the art. Following attachment of the antibody $A_{a^{n''}}$, the test sample is contacted with the solid phase, and a scanning probe microscope is used to detect and quantify solid phase-affixed complexes. The use of SPM eliminates the need for labels that are typically employed in immunoassay systems. Such a system is described in U.S. application Ser. No. 662,147, which is incorporated herein by reference.

MicroElectroMechanical Systems (MEMS): Immunoassays according to the present disclosure can also be carried out using a MicroElectroMechanical System (MEMS). MEMS are microscopic structures integrated onto silicon that combine mechanical, optical, and fluidic elements with electronics, allowing convenient detection of an analyte of interest. An exemplary MEMS device suitable for use in the present disclosure is the Protiveris' multicantilever array. This array is based on chemo-mechanical actuation of specially designed silicon microcantilevers and subsequent optical detection of the microcantilever deflections. When coated on one side with a binding partner, a microcantilever will bend when it is exposed to a solution containing the complementary molecule. This bending is caused by the change in the surface energy due to the binding event. Optical detection of the degree of bending (deflection) allows measurement of the amount of complementary molecule bound to the microcantilever.

Electrochemical Detection Systems: In other embodiments, immunoassays according to the present disclosure are carried out using electrochemical detection, the techniques for which are well known to those skilled in the art. Such electrochemical detection often employs one or more electrodes connected to a device that measures and records an electrical current. Such techniques can be realized in a number of commercially available devices, such as the I-STAT® (Abbott Laboratories, Abbott Park, Ill.) system, which comprises a hand-held electrochemical detection instrument and self-contained assay-specific reagent cartridges. For example, in the present invention, the basic trigger solution could be contained in the self-contained hemoglobin reagent cartridge and upon addition of the test sample, a current would be generated at least one electrode that is proportional to the amount of hemoglobin in the test sample. A basic procedure for electrochemical detection has been described for example by Heineman and coworkers. This entailed immobilization of a primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol ($PAP_R$, the "R" is intended to distinguish the reduced form from the oxidized form, $PAP_O$, the quinoneimine), which is electrochemically reversible at potentials that do not interfere with reduction of oxygen and water at pH 9.0, where AP exhibits optimum activity. $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in microelectrochemical immunoassays using PAPP volumes ranging from 20 µl to 360 µL have been reported previously. In capillary immunoassays with electrochemical detection, the lowest detection limit reported thus far is 3000 molecules of mouse IgG using a volume of 70 µL and a 30 min or 25 min assay time.

In an exemplary embodiment employing electrochemical detection according to the present disclosure, an antibody $A_{a''}{}^n$ reactive with a cardiac myocyte antigen $a_n$ can be immobilized on the surface of an electrode which is the solid phase. The electrode is then contacted with a test sample from, e.g., a human. Any analyte in the sample binds to the antibody $A_n$ to form a first solid phase-affixed complex. Autoantibodies also bind to the surface of the electrode thereby becoming immobilized on the surface of the electrode. Analyte in the test sample that is unbound by the capture antibody $A_{a''}{}^n$ binds to immobilized autoantibodies that are reactive with the analyte to form a second solid phase-affixed complex. These solid phase-affixed complexes are contacted with an antibody $B_{a''}{}^n$ that is also analyte-specific and has a detectable label. Formation of an immunodetection complex including $A_{a''}{}^n$-$a^{n'}$-$B_{a''}{}^n$ plus the autoantibody-$a^{n'}$-$B_{a''}{}^n$ complex results in generation of a signal by the detectable label, which is then detected.

Various electrochemical detection systems are described in U.S. Pat. No. 7,045,364 (issued May 16, 2006; incorporated herein by reference), U.S. Pat. No. 7,045,310 (issued May 16, 2006; incorporated herein by reference), U.S. Pat. No. 6,887,714 (issued May 3, 2005; incorporated herein by reference), U.S. Pat. No. 6,682,648 (issued Jan. 27, 2004; incorporated herein by reference); U.S. Pat. No. 6,670,115 (issued Dec. 30, 2003; incorporated herein by reference).

C. Kits

The present disclosure also provides kits for assaying test samples for presence of cardiac myocyte antigens, wherein the test sample may contain other substances that interfere with immunodetection of the cardiac myocyte antigens. Kits according to the present disclosure include one or more reagents useful for practicing one or more immunoassays according to the present disclosure. A kit generally includes a package with one or more containers holding the reagents, as one or more separate compositions or, optionally, as admixture where the compatibility of the reagents will allow. The test kit can also include other material(s), which may be desirable from a user standpoint, such as a buffer(s), a diluent(s), a standard(s), and/or any other material useful in sample processing, washing, or conducting any other step of the assay.

In certain embodiments, a test kit includes humanized monoclonal antibody or antibodies wherein each humanized monoclonal antibody is specific for a selected cardiac myocyte antigens $a_n$. This component can be used as a positive control in immunoassays according to the invention. If desired, this component can be included in the test kit in multiple concentrations to facilitate the generation of a standard curve to which the signal detected in the test sample can be compared. Alternatively, a standard curve can be generated by preparing dilutions of a single humanized monoclonal antibody solution provided in the kit.

Kits according to the present disclosure can include one or more antibodies $A_{a''}{}^n$, each $A_{a''}{}^n$ of which binds to at least one epitope on a cardiac myocyte antigen $a^{n'}$, and one or more detection antibodies $B_{a''}{}^n$, each $B_{a''}{}^n$ of which binds to at least one epitope on the cardiac myocyte antigen $a_n$ that is different from any epitope to which $A_{a''}{}^n$ binds, and instructions for detecting or quantifying each cardiac myocyte antigen $a^{n'}$. In certain embodiments test kits according to the present disclosure may include the solid phase, to which the antibodies $A_{a''}{}^n$ and/or antibodies $B_{a''}{}^n$ are bound. The solid phase may be a material such as a magnetic particle, a bead, a test tube, a microtiter plate, a cuvette, a membrane, a scaffolding molecule, a quartz crystal, a film, a filter paper, a disc or a chip.

Test kits according to the present disclosure can include for example one or more non-human monoclonal antibodies, each against a cardiac myocyte antigen $a^{n'}$, as antibodies $A_{a''}{}^n$ and antibodies $B_{a''}{}^n$. The kit may also include one or more detectable labels that can be or is conjugated to each antibody $B_{a''}{}^n$. In certain embodiments, the test kit includes at least one direct label, which may be an enzyme, oligonucleotide, nanoparticle chemiluminophore, fluorophore, fluorescence quencher, chemiluminescence quencher, or biotin. In some embodiments, the direct label is an acridinium compound such as an acridinium-9-carboxamide according to formula I:

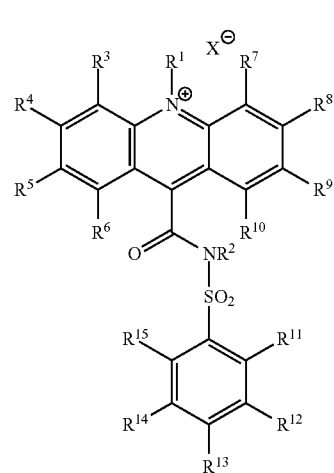

wherein R1 and R2 are each independently selected from the group consisting of: alkyl, alkenyl, alkynyl, aryl or aralkyl, sulfoalkyl, carboxyalkyl and oxoalkyl, and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\ominus}$ is an anion.

Alternatively, the acridinium compound can be an acridinium-9-carboxylate aryl ester having a structure according to formula II:

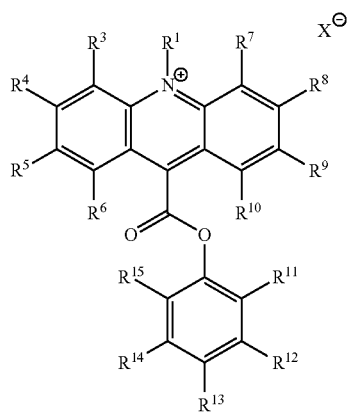

wherein R1 is an alkyl, alkenyl, alkynyl, aryl or aralkyl, sulfoalkyl, carboxyalkyl and oxoalkyl; and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\ominus}$ is an anion.

Test kits according to the present disclosure and which include an acridinium compound can also include a basic solution. For example, the basic solution can be a solution having a pH of at least about 10.

In certain embodiments, test kits according to the present disclosure may further include a hydrogen peroxide source, such as a buffer solution, a solution containing hydrogen peroxide, or a hydrogen peroxide generating enzyme. For example, test kits may include an amount of a hydrogen peroxide generating enzymes selected from the following: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

Test kits according to the present disclosure preferably include instructions for carrying out one or more of the immunoassays of the invention. Instructions included in kits of the present disclosure can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

D. Adaptations of the Methods of the Present Disclosure

The present disclosure is for example applicable to the jointly owned commercial Abbott Point of Care (i-STAT™) electrochemical immunoassay system which performs sandwich immunoassays for several cardiac markers, including TnI, CKMB and BNP. Immunosensors and ways of operating them in single-use test devices are described in jointly owned Publication Nos. US 20030170881, US 20040018577, US 20050054078, and US 20060160164, each of which is incorporated herein by reference. Additional background on the manufacture of electrochemical and other types of immunosensors is found in jointly owned U.S. Pat. No. 5,063,081 which is also incorporated by reference.

By way of example, and not of limitation, examples of the present invention shall now be given.

Example 1

Detection Antibody Conjugates

General Conjugation Procedure: The detection antibody was dissolved in a conjugation buffer (100 mM sodium phosphate, 150 mM NaCl, pH 8.0) to give a concentration of 1-10 mg/mL (6.25-62.5 µM). Acridinium, 9-[[[4-[(2,5-dioxo-1-pyrrolidinyl)oxy]-4-oxobutyl][(4-methylphenyl)sulfonyl]amino]carbonyl]-10-(3-sulfopropyl)-, inner salt, 2 (Adamczyk, M.; Chen, Y.-Y.; Mattingly, P. G.; Pan, Y. *J. Org. Chem.* 1998, 63, 5636-5639.) labeling reagent was prepared in N,N-dimethylformamide (DMF) at a concentration of 1-50 mM, as shown in formula 2 below:

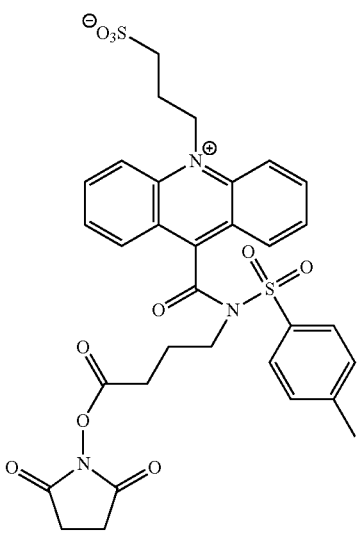

The selected antibody was treated with the acridinium-labeling reagent in a molar excess of 1-35 fold for 3-14 h at ambient temperature in the dark. Afterwards, the acridinium-9-carboxamide-antibody conjugate solution was dialyzed at ambient temperature over 20 h using a 10 kilodalton molecular weight cutoff membrane against three volumes (1000× conjugate solution volume) of a dialysis buffer consisting of 10 mM phosphate buffered saline (PBS) containing 0.1% CHAPS (3-[(3-cholamidopropyl)dimethylammonio]-1-propanesulfonate).

The acridinium-9-carboxamide-antibody conjugate was analyzed by UV absorbance at 280/369 nm to determine the incorporation ratio (IR) of the acridinium-9-carboxamide label to the protein calculated according to the formula:

$$IR = A369/\epsilon 369 / ([A280 - (A369/4.1)]/\epsilon 280)$$

where:

A280 and A369 are absorbance values obtained from the UV-visible spectrum of the conjugate;

4.1 is the ~A369/A280 ratio for an acridinium-9-carboxamide label;

$\epsilon 280$ is the extinction coefficient for an antibody at 280 nm (i.e., for IgG mAb $\epsilon 280 = 210,000$ $M^{-1}$ $cm^{-1}$); and $\epsilon 369$ is the extinction coefficient for an acridinium-9-carboxamide label at 369 nm.

The average incorporation ratio for pooled fractions can range from 0.4-0.8× the molar excess of the acridinium-9-carboxamide labeling reagent used.

a) Murine anti-cardiac troponin-T 7G7 (Biodesign International/Meridian Life Sciences, Saco, Me.; cat no H86429M) mapped to epitope $cTnT_{60-70}$ was dialyzed against PBS to give a solution concentration of 0.35 mg/mL. After conjugation the calculated IR was 3.1.

b) Murine anti-cardiac troponin-T 7F4 (Fitzgerald Ind Intnl, Concord, Mass., cat no. 10R-T127C) mapped to epitope $cTnT_{61-70}$ was dialyzed against PBS to give a solution concentration of 0.469 mg/mL. After conjugation the calculated IR was 2.8.

c) Murine anti-cardiac troponin-T 1C11 (Fitzgerald Ind Intnl, Concord, Mass., cat no. 10R-T127D) mapped to epitope $cTnT_{95-181}$ was dialyzed against PBS to give a solution concentration of 0.469 mg/mL. After conjugation the calculated IR was 2.8.

d) Murine anti-cardiac troponin-T M8020207 (Fitzgerald Ind Intnl, Concord, Mass., cat no. 10R-T85D) mapped primarily to epitope cTnT $cTnT_{73-87}$ was dialyzed against PBS to give a solution concentration of 0.413 mg/mL. After conjugation the calculated IR was 4.1.

e) Murine anti-cardiac troponin-I 19C7 (HyTest, Turku, Finland, cat. no. 4T21) mapped to epitope $cTnI_{41-49}$. After conjugation the calculated IR was 2.2.

Example 2

Capture Antibodies on Magnetic Microparticles

Carboxy paramagnetic microparticles (5% solids, nominally 5 micron diameter, Polymer Labs, Varian, Inc. Amherst, Mass.) were diluted to a concentration of 1% solids in 2-(N-morpholino)ethanesulfonic acid buffer (MES, 2 mL, pH 6.2, 50 mM) then washed with MES buffer (3×, 2 mL), and finally, resuspended in MES (2 mL). The particles were activated by mixing with 1-ethyl-3-[3-dimethylaminopropyl]carbodiimide hydrochloride (20 µL of 11 mg/1.129 mL in water) for 20 min, then washed (MES, 2 mL) and re-suspended in MES (2 mL). Murine anti-cardiac troponin-T 1C11 (Fitzgerald Ind Intnl, Concord, Mass., cat no. 10R-T127D) was added to the suspension at 60 µg/mL. After mixing for 60 min the antigen coated particles were magnetically sequestered, and the antigen solution was replaced with a blocking solution consisting of 1% BSA in PBS (2 mL). After mixing for 30 min, the particles were washed with 1% BSA in PBS (3×, 2 mL) and finally, resuspended in 1% BSA in PBS (2 mL) and adjusted to a final concentration of 1% solids.

Microparticles were similarly prepared with the following murine anti-cardiac troponin-T antibodies: 7G7 (Biodesign International/Meridian Life Sciences, Saco, Me.; cat no H86429M); 7F4 (Fitzgerald Ind Intnl, Concord, Mass., cat no. 10R-T127C); and M8020207 ("M80", Fitzgerald Ind Intnl, Concord, Mass., cat no. 10R-T85D).

Microparticles were similarly prepared with a mixture of the following murine anti-cardiac troponin-I antibodies: 8E10 (HyTest, Turku, Finland, cat. no. 4T21; cat no 4T21) mapped to epitope $cTnI_{86-92}$ and MO6 (Strategic Biosolutions, Inc, Newark, Del., cat no. D2440M406-MA).

Example 3

Chemiluminescent Immunoassay Cardiac Troponin-T Dose-Response for Combinations of Capture and Detection Antibodies A working suspension of each capture antibody microparticles prepared in Example 2 was prepared by dilution of the stock suspension to 0.05% solids in MES buffer (20 mM, pH 6.6) containing sucrose (13.6%) and antimicrobial agents. A working solution of each detection antibody conjugate was prepared by dilution of the stock solution to 10 ng/mL. Cardiac troponin-T (Biospacific, cat no. J34510359) standard solutions were prepared at 0, 0.25, 0.5, 1.0 and 2.0 µg/mL.

The assays were carried out on an ARCHITECT® i2000 instrument (Abbott Laboratories, Abbott Park, Ill.). Briefly, the cardiac troponin-T standard solution (10 µL) was diluted with ARCHITECT® PreIncubation Diluent (50 µL) and the capture antibody microparticles (50 µL) and incubated in the instrument reaction vessel. Following incubation, the microparticles were magnetically sequestered and washed with ARCHITECT® wash buffer. The detection antibody solution (50 µL) was added, the suspension incubated, and then the microparticles were washed again. ARCHITECT® pre-trigger solution containing hydrogen peroxide and ARCHITECT® trigger solution containing sodium hydroxide were then sequentially added and the chemiluminescent signal (relative light units, RLU) were recorded.

The dose-response curves for combinations of capture and detection antibodies are shown in Table 1 and graphically in FIG. 1.

TABLE 1

| Troponin-T (μg/mL) | Detection conjugate/capture antibody (RLU) | | | | | | | | |
|---|---|---|---|---|---|---|---|---|---|
| | 7G7/ 7F4 | 7G7/ M8020207 | 7G7/ 1C11 | 7F4/ 7G7 | 7F4/ M8020207 | 7F4/ 1C11 | M8020207/ 7G7 | M8020207/ 7F4 | M8020207/ 1C11 |
| 2 | 46829 | 305420 | 310518 | 6870 | 184343 | 185886 | 137713 | 100426 | 202062 |
| 1 | 29877 | 250755 | 238464 | 1469 | 136026 | 127325 | 106585 | 71224 | 157435 |
| 0.5 | 17246 | 163605 | 148894 | 618 | 82486 | 63012 | 70107 | 45245 | 105484 |
| 0.25 | 9081 | 96153 | 79374 | 452 | 38363 | 26439 | 42508 | 25611 | 66447 |
| 0 | 333 | 338 | 317 | 269 | 297 | 256 | 367 | 379 | 368 |

Example 4

Epitope Mapping of Autoantibodies to Cardiac Troponin-T

Antibodies were screened against a biotinylated peptide library (Table 2) covering the entire cTnT amino acid sequence as shown in FIG. 2 (UniProtKB/Swiss-Prot P45379 (TNNT2_HUMAN), initiator methionine removed, 297 aa, SEQ ID NO: 96), each peptide length, 15 aa; overlap, 12 aa; PEPscreen®, Sigma-Genosys, The Woodlands, Tex.) on streptavidin-coated microplates (Reacti-Bind™, Streptavidin; Pierce, Rockford, Ill.).

Figure 3:
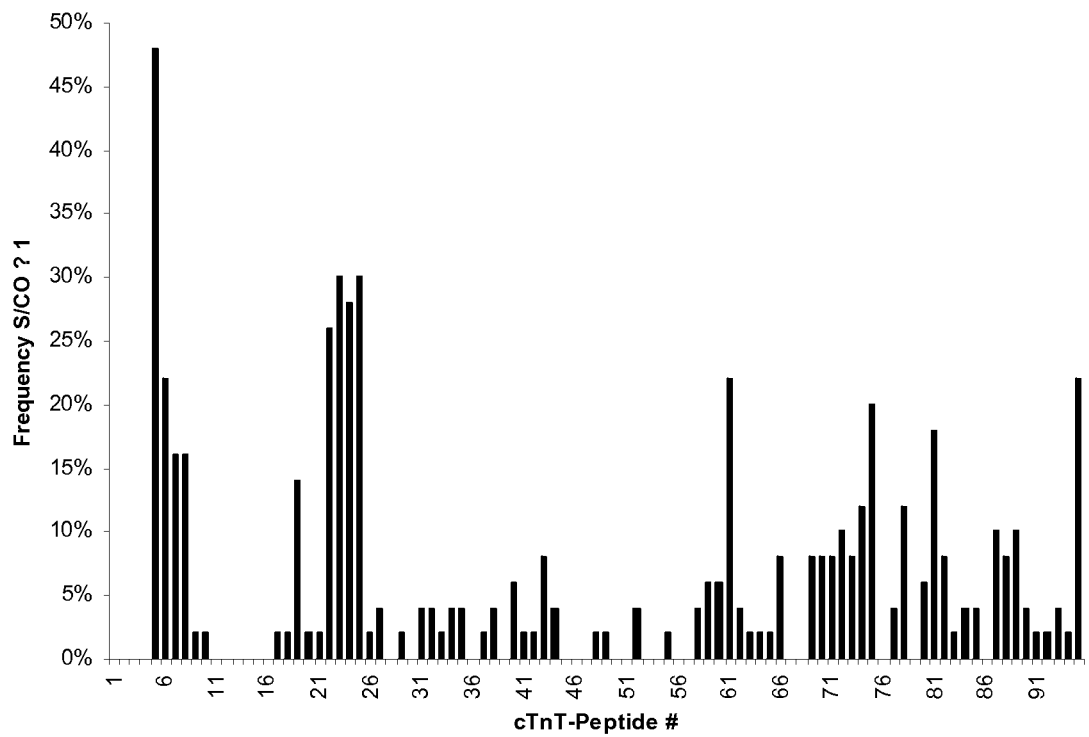
FIG. 3 is a frequency plot of cTnT autoantibody epitopes.

Thus, the peptides (100 μL, 1200 pmol/mL) were arrayed on the microplate; the microplate was then sealed and incubated/mixed for 1 h at ambient temperature. The microplate was then washed with ARCHITECT® wash buffer and aspirated to dryness. Samples (500 μL) were diluted with 9.5 mL of Axsym Troponin Preincubation diluent then arrayed (100 μL/well) to the microplates with the peptide library. The plates were sealed and incubated at 37° C., mixing at 28 rpm for 2 h. Afterwards the plates were washed with ARCHITECT® wash buffer and the response against each peptide was determined using chemiluminescent detection on a Berthold Mithras microplate reader (Berthold Technologies Inc, Oak Ridge, Tenn.). A mouse anti-human IgG acridinium labeled conjugate solution (100 μL) was added to each test well. After the conjugate was added to all test samples, the microplate was then sealed, placed on an orbital shaker at 28 rpm and incubated at 37° C. for 1 h. The conjugate solution was then removed and the wells of the microplate were washed with the ARCHITECT® Line Diluent (3×300 μL). The microplate was loaded into the instrument that had been equilibrated at 37° C. ARCHITECT® Pre-Trigger solution (100 μL) was dispensed to each well. After the pre-trigger solution was added, the plate was shaken for 72 s. Then the ARCHITECT® Trigger solution (100 μL) was dispensed to each well and chemiluminescent signal recorded for 2 s. FIG. 3 shows the frequency of reactive cardiac troponin-T epitopes found in human cardiac troponin-T autoantibodies.

TABLE 2 cTnT Antigen Peptide Library

| cTnT Peptide No. | SEQ. ID. NO. | cTnT sequence | AA position. |
|---|---|---|---|
| 1 | 1 | SDIEEVVEEYEEEEQ | 1-15 |
| 2 | 2 | EEVVEEYEEEEQEEA | 4-18 |
| 3 | 3 | VEEYEEEEQEEAAVE | 7-21 |
| 4 | 4 | YEEEEQEEAAVEEEE | 10-24 |
| 5 | 5 | EEQEEAAVEEEEDWR | 13-27 |
| 6 | 6 | EEAAVEEEEDWREDE | 16-30 |
| 7 | 7 | AVEEEEDWREDEDEQ | 19-33 |
| 8 | 8 | EEEDWREDEDEQEEA | 22-36 |
| 9 | 9 | DWREDEDEQEEAAEE | 25-39 |
| 10 | 10 | EDEDEQEEAAEEDAE | 28-42 |
| 11 | 11 | DEQEEAAEEDAEAEA | 31-45 |
| 12 | 12 | EEAAEEDAEAEAETE | 34-48 |
| 13 | 13 | AEEDAEAEAETEETR | 37-51 |
| 14 | 14 | DAEAEAETEETRAEE | 40-54 |
| 15 | 15 | AEAETEETRAEEDEE | 43-57 |
| 16 | 16 | ETEETRAEEDEEEEE | 46-60 |
| 17 | 17 | ETRAEEDEEEEEAKE | 49-63 |
| 18 | 18 | AEEDEEEEAKEAED | 52-66 |
| 19 | 19 | DEEEEEAKEAEDGPM | 55-69 |
| 20 | 20 | EEEAKEAEDGPMEES | 58-72 |
| 21 | 21 | AKEAEDGPMEESKPK | 61-75 |
| 22 | 22 | AEDGPMEESKPKPRS | 64-78 |
| 23 | 23 | GPMEESKPKPRSFMP | 67-81 |
| 24 | 24 | EESKPKPRSFMPNLV | 70-84 |
| 25 | 25 | KPKPRSFMPNLVPPK | 73-87 |
| 26 | 26 | PRSFMPNLVPPKIPD | 76-90 |
| 27 | 27 | FMPNLVPPKIPDGER | 79-93 |
| 28 | 28 | NLVPPKIPDGERVDF | 82-96 |
| 29 | 29 | PPKIPDGERVDFDDI | 85-99 |
| 30 | 30 | IPDGERVDFDDIHRK | 88-102 |
| 31 | 31 | GERVDFDDIHRKRME | 91-105 |
| 32 | 32 | VDFDDIHRKRMEKDL | 94-108 |
| 33 | 33 | DDIHRKRMEKDLNEL | 97-111 |

TABLE 2-continued cTnT Antigen Peptide Library

| cTnT Peptide No. | SEQ. ID. NO. | cTnT sequence | AA position. |
|---|---|---|---|
| 34 | 34 | HRKRMEKDLNELQAL | 100-114 |
| 35 | 35 | RMEKDLNELQALIEA | 103-117 |
| 36 | 36 | KDLNELQALIEAHFE | 106-120 |
| 37 | 37 | NELQALIEAHFENRK | 109-123 |
| 38 | 38 | QALIEAHFENRKKEE | 112-126 |
| 39 | 39 | IEAHFENRKKEEEEL | 115-129 |
| 40 | 40 | HFENRKKEEEELVSL | 118-132 |
| 41 | 41 | NRKKEEEELVSLKDR | 121-135 |
| 42 | 42 | KEEEELVSLKDRIER | 124-138 |
| 43 | 43 | EELVSLKDRIERRRA | 127-141 |
| 44 | 44 | VSLKDRIERRRAERA | 130-144 |
| 45 | 45 | KDRIERRRAERAEQQ | 133-147 |
| 46 | 46 | IERRRAERAEQQRIR | 136-150 |
| 47 | 47 | RRAERAEQQRIRNER | 139-153 |
| 48 | 48 | ERAEQQRIRNEREKE | 142-156 |
| 49 | 49 | EQQRIRNEREKERQN | 145-159 |
| 50 | 50 | RIRNEREKERQNRLA | 148-162 |
| 51 | 51 | NEREKERQNRLAEER | 151-165 |
| 52 | 52 | EKERQNRLAEERARR | 154-168 |
| 53 | 53 | RQNRLAEERARREEE | 157-171 |
| 54 | 54 | RLAEERARREEEENR | 160-174 |
| 55 | 55 | EERARREEEENRRKA | 163-177 |
| 56 | 56 | ARREEEENRRKAEDE | 166-180 |
| 57 | 57 | EEEENRRKAEDEARK | 169-183 |
| 58 | 58 | ENRRKAEDEARKKKA | 172-186 |
| 59 | 59 | RKAEDEARKKKALSN | 175-189 |
| 60 | 60 | EDEARKKKALSNMMH | 178-192 |
| 61 | 61 | ARKKKALSNMMHFGG | 181-195 |
| 62 | 62 | KKALSNMMHFGGYIQ | 184-198 |
| 63 | 63 | LSNMMHFGGYIQKQA | 187-201 |
| 64 | 64 | MMHFGGYIQKQAQTE | 190-204 |
| 65 | 65 | FGGYIQKQAQTERKS | 193-207 |
| 66 | 66 | YIQKQAQTERKSGKR | 196-210 |
| 67 | 67 | KQAQTERKSGKRQTE | 199-213 |
| 68 | 68 | QTERKSGKRQTEREK | 202-216 |
| 69 | 69 | RKSGKRQTEREKKKK | 205-219 |
| 70 | 70 | GKRQTEREKKKKILA | 208-222 |
| 71 | 71 | QTEREKKKKILAERR | 211-225 |
| 72 | 72 | REKKKKILAERRKVL | 214-228 |
| 73 | 73 | KKKILAERRKVLAID | 217-231 |
| 74 | 74 | ILAERRKVLAIDHLN | 220-234 |
| 75 | 75 | ERRKVLAIDHLNEDQ | 223-237 |
| 76 | 76 | KVLAIDHLNEDQLRE | 226-240 |
| 77 | 77 | AIDHLNEDQLREKAK | 229-243 |
| 78 | 78 | HLNEDQLREKAKELW | 232-246 |
| 79 | 79 | EDQLREKAKELWQSI | 235-249 |
| 80 | 80 | LREKAKELWQSIYNL | 238-252 |
| 81 | 81 | KAKELWQSIYNLEAE | 241-255 |
| 82 | 82 | ELWQSIYNLEAEKFD | 244-258 |
| 83 | 83 | QSIYNLEAEKFDLQE | 247-261 |
| 84 | 84 | YNLEAEKFDLQEKFK | 250-264 |
| 85 | 85 | EAEKFDLQEKFKQQK | 253-267 |
| 86 | 86 | KFDLQEKFKQQKYEI | 256-270 |
| 87 | 87 | LQEKFKQQKYEINVL | 259-273 |
| 88 | 88 | KFKQQKYEINVLRNR | 262-276 |
| 89 | 89 | QQKYEINVLRNRIND | 265-279 |
| 90 | 90 | YEINVLRNRINDNQK | 268-282 |
| 91 | 91 | NVLRNRINDNQKVSK | 271-285 |
| 92 | 92 | RNRINDNQKVSKTRG | 274-288 |
| 93 | 93 | INDNQKVSKTRGKAK | 277-291 |
| 94 | 94 | NQKVSKTRGKAKVTG | 280-294 |
| 95 | 95 | VSKTRGKAKVTGRWK | 283-297 |

Example 5

Epitope Mapping of Monoclonal Antibodies to Cardiac Troponin-T

Murine anti-cardiac troponin-T M8020207 acridinium-9-carboxyamide conjugate from Example 1 was screened against a biotinylated peptide library (Table 2, Example 4). The conjugate was diluted to 100 ng/mL then the conjugate solution (100 μL) was added to each test well. After the conjugate was added, the microplate was then sealed, placed on an orbital shaker at 28 rpm and incubated at 37° C. for 1 h. The conjugate solution was then removed and the wells of the microplate were washed with the ARCHITECT® Line Diluent (3×300 μL). The microplate was loaded into the instrument that had been equilibrated at 37° C. ARCHITECT® Pre-Trigger solution (100 μL) was dispensed to each well.

Figure 4:
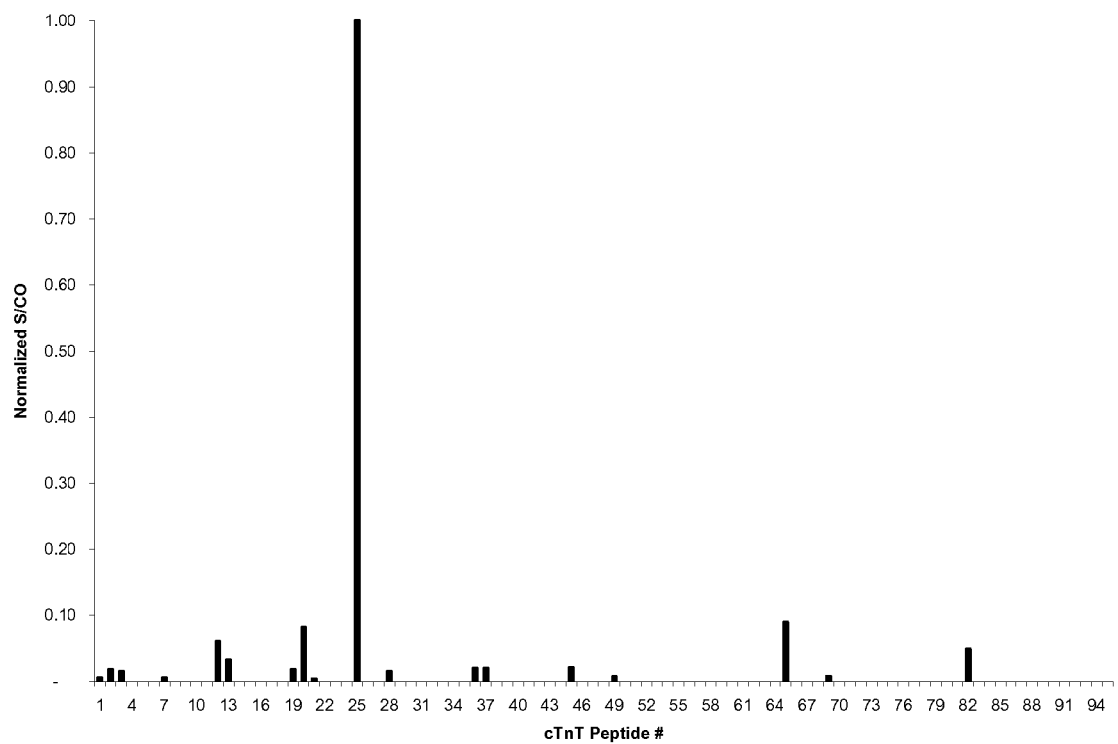
FIG. 4 is an epitope map of murine anti-cardiac troponin-T M8020207.

After the pre-trigger solution was added, the plate was shaken for 72 s. Then the ARCHITECT® Trigger solution (100 µL) was dispensed to each well and chemiluminescent signal recorded for 2 s. As shown in FIG. 4, the primary response was to peptide 25 corresponding to $cTnT_{73-87}$.

Figure 5:
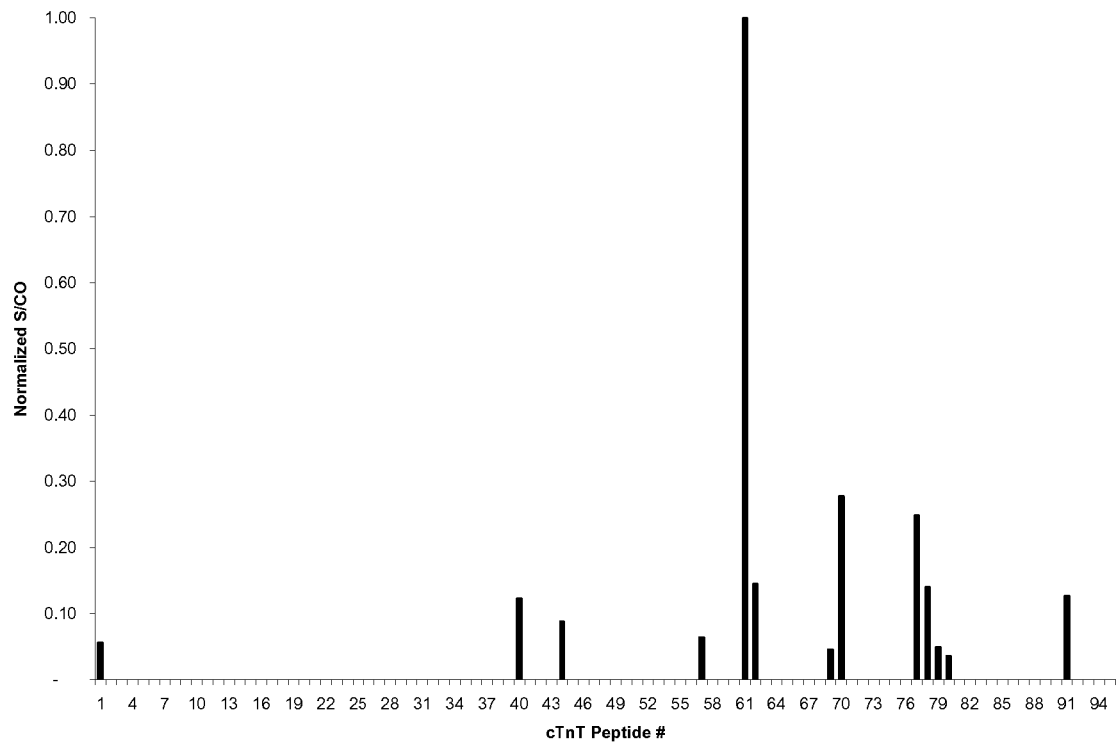
FIG. 5 is an epitope map of murine anti-cardiac troponin-T 1C11.

Murine anti-cardiac troponin-T 1C11 from Example 1 was screened against a biotinylated peptide library (Table 2, Example 4). The antibody was diluted to 100 ng/mL, then 100 µL was added to each test well. The plate was sealed and incubated at 37° C., mixing at 28 rpm for 2 h. Afterwards the plates were washed with ARCHITECT® wash buffer. A goat anti-mouse IgG acridinium labeled conjugate solution (100 µL) was added to each test well. After the conjugate was added to all test samples, the microplate was then sealed, placed on an orbital shaker at 28 rpm and incubated at 37° C. for 1 h. The conjugate solution was then removed and the wells of the microplate were washed with the ARCHITECT® Line Diluent (3×300 µL). The microplate was loaded into the instrument that had been equilibrated at 37° C. ARCHITECT® Pre-Trigger solution (100 µL) was dispensed to each well. After the pre-trigger solution was added, the plate was shaken for 72 s. Then the ARCHITECT® Trigger solution (100 µL) was dispensed to each well and chemiluminescent signal recorded for 2 s. As shown in FIG. 5, the primary epitopic response was to peptide 61 corresponding to $cTnT_{181-195}$.

Example 6

Standard Curve for Cardiac Troponin-T

Murine anti-cardiac troponin-T M8020207 coated microparticles from Example 2 were diluted to 0.3% solids. Murine anti-cardiac troponin-T 7G7 acridinium-9-carboxyamide conjugate from Example 1 was diluted to 30 ng/mL. Standard solutions were made from human cardiac troponin-I-T-C complex (HyTest, Turku Finland, catalog no. 8T62) to give cTnT concentrations: 0, 7.0, 13.0, 40.0, and 269.0 pM. Three test samples were prepared by spiking hcTnITC into negative human plasma to give nominal cTnT concentrations of 0, 7.0 and 40 pM.

The standard solutions and human plasma samples were analyzed on an ARCHITECT® i2000 as in Example 3. A point-to-point calibration curve was plotted (RLU vs cTnT concentration). The results are listed in Table 3.

TABLE 3

Magnetic microparticle cardiac troponin T assay results

| Sample | RLU | pM cTnT |
|---|---|---|
| Cal A | 2,369 | 0 |
| Cal B | 15,275 | 7 |
| Cal C | 28,071 | 14 |
| Cal D | 81,462 | 42 |
| Cal E | 422,814 | 279 |
| Negative plasma | 2,074 | #N/A |
| Spiked plasma @7 pM | 13,788 | 6.18 |
| Spiked plasma @42 pM | 74,126 | 38.07 |

Example 7

Epitope Mapping of Autoantibodies to Cardiac Troponin-I

Figure 7:
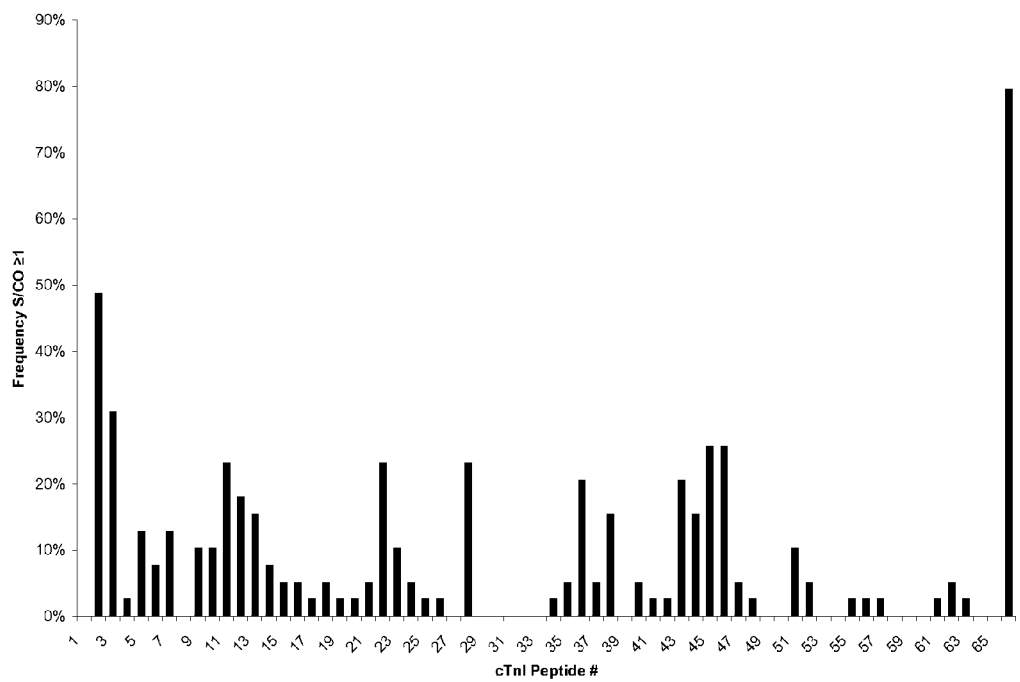
FIG. 7 shows the frequency of reactive cardiac troponin-I epitopes found in human cardiac troponin-I autoantibodies.

Antibodies were screened against a biotinylated peptide library (Table 4) covering the entire cTnI amino acid sequence as shown in FIG. 6 (UniProtKB/Swiss-Prot P19429-1 (TNNI3_HUMAN), initiator methionine removed, 209 aa, SEQ ID NO: 97) peptide length, 15 aa; overlap, 12 aa; PEPscreen®, Sigma-Genosys, The Woodlands, Tex.) on streptavidin-coated microplates (Reacti-Bind™, Streptavidin; Pierce, Rockford, Ill.). Thus, the peptides (100 µL, 1200 pmol/mL) were arrayed on the microplate; the microplate was then sealed and incubated/mixed for 1 h at ambient temperature. The microplate was then washed with ARCHITECT® wash buffer and aspirated to dryness. Samples (500 µL) were diluted with 9.5 mL of Axsym Troponin Preincubation diluent then arrayed (100 µL/well) to the microplates with the peptide library. The plates were sealed and incubated at 37° C., mixing at 28 rpm for 2 h. Afterwards the plates were washed with ARCHITECT® wash buffer and the response against each peptide was determined using chemiluminescent detection on a Berthold Mithras microplate reader (Berthold Technologies Inc, Oak Ridge, Tenn.). A mouse anti-human IgG acridinium labeled conjugate solution (100 µL) was added to each test well. After the conjugate was added to all test samples, the microplate was then sealed, placed on an orbital shaker at 28 rpm and incubated at 37° C. for 1 h. The conjugate solution was then removed and the wells of the microplate were washed with the ARCHITECT® Line Diluent (3×300 µL). The microplate was loaded into the instrument that had been equilibrated at 37° C. ARCHITECT® Pre-Trigger solution (100 µL) was dispensed to each well. After the pre-trigger solution was added, the plate was shaken for 72 s. Then the ARCHITECT® Trigger solution (100 µL) was dispensed to each well and chemiluminescent signal recorded for 2 s. FIG. 7 shows the frequency of reactive cardiac troponin-I epitopes found in human cardiac troponin-I autoantibodies.

TABLE 4 cTnI Peptide Library

| cTnI Peptide No. | SEQ ID NO. | cTnI_Sequence | AA position |
|---|---|---|---|
| 1 | 98 | ADGSSDAAREPRPAP | 1-15 |
| 2 | 99 | SSDAAREPRPAPAPI | 4-18 |
| 3 | 100 | AAREPRPAPAPIRRR | 7-21 |
| 4 | 101 | EPRPAPAPIRRRSSN | 10-24 |
| 5 | 102 | PAPAPIRRRSSNYRA | 13-27 |
| 6 | 103 | APIRRRSSNYRAYAT | 16-30 |
| 7 | 104 | RRRSSNYRAYATEPH | 19-33 |
| 8 | 105 | SSNYRAYATEPHAKK | 22-36 |
| 9 | 106 | YRAYATEPHAKKKSK | 25-39 |
| 10 | 107 | YATEPHAKKKSKISA | 28-42 |
| 11 | 108 | EPHAKKKSKISASRK | 31-45 |
| 12 | 109 | AKKKSKISASRKLQL | 34-48 |
| 13 | 110 | KSKISASRKLQLKTL | 37-51 |
| 14 | 111 | ISASRKLQLKTLLLQ | 40-54 |
| 15 | 112 | SRKLQLKTLLLQIAK | 43-57 |
| 16 | 113 | LQLKTLLLQIAKQEL | 46-60 |

TABLE 4-continued cTnI Peptide Library

| cTnI Peptide No. | SEQ ID NO. | cTnI_Sequence | AA position |
|---|---|---|---|
| 17 | 114 | KTLLLQIAKQELERE | 49-63 |
| 18 | 115 | LLQIAKQELEREAEE | 52-66 |
| 19 | 116 | IAKQELEREAEERRG | 55-69 |
| 20 | 117 | QELEREAEERRGEKG | 58-72 |
| 21 | 118 | EREAEERRGEKGRAL | 61-75 |
| 22 | 119 | AEERRGEKGRALSTR | 64-78 |
| 23 | 120 | RRGEKGRALSTRCQP | 67-81 |
| 24 | 121 | EKGRALSTRCQPLEL | 70-84 |
| 25 | 122 | RALSTRCQPLELAGL | 73-87 |
| 26 | 123 | STRCQPLELAGLGFA | 76-90 |
| 27 | 124 | CQPLELAGLGFAELQ | 79-93 |
| 28 | 125 | LELAGLGFAELQDLC | 82-96 |
| 29 | 126 | AGLGFAELQDLCRQL | 85-99 |
| 30 | 127 | GFAELQDLCRQLHAR | 88-102 |
| 31 | 128 | ELQDLCRQLHARVDK | 91-105 |
| 32 | 129 | DLCRQLHARVDKVDE | 94-108 |
| 33 | 130 | RQLHARVDKVDEERY | 97-111 |
| 34 | 131 | HARVDKVDEERYDIE | 100-114 |
| 35 | 132 | VDKVDEERYDIEAKV | 103-117 |
| 36 | 133 | VDEERYDIEAKVTKN | 106-120 |
| 37 | 134 | ERYDIEAKVTKNITE | 109-123 |
| 38 | 135 | DIEAKVTKNITEIAD | 112-126 |
| 39 | 136 | AKVTKNITEIADLTQ | 115-129 |
| 40 | 137 | TKNITEIADLTQKIF | 118-132 |
| 41 | 138 | ITEIADLTQKIFDLR | 121-135 |
| 42 | 139 | IADLTQKIFDLRGKF | 124-138 |
| 43 | 140 | LTQKIFDLRGKFKRP | 127-141 |
| 44 | 141 | KIFDLRGKFKRPTLR | 130-144 |
| 45 | 142 | DLRGKFKRPTLRRVR | 133-147 |
| 46 | 143 | GKFKRPTLRRVRISA | 136-150 |
| 47 | 144 | KRPTLRRVRISADAM | 139-153 |
| 48 | 145 | TLRRVRISADAMMQA | 142-156 |
| 49 | 146 | RVRISADAMMQALLG | 145-159 |
| 50 | 147 | ISADAMMQALLGARA | 148-162 |
| 51 | 148 | DAMMQALLGARAKES | 151-165 |
| 52 | 149 | MQALLGARAKESLDL | 154-168 |
| 53 | 150 | LLGARAKESLDLRAH | 157-171 |
| 54 | 151 | ARAKESLDLRAHLKQ | 160-174 |
| 55 | 152 | KESLDLRAHLKQVKK | 163-177 |
| 56 | 153 | LDLRAHLKQVKKEDT | 166-180 |
| 57 | 154 | RAHLKQVKKEDTEKE | 169-183 |
| 58 | 155 | LKQVKKEDTEKENRE | 172-186 |
| 59 | 156 | VKKEDTEKENREVGD | 175-189 |
| 60 | 157 | EDTEKENREVGDWRK | 178-192 |
| 61 | 158 | EKENREVGDWRKNID | 181-195 |
| 62 | 159 | NREVGDWRKNIDALS | 184-198 |
| 63 | 160 | VGDWRKNIDALSGME | 187-201 |
| 64 | 161 | WRKNIDALSGMEGRK | 190-204 |
| 65 | 162 | NIDALSGMEGRKKKF | 193-207 |
| 66 | 163 | ALSGMEGRKKKFES | 196-209 |

Example 8

Epitope Mapping of Monoclonal Antibodies to Cardiac Troponin-I

Figure 8:
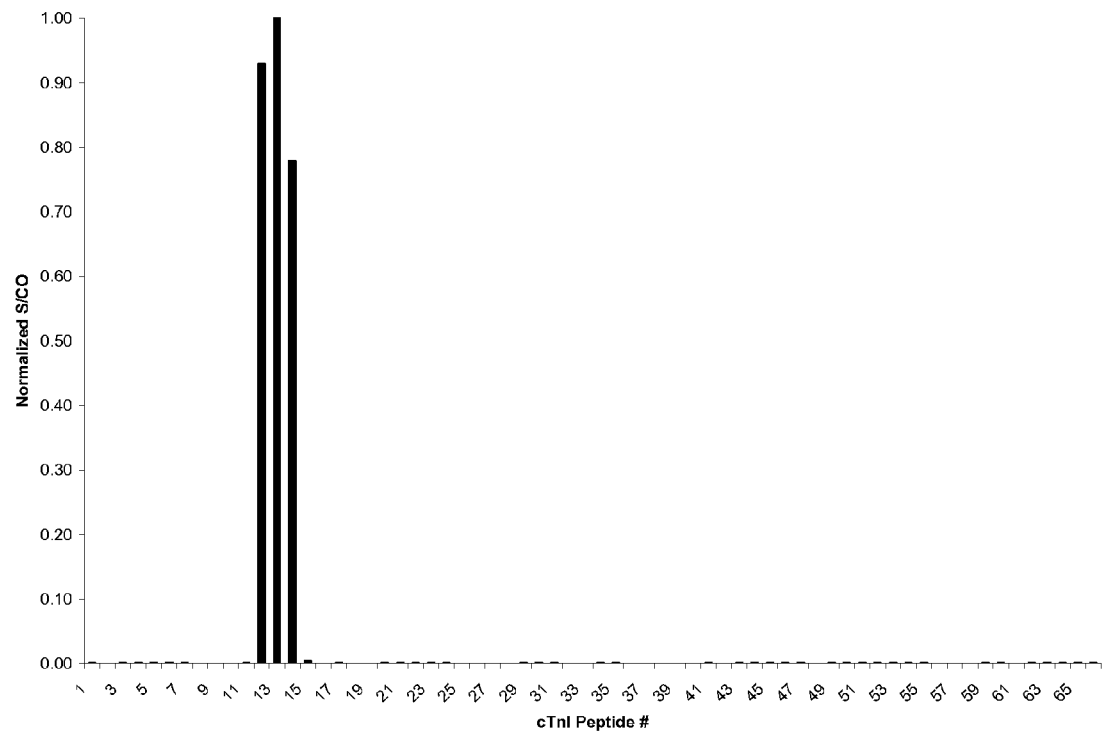
FIG. 8 is an epitope map of monoclonal 19C7.

Murine anti-cardiac troponin-I 19C7 acridinium-9-carboxamide conjugate from Example 1 was screened against a biotinylated peptide library (Example 7). The conjugate was diluted to 100 ng/mL then the conjugate solution (100 µL) was added to each test well. After the conjugate was added, the microplate was then sealed, placed on an orbital shaker at 28 rpm and incubated at 37° C. for 1 h. The conjugate solution was then removed and the wells of the microplate were washed with the ARCHITECT® Line Diluent (3×300 µL). The microplate was loaded into the instrument that had been equilibrated at 37° C. ARCHITECT® Pre-Trigger solution (100 µL) was dispensed to each well. After the pre-trigger solution was added, the plate was shaken for 72 s. Then the ARCHITECT® Trigger solution (100 µL) was dispensed to each well and chemiluminescent signal recorded for 2 s. As shown in FIG. 8, the primary response was to peptides 13-15 corresponding to $cTnI_{37-57}$ encompassing the epitope assignment from the vendor. (SEQ ID NOS: 110, 111 and 112).

Example 9

Standard Curve for Cardiac Troponin-I Assay

Murine anti-cardiac troponin-I 8E10/MO6 coated microparticles from Example 2 were diluted to 0.3% solids. Murine anti-cardiac troponin-I 19C7 acridinium-9-carboxamide conjugate from Example 1 was diluted to 30 ng/mL. Standard solutions were made from human cardiac troponin-I-T-C complex (HyTest, Turku Finland, catalog no. 8T62) to give cTnI concentrations: 0, 10.0, 21.0, 63.0, and 419.0 pM. Three test samples were prepared by spiking hcTnITC into negative human plasma to give nominal cTnI concentrations of 0, 10.0 and 63 pM. The standard solutions and human plasma samples were analyzed on an ARCHITECT® i2000 as in Example 3. A point-to-point calibration curve was plotted (RLU vs cTnI concentration). The results are listed in Table 5.

TABLE 5

Magnetic microparticle cardiac troponin-I assay results

| Sample | RLU | pM cTnI |
|---|---|---|
| Cal A | 449 | 0 |
| Cal B | 10,173 | 10 |
| Cal C | 20,244 | 21 |
| Cal D | 59,799 | 63 |
| Cal E | 377,720 | 419 |
| Negative plasma | 867 | 0.45 |
| Spike plasma @10 pM | 6,059 | 6.04 |
| Spike plasma @63 pM | 35,742 | 37.35 |

Example 10

Standard Curve for Cardiac Troponin Assay

Murine anti-cardiac troponin-I 8E10/MO6 coated microparticles and murine anti-cardiac troponin-T M8020207 coated microparticles from Example 2 were diluted 1:1 to a suspension of 0.3% solids. Murine anti-cardiac troponin-I 19C7 acridinium-9-carboxyamide conjugate and murine anti-cardiac troponin-T 7G7 acridinium-9-carboxyamide conjugate from Example 1 were diluted 1:1 to a solution of 30 ng/mL. Standard solutions were made from human cardiac troponin-I-T-C complex (HyTest, Turku Finland, catalog no. 8T62) to give cTn concentrations: 0, 17.0, 34.0, 103.0, and 687.0 pM. Three test samples were prepared by spiking hcTnITC into negative human plasma to give nominal cTn concentrations of 0, 17.0 and 103 pM. The standard solutions and human plasma samples were analyzed on an ARCHITECT® i2000 as in Example 3. A point-to-point calibration curve was plotted (RLU vs cTn concentration). The results are listed in Table 6.

TABLE 6

Magnetic microparticle cardiac troponins assay results

| Sample | RLU | pM cTn |
|---|---|---|
| Cal A | 13,623 | 0 |
| Cal B | 20,953 | 17 |
| Cal C | 45,617 | 34 |
| Cal D | 92,650 | 103 |

TABLE 6-continued

Magnetic microparticle cardiac troponins assay results

| Sample | RLU | pM cTn |
|---|---|---|
| Cal E | 465,222 | 687 |
| Negative plasma | 13,542 | #N/A |
| Spike plasma @17 pM | 30,008 | 23.50 |
| Spike plasma @103 pM | 92,899 | 103.51 |

One skilled in the art would readily appreciate that the immunoassays described in the present disclosure are well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The present disclosure illustratively described herein suitably may be practiced in the absence of any element or elements, limitation or limitations which are not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

It is to be understood that the foregoing description is intended to illustrate and not limit the scope of the invention. Other aspects, advantages, and modifications of the invention are within the intended scope of the claims set forth below.

What is claimed is:

1. An immunoassay for detecting cardiac myocyte damage in a subject from a test sample, the immunoassay comprising the steps of:
   a) contacting a test sample from a subject suspected of having cardiac myocyte damage with n antibodies ($A_{a'}^{n}$) that bind to at least n epitopes on n' cardiac myocyte antigens (a'') to form n' (n-antibody:antigen) immuno-complexes $(A_{a_1}^{1})(A_{a_1}^{2}) \ldots (A_{a_1}^{n})(a^{1})$, $(A_{a_2}^{1})(A_{a_2}^{2}) \ldots (A_{a_2}^{n})(a^{2}) \ldots (A_{a_{n'}}^{1})(A_{a_{n'}}^{2}) \ldots (A_{a_{n'}}^{n})(a^{n'})$ wherein n is an integer from 1 to 10; and n' is an integer from 2 to 10;
   b) contacting said mixture comprising n' (n-antibody:antigen) immuno-complexes with n'' antibodies ($B_{a'}^{n''}$) that bind to n'' epitopes on n' cardiac myocyte antigens (a'') to form n' ((n+n'') antibody:antigen) measurable assemblies $((A_{a_1}^{1})(A_{a_1}^{2}) \ldots (A_{a_1}^{n}))((B_{a_1}^{1})(B_{a_1}^{2}) \ldots (B_{a_1}^{n''})(a^{1})$, $((A_{a_2}^{1})(A_{a_2}^{2}) \ldots (A_{a_2}^{n}))((B_{a_2}^{1})(B_{a_2}^{2}) \ldots (B_{a_2}^{n''})(a^{2}), \ldots ((A_{a_{n'}}^{1})(A_{a_{n'}}^{2}) \ldots (A_{a_{n'}}^{n}))((B_{a_{n'}}^{1})(B_{a_{n'}}^{2}) \ldots (B_{a_{n'}}^{n''})(a^{n'})$ wherein n and n'' are independently an integer from 1 to 10, and n' is an integer from 2 to 10, and antibodies A and B bind to (n+n'') different epitopes of a cardiac myocyte antigen;
   c) measuring an optical, electrical, or change-of-state signal of at least two antibody:antigen measurable assemblies of the n' ((n+n') antibody:antigen) measurable assemblies $((A_{a_1}^{1})(A_{a_1}^{2}) \ldots (A_{a_1}^{n})((B_{a_1}^{1})(B_{a_1}^{2}) \ldots (B_{a_1}^{n''})(a^{1})$, $((A_{a_2}^{1})(A_{a_2}^{2}) \ldots (A_{a_2}^{n}))((B_{a_2}^{1})(B_{a_2}^{2}) \ldots (B_{a_2}^{n''}))(a^{2}), \ldots ((A_{a_{n'}}^{1})(A_{a_{n'}}^{2}) \ldots (A_{a_{n'}}^{n}))((B_{a_{n'}}^{1})(B_{a_{n'}}^{2}) \ldots (B_{a_{n'}}^{n''}))(a^{n'})$; and
   d) detecting cardiac myocyte damage by determining whether the measurement in step (c) exceeds a predetermined level, wherein each antibody $A_{a'}^{n}$ binds to at least one epitope on a cardiac myocyte antigen a'' that is different than any of the epitopes to which the antibodies $B_{a'}^{n''}$ bind.

2. The immunoassay of claim 1, wherein the cardiac myocyte antigens a''' are selected from the group consisting of cardiac troponin-I, cardiac troponin-T, creatine phosphokinase MB (CKMB), myoglobin, myosin heavy chain, myosin light chain, B-type natriuretic peptide (including pro-BNP, NT-proBNP, and hBNP(1-32)), heart fatty-acid-binding protein (H-FABP), placenta growth factor (PLGF), and interleukin-6 (IL-6).

3. The immunoassay of claim 1, wherein n'=2 and the cardiac myocyte antigens a''' are cardiac troponin-I (cTnI) and cardiac troponin-T (cTnT).

4. The immunoassay of claim 1 or 2, wherein the antibodies $A_{a'}^{n}$ antibodies $B_{a'}^{n''}$, or antibodies $A_{a'}^{n}$ and $B_{a'}^{n''}$ comprise humanized antibodies.

5. The immunoassay of claim 1 or 2, wherein the antibodies $B_{a'}^{n''}$ comprise anti-human IgG antibodies.

6. The immunoassay of claim 1 or 2, wherein the antibodies $B_{a'}^{n''}$ are bound to a detectable label, wherein the detectable label is an enzyme, oligonucleotide, nanoparticle chemiluminophore, fluorophore, fluorescence quencher, chemiluminescence quencher, or biotin.

7. The immunoassay of claim 1 or 2, wherein the optical signal is measured as a cardiac myocyte antigens a'' concentration dependent change in chemiluminescence, fluorescence, phosphorescence, electrochemiluminescence, ultraviolet absorption, visible absorption, infrared absorption, refraction, surface plasmon resonance.

8. The immunoassay of claim 1 or 2, wherein the electrical signal is measured as a cardiac myocyte antigens a'' concentration dependent change in current, resistance, potential, mass to charge ratio, or ion count.

9. The immunoassay of claim 1 or 2, wherein the change-of-state signal is measured as a cardiac myocyte antigens a'' concentration dependent change in size, solubility, mass, or resonance.

10. The immunoassay of claim 1 or 2, wherein the antibodies $A_{a'}^{n}$ are immobilized on a solid phase.

11. The immunoassay of claim 10, wherein the solid phase is selected from the group consisting of a magnetic particle, bead, test tube, microliter plate, cuvette, membrane, a scaffolding molecule, quartz crystal, film, filter paper, disc and chip.

12. The immunoassay of claim 1 or 2, wherein the test sample is whole blood, serum, or plasma.

* * * * *

SEQUENCE LISTING

```
<160> NUMBER OF SEQ ID NOS: 163

<210> SEQ ID NO 1
<211> LENGTH: 15
<212> TYPE: PRT
<213> ORGANISM: Homo sapiens

<400> SEQUENCE: 1

Ser Asp Ile Glu Glu Val Val Glu Glu Tyr Glu Glu Glu Glu Gln
1               5                   10                  15

<210> SEQ ID NO 2
<211> LENGTH: 15
```

-continued

```
<212> TYPE: PRT
<213> ORGANISM: Homo sapiens

<400> SEQUENCE: 2

Glu Glu Val Val Glu Glu Tyr Glu Glu Glu Gln Glu Glu Ala
1               5                   10                  15

<210> SEQ ID NO 3
<211> LENGTH: 15
<212> TYPE: PRT
<213> ORGANISM: Homo sapiens

<400> SEQUENCE: 3

Val Glu Glu Tyr Glu Glu Glu Gln Glu Glu Ala Ala Val Glu
1               5                   10                  15

<210> SEQ ID NO 4
<211> LENGTH: 15
<212> TYPE: PRT
<213> ORGANISM: Homo sapiens

<400> SEQUENCE: 4

Tyr Glu Glu Glu Gln Glu Glu Ala Ala Val Glu Glu Glu Glu
1               5                   10                  15

<210> SEQ ID NO 5
<211> LENGTH: 15
<212> TYPE: PRT
<213> ORGANISM: Homo sapiens

<400> SEQUENCE: 5

Glu Glu Gln Glu Glu Ala Ala Val Glu Glu Glu Glu Asp Trp Arg
1               5                   10                  15

<210> SEQ ID NO 6
<211> LENGTH: 15
<212> TYPE: PRT
<213> ORGANISM: Homo sapiens

<400> SEQUENCE: 6

Glu Glu Ala Ala Val Glu Glu Glu Glu Asp Trp Arg Glu Asp Glu
1               5                   10                  15

<210> SEQ ID NO 7
<211> LENGTH: 15
<212> TYPE: PRT
<213> ORGANISM: Homo sapiens

<400> SEQUENCE: 7

Ala Val Glu Glu Glu Glu Asp Trp Arg Glu Asp Glu Asp Glu Gln
1               5                   10                  15

<210> SEQ ID NO 8
<211> LENGTH: 15
<212> TYPE: PRT
<213> ORGANISM: Homo sapiens

<400> SEQUENCE: 8

Glu Glu Glu Asp Trp Arg Glu Asp Glu Asp Glu Gln Glu Glu Ala
1               5                   10                  15

<210> SEQ ID NO 9
<211> LENGTH: 15
<212> TYPE: PRT
<213> ORGANISM: Homo sapiens
```

<400> SEQUENCE: 9

Asp Trp Arg Glu Asp Glu Asp Glu Gln Glu Glu Ala Ala Glu Glu
1               5                   10                  15

<210> SEQ ID NO 10
<211> LENGTH: 15
<212> TYPE: PRT
<213> ORGANISM: Homo sapiens

<400> SEQUENCE: 10

Glu Asp Glu Asp Glu Gln Glu Glu Ala Ala Glu Glu Asp Ala Glu
1               5                   10                  15

<210> SEQ ID NO 11
<211> LENGTH: 15
<212> TYPE: PRT
<213> ORGANISM: Homo sapiens

<400> SEQUENCE: 11

Asp Glu Gln Glu Glu Ala Ala Glu Glu Asp Ala Glu Ala Glu Ala
1               5                   10                  15

<210> SEQ ID NO 12
<211> LENGTH: 15
<212> TYPE: PRT
<213> ORGANISM: Homo sapiens

<400> SEQUENCE: 12

Glu Glu Ala Ala Glu Glu Asp Ala Glu Ala Glu Ala Glu Thr Glu
1               5                   10                  15

<210> SEQ ID NO 13
<211> LENGTH: 15
<212> TYPE: PRT
<213> ORGANISM: Homo sapiens

<400> SEQUENCE: 13

Ala Glu Glu Asp Ala Glu Ala Glu Ala Glu Thr Glu Glu Thr Arg
1               5                   10                  15

<210> SEQ ID NO 14
<211> LENGTH: 15
<212> TYPE: PRT
<213> ORGANISM: Homo sapiens

<400> SEQUENCE: 14

Asp Ala Glu Ala Glu Ala Glu Thr Glu Glu Thr Arg Ala Glu Glu
1               5                   10                  15

<210> SEQ ID NO 15
<211> LENGTH: 15
<212> TYPE: PRT
<213> ORGANISM: Homo sapiens

<400> SEQUENCE: 15

Ala Glu Ala Glu Thr Glu Glu Thr Arg Ala Glu Glu Asp Glu Glu
1               5                   10                  15

<210> SEQ ID NO 16
<211> LENGTH: 15
<212> TYPE: PRT
<213> ORGANISM: Homo sapiens

<400> SEQUENCE: 16

Glu Thr Glu Glu Thr Arg Ala Glu Glu Asp Glu Glu Glu Glu Glu

```
                1               5                  10                 15
```

<210> SEQ ID NO 17
<211> LENGTH: 15
<212> TYPE: PRT
<213> ORGANISM: Homo sapiens

<400> SEQUENCE: 17

```
Glu Thr Arg Ala Glu Glu Asp Glu Glu Glu Glu Glu Ala Lys Glu
1               5                  10                 15
```

<210> SEQ ID NO 18
<211> LENGTH: 15
<212> TYPE: PRT
<213> ORGANISM: Homo sapiens

<400> SEQUENCE: 18

```
Ala Glu Glu Asp Glu Glu Glu Glu Ala Lys Glu Ala Glu Asp
1               5                  10                 15
```

<210> SEQ ID NO 19
<211> LENGTH: 15
<212> TYPE: PRT
<213> ORGANISM: Homo sapiens

<400> SEQUENCE: 19

```
Asp Glu Glu Glu Glu Glu Ala Lys Glu Ala Glu Asp Gly Pro Met
1               5                  10                 15
```

<210> SEQ ID NO 20
<211> LENGTH: 15
<212> TYPE: PRT
<213> ORGANISM: Homo sapiens

<400> SEQUENCE: 20

```
Glu Glu Glu Ala Lys Glu Ala Glu Asp Gly Pro Met Glu Glu Ser
1               5                  10                 15
```

<210> SEQ ID NO 21
<211> LENGTH: 15
<212> TYPE: PRT
<213> ORGANISM: Homo sapiens

<400> SEQUENCE: 21

```
Ala Lys Glu Ala Glu Asp Gly Pro Met Glu Glu Ser Lys Pro Lys
1               5                  10                 15
```

<210> SEQ ID NO 22
<211> LENGTH: 15
<212> TYPE: PRT
<213> ORGANISM: Homo sapiens

<400> SEQUENCE: 22

```
Ala Glu Asp Gly Pro Met Glu Glu Ser Lys Pro Lys Pro Arg Ser
1               5                  10                 15
```

<210> SEQ ID NO 23
<211> LENGTH: 15
<212> TYPE: PRT
<213> ORGANISM: Homo sapiens

<400> SEQUENCE: 23

```
Gly Pro Met Glu Glu Ser Lys Pro Lys Pro Arg Ser Phe Met Pro
1               5                  10                 15
```

```
<210> SEQ ID NO 24
<211> LENGTH: 15
<212> TYPE: PRT
<213> ORGANISM: Homo sapiens

<400> SEQUENCE: 24

Glu Glu Ser Lys Pro Lys Pro Arg Ser Phe Met Pro Asn Leu Val
1               5                   10                  15

<210> SEQ ID NO 25
<211> LENGTH: 15
<212> TYPE: PRT
<213> ORGANISM: Homo sapiens

<400> SEQUENCE: 25

Lys Pro Lys Pro Arg Ser Phe Met Pro Asn Leu Val Pro Pro Lys
1               5                   10                  15

<210> SEQ ID NO 26
<211> LENGTH: 15
<212> TYPE: PRT
<213> ORGANISM: Homo sapiens

<400> SEQUENCE: 26

Pro Arg Ser Phe Met Pro Asn Leu Val Pro Pro Lys Ile Pro Asp
1               5                   10                  15

<210> SEQ ID NO 27
<211> LENGTH: 15
<212> TYPE: PRT
<213> ORGANISM: Homo sapiens

<400> SEQUENCE: 27

Phe Met Pro Asn Leu Val Pro Pro Lys Ile Pro Asp Gly Glu Arg
1               5                   10                  15

<210> SEQ ID NO 28
<211> LENGTH: 15
<212> TYPE: PRT
<213> ORGANISM: Homo sapiens

<400> SEQUENCE: 28

Asn Leu Val Pro Pro Lys Ile Pro Asp Gly Glu Arg Val Asp Phe
1               5                   10                  15

<210> SEQ ID NO 29
<211> LENGTH: 15
<212> TYPE: PRT
<213> ORGANISM: Homo sapiens

<400> SEQUENCE: 29

Pro Pro Lys Ile Pro Asp Gly Glu Arg Val Asp Phe Asp Asp Ile
1               5                   10                  15

<210> SEQ ID NO 30
<211> LENGTH: 15
<212> TYPE: PRT
<213> ORGANISM: Homo sapiens

<400> SEQUENCE: 30

Ile Pro Asp Gly Glu Arg Val Asp Phe Asp Asp Ile His Arg Lys
1               5                   10                  15

<210> SEQ ID NO 31
<211> LENGTH: 15
<212> TYPE: PRT
```

<213> ORGANISM: Homo sapiens

<400> SEQUENCE: 31

Gly Glu Arg Val Asp Phe Asp Asp Ile His Arg Lys Arg Met Glu
1               5                   10                  15

<210> SEQ ID NO 32
<211> LENGTH: 15
<212> TYPE: PRT
<213> ORGANISM: Homo sapiens

<400> SEQUENCE: 32

Val Asp Phe Asp Asp Ile His Arg Lys Arg Met Glu Lys Asp Leu
1               5                   10                  15

<210> SEQ ID NO 33
<211> LENGTH: 15
<212> TYPE: PRT
<213> ORGANISM: Homo sapiens

<400> SEQUENCE: 33

Asp Asp Ile His Arg Lys Arg Met Glu Lys Asp Leu Asn Glu Leu
1               5                   10                  15

<210> SEQ ID NO 34
<211> LENGTH: 15
<212> TYPE: PRT
<213> ORGANISM: Homo sapiens

<400> SEQUENCE: 34

His Arg Lys Arg Met Glu Lys Asp Leu Asn Glu Leu Gln Ala Leu
1               5                   10                  15

<210> SEQ ID NO 35
<211> LENGTH: 15
<212> TYPE: PRT
<213> ORGANISM: Homo sapiens

<400> SEQUENCE: 35

Arg Met Glu Lys Asp Leu Asn Glu Leu Gln Ala Leu Ile Glu Ala
1               5                   10                  15

<210> SEQ ID NO 36
<211> LENGTH: 15
<212> TYPE: PRT
<213> ORGANISM: Homo sapiens

<400> SEQUENCE: 36

Lys Asp Leu Asn Glu Leu Gln Ala Leu Ile Glu Ala His Phe Glu
1               5                   10                  15

<210> SEQ ID NO 37
<211> LENGTH: 15
<212> TYPE: PRT
<213> ORGANISM: Homo sapiens

<400> SEQUENCE: 37

Asn Glu Leu Gln Ala Leu Ile Glu Ala His Phe Glu Asn Arg Lys
1               5                   10                  15

<210> SEQ ID NO 38
<211> LENGTH: 15
<212> TYPE: PRT
<213> ORGANISM: Homo sapiens

<400> SEQUENCE: 38

Gln Ala Leu Ile Glu Ala His Phe Glu Asn Arg Lys Lys Glu Glu
1               5                   10                  15

<210> SEQ ID NO 39
<211> LENGTH: 15
<212> TYPE: PRT
<213> ORGANISM: Homo sapiens

<400> SEQUENCE: 39

Ile Glu Ala His Phe Glu Asn Arg Lys Lys Glu Glu Glu Glu Leu
1               5                   10                  15

<210> SEQ ID NO 40
<211> LENGTH: 15
<212> TYPE: PRT
<213> ORGANISM: Homo sapiens

<400> SEQUENCE: 40

His Phe Glu Asn Arg Lys Lys Glu Glu Glu Glu Leu Val Ser Leu
1               5                   10                  15

<210> SEQ ID NO 41
<211> LENGTH: 15
<212> TYPE: PRT
<213> ORGANISM: Homo sapiens

<400> SEQUENCE: 41

Asn Arg Lys Lys Glu Glu Glu Glu Leu Val Ser Leu Lys Asp Arg
1               5                   10                  15

<210> SEQ ID NO 42
<211> LENGTH: 15
<212> TYPE: PRT
<213> ORGANISM: Homo sapiens

<400> SEQUENCE: 42

Lys Glu Glu Glu Glu Leu Val Ser Leu Lys Asp Arg Ile Glu Arg
1               5                   10                  15

<210> SEQ ID NO 43
<211> LENGTH: 15
<212> TYPE: PRT
<213> ORGANISM: Homo sapiens

<400> SEQUENCE: 43

Glu Glu Leu Val Ser Leu Lys Asp Arg Ile Glu Arg Arg Arg Ala
1               5                   10                  15

<210> SEQ ID NO 44
<211> LENGTH: 15
<212> TYPE: PRT
<213> ORGANISM: Homo sapiens

<400> SEQUENCE: 44

Val Ser Leu Lys Asp Arg Ile Glu Arg Arg Arg Ala Glu Arg Ala
1               5                   10                  15

<210> SEQ ID NO 45
<211> LENGTH: 15
<212> TYPE: PRT
<213> ORGANISM: Homo sapiens

<400> SEQUENCE: 45

Lys Asp Arg Ile Glu Arg Arg Arg Ala Glu Arg Ala Glu Gln Gln
1               5                   10                  15

<210> SEQ ID NO 46
<211> LENGTH: 15
<212> TYPE: PRT
<213> ORGANISM: Homo sapiens

<400> SEQUENCE: 46

Ile Glu Arg Arg Arg Ala Glu Arg Ala Glu Gln Gln Arg Ile Arg
1               5                   10                  15

<210> SEQ ID NO 47
<211> LENGTH: 15
<212> TYPE: PRT
<213> ORGANISM: Homo sapiens

<400> SEQUENCE: 47

Arg Arg Ala Glu Arg Ala Glu Gln Gln Arg Ile Arg Asn Glu Arg
1               5                   10                  15

<210> SEQ ID NO 48
<211> LENGTH: 15
<212> TYPE: PRT
<213> ORGANISM: Homo sapiens

<400> SEQUENCE: 48

Glu Arg Ala Glu Gln Gln Arg Ile Arg Asn Glu Arg Glu Lys Glu
1               5                   10                  15

<210> SEQ ID NO 49
<211> LENGTH: 15
<212> TYPE: PRT
<213> ORGANISM: Homo sapiens

<400> SEQUENCE: 49

Glu Gln Gln Arg Ile Arg Asn Glu Arg Glu Lys Glu Arg Gln Asn
1               5                   10                  15

<210> SEQ ID NO 50
<211> LENGTH: 15
<212> TYPE: PRT
<213> ORGANISM: Homo sapiens

<400> SEQUENCE: 50

Arg Ile Arg Asn Glu Arg Glu Lys Glu Arg Gln Asn Arg Leu Ala
1               5                   10                  15

<210> SEQ ID NO 51
<211> LENGTH: 15
<212> TYPE: PRT
<213> ORGANISM: Homo sapiens

<400> SEQUENCE: 51

Asn Glu Arg Glu Lys Glu Arg Gln Asn Arg Leu Ala Glu Glu Arg
1               5                   10                  15

<210> SEQ ID NO 52
<211> LENGTH: 15
<212> TYPE: PRT
<213> ORGANISM: Homo sapiens

<400> SEQUENCE: 52

Glu Lys Glu Arg Gln Asn Arg Leu Ala Glu Glu Arg Ala Arg Arg
1               5                   10                  15

<210> SEQ ID NO 53

```
<211> LENGTH: 15
<212> TYPE: PRT
<213> ORGANISM: Homo sapiens

<400> SEQUENCE: 53

Arg Gln Asn Arg Leu Ala Glu Glu Arg Ala Arg Arg Glu Glu Glu
1               5                   10                  15

<210> SEQ ID NO 54
<211> LENGTH: 15
<212> TYPE: PRT
<213> ORGANISM: Homo sapiens

<400> SEQUENCE: 54

Arg Leu Ala Glu Glu Arg Ala Arg Arg Glu Glu Glu Glu Asn Arg
1               5                   10                  15

<210> SEQ ID NO 55
<211> LENGTH: 15
<212> TYPE: PRT
<213> ORGANISM: Homo sapiens

<400> SEQUENCE: 55

Glu Glu Arg Ala Arg Arg Glu Glu Glu Glu Asn Arg Arg Lys Ala
1               5                   10                  15

<210> SEQ ID NO 56
<211> LENGTH: 15
<212> TYPE: PRT
<213> ORGANISM: Homo sapiens

<400> SEQUENCE: 56

Ala Arg Arg Glu Glu Glu Glu Asn Arg Arg Lys Ala Glu Asp Glu
1               5                   10                  15

<210> SEQ ID NO 57
<211> LENGTH: 15
<212> TYPE: PRT
<213> ORGANISM: Homo sapiens

<400> SEQUENCE: 57

Glu Glu Glu Glu Asn Arg Arg Lys Ala Glu Asp Glu Ala Arg Lys
1               5                   10                  15

<210> SEQ ID NO 58
<211> LENGTH: 15
<212> TYPE: PRT
<213> ORGANISM: Homo sapiens

<400> SEQUENCE: 58

Glu Asn Arg Arg Lys Ala Glu Asp Glu Ala Arg Lys Lys Lys Ala
1               5                   10                  15

<210> SEQ ID NO 59
<211> LENGTH: 15
<212> TYPE: PRT
<213> ORGANISM: Homo sapiens

<400> SEQUENCE: 59

Arg Lys Ala Glu Asp Glu Ala Arg Lys Lys Lys Ala Leu Ser Asn
1               5                   10                  15

<210> SEQ ID NO 60
<211> LENGTH: 15
<212> TYPE: PRT
```

-continued

<400> SEQUENCE: 60

Glu Asp Glu Ala Arg Lys Lys Lys Ala Leu Ser Asn Met Met His
1               5                   10                  15

<210> SEQ ID NO 61
<211> LENGTH: 15
<212> TYPE: PRT
<213> ORGANISM: Homo sapiens

<400> SEQUENCE: 61

Ala Arg Lys Lys Lys Ala Leu Ser Asn Met Met His Phe Gly Gly
1               5                   10                  15

<210> SEQ ID NO 62
<211> LENGTH: 15
<212> TYPE: PRT
<213> ORGANISM: Homo sapiens

<400> SEQUENCE: 62

Lys Lys Ala Leu Ser Asn Met Met His Phe Gly Gly Tyr Ile Gln
1               5                   10                  15

<210> SEQ ID NO 63
<211> LENGTH: 15
<212> TYPE: PRT
<213> ORGANISM: Homo sapiens

<400> SEQUENCE: 63

Leu Ser Asn Met Met His Phe Gly Gly Tyr Ile Gln Lys Gln Ala
1               5                   10                  15

<210> SEQ ID NO 64
<211> LENGTH: 15
<212> TYPE: PRT
<213> ORGANISM: Homo sapiens

<400> SEQUENCE: 64

Met Met His Phe Gly Gly Tyr Ile Gln Lys Gln Ala Gln Thr Glu
1               5                   10                  15

<210> SEQ ID NO 65
<211> LENGTH: 15
<212> TYPE: PRT
<213> ORGANISM: Homo sapiens

<400> SEQUENCE: 65

Phe Gly Gly Tyr Ile Gln Lys Gln Ala Gln Thr Glu Arg Lys Ser
1               5                   10                  15

<210> SEQ ID NO 66
<211> LENGTH: 15
<212> TYPE: PRT
<213> ORGANISM: Homo sapiens

<400> SEQUENCE: 66

Tyr Ile Gln Lys Gln Ala Gln Thr Glu Arg Lys Ser Gly Lys Arg
1               5                   10                  15

<210> SEQ ID NO 67
<211> LENGTH: 15
<212> TYPE: PRT
<213> ORGANISM: Homo sapiens

<400> SEQUENCE: 67

```
Lys Gln Ala Gln Thr Glu Arg Lys Ser Gly Lys Arg Gln Thr Glu
1               5                   10                  15
```

<210> SEQ ID NO 68
<211> LENGTH: 15
<212> TYPE: PRT
<213> ORGANISM: Homo sapiens

<400> SEQUENCE: 68

```
Gln Thr Glu Arg Lys Ser Gly Lys Arg Gln Thr Glu Arg Glu Lys
1               5                   10                  15
```

<210> SEQ ID NO 69
<211> LENGTH: 15
<212> TYPE: PRT
<213> ORGANISM: Homo sapiens

<400> SEQUENCE: 69

```
Arg Lys Ser Gly Lys Arg Gln Thr Glu Arg Glu Lys Lys Lys Lys
1               5                   10                  15
```

<210> SEQ ID NO 70
<211> LENGTH: 15
<212> TYPE: PRT
<213> ORGANISM: Homo sapiens

<400> SEQUENCE: 70

```
Gly Lys Arg Gln Thr Glu Arg Glu Lys Lys Lys Lys Ile Leu Ala
1               5                   10                  15
```

<210> SEQ ID NO 71
<211> LENGTH: 15
<212> TYPE: PRT
<213> ORGANISM: Homo sapiens

<400> SEQUENCE: 71

```
Gln Thr Glu Arg Glu Lys Lys Lys Lys Ile Leu Ala Glu Arg Arg
1               5                   10                  15
```

<210> SEQ ID NO 72
<211> LENGTH: 15
<212> TYPE: PRT
<213> ORGANISM: Homo sapiens

<400> SEQUENCE: 72

```
Arg Glu Lys Lys Lys Lys Ile Leu Ala Glu Arg Arg Lys Val Leu
1               5                   10                  15
```

<210> SEQ ID NO 73
<211> LENGTH: 15
<212> TYPE: PRT
<213> ORGANISM: Homo sapiens

<400> SEQUENCE: 73

```
Lys Lys Lys Ile Leu Ala Glu Arg Arg Lys Val Leu Ala Ile Asp
1               5                   10                  15
```

<210> SEQ ID NO 74
<211> LENGTH: 15
<212> TYPE: PRT
<213> ORGANISM: Homo sapiens

<400> SEQUENCE: 74

```
Ile Leu Ala Glu Arg Arg Lys Val Leu Ala Ile Asp His Leu Asn
1               5                   10                  15
```

```
<210> SEQ ID NO 75
<211> LENGTH: 15
<212> TYPE: PRT
<213> ORGANISM: Homo sapiens

<400> SEQUENCE: 75

Glu Arg Arg Lys Val Leu Ala Ile Asp His Leu Asn Glu Asp Gln
1               5                   10                  15

<210> SEQ ID NO 76
<211> LENGTH: 15
<212> TYPE: PRT
<213> ORGANISM: Homo sapiens

<400> SEQUENCE: 76

Lys Val Leu Ala Ile Asp His Leu Asn Glu Asp Gln Leu Arg Glu
1               5                   10                  15

<210> SEQ ID NO 77
<211> LENGTH: 15
<212> TYPE: PRT
<213> ORGANISM: Homo sapiens

<400> SEQUENCE: 77

Ala Ile Asp His Leu Asn Glu Asp Gln Leu Arg Glu Lys Ala Lys
1               5                   10                  15

<210> SEQ ID NO 78
<211> LENGTH: 15
<212> TYPE: PRT
<213> ORGANISM: Homo sapiens

<400> SEQUENCE: 78

His Leu Asn Glu Asp Gln Leu Arg Glu Lys Ala Lys Glu Leu Trp
1               5                   10                  15

<210> SEQ ID NO 79
<211> LENGTH: 15
<212> TYPE: PRT
<213> ORGANISM: Homo sapiens

<400> SEQUENCE: 79

Glu Asp Gln Leu Arg Glu Lys Ala Lys Glu Leu Trp Gln Ser Ile
1               5                   10                  15

<210> SEQ ID NO 80
<211> LENGTH: 15
<212> TYPE: PRT
<213> ORGANISM: Homo sapiens

<400> SEQUENCE: 80

Leu Arg Glu Lys Ala Lys Glu Leu Trp Gln Ser Ile Tyr Asn Leu
1               5                   10                  15

<210> SEQ ID NO 81
<211> LENGTH: 15
<212> TYPE: PRT
<213> ORGANISM: Homo sapiens

<400> SEQUENCE: 81

Lys Ala Lys Glu Leu Trp Gln Ser Ile Tyr Asn Leu Glu Ala Glu
1               5                   10                  15

<210> SEQ ID NO 82
<211> LENGTH: 15
```

```
<212> TYPE: PRT
<213> ORGANISM: Homo sapiens

<400> SEQUENCE: 82

Glu Leu Trp Gln Ser Ile Tyr Asn Leu Glu Ala Glu Lys Phe Asp
1               5                   10                  15

<210> SEQ ID NO 83
<211> LENGTH: 15
<212> TYPE: PRT
<213> ORGANISM: Homo sapiens

<400> SEQUENCE: 83

Gln Ser Ile Tyr Asn Leu Glu Ala Glu Lys Phe Asp Leu Gln Glu
1               5                   10                  15

<210> SEQ ID NO 84
<211> LENGTH: 15
<212> TYPE: PRT
<213> ORGANISM: Homo sapiens

<400> SEQUENCE: 84

Tyr Asn Leu Glu Ala Glu Lys Phe Asp Leu Gln Glu Lys Phe Lys
1               5                   10                  15

<210> SEQ ID NO 85
<211> LENGTH: 15
<212> TYPE: PRT
<213> ORGANISM: Homo sapiens

<400> SEQUENCE: 85

Glu Ala Glu Lys Phe Asp Leu Gln Glu Lys Phe Lys Gln Gln Lys
1               5                   10                  15

<210> SEQ ID NO 86
<211> LENGTH: 15
<212> TYPE: PRT
<213> ORGANISM: Homo sapiens

<400> SEQUENCE: 86

Lys Phe Asp Leu Gln Glu Lys Phe Lys Gln Gln Lys Tyr Glu Ile
1               5                   10                  15

<210> SEQ ID NO 87
<211> LENGTH: 15
<212> TYPE: PRT
<213> ORGANISM: Homo sapiens

<400> SEQUENCE: 87

Leu Gln Glu Lys Phe Lys Gln Gln Lys Tyr Glu Ile Asn Val Leu
1               5                   10                  15

<210> SEQ ID NO 88
<211> LENGTH: 15
<212> TYPE: PRT
<213> ORGANISM: Homo sapiens

<400> SEQUENCE: 88

Lys Phe Lys Gln Gln Lys Tyr Glu Ile Asn Val Leu Arg Asn Arg
1               5                   10                  15

<210> SEQ ID NO 89
<211> LENGTH: 15
<212> TYPE: PRT
<213> ORGANISM: Homo sapiens
```

```
<400> SEQUENCE: 89

Gln Gln Lys Tyr Glu Ile Asn Val Leu Arg Asn Arg Ile Asn Asp
1               5                   10                  15

<210> SEQ ID NO 90
<211> LENGTH: 15
<212> TYPE: PRT
<213> ORGANISM: Homo sapiens

<400> SEQUENCE: 90

Tyr Glu Ile Asn Val Leu Arg Asn Arg Ile Asn Asp Asn Gln Lys
1               5                   10                  15

<210> SEQ ID NO 91
<211> LENGTH: 15
<212> TYPE: PRT
<213> ORGANISM: Homo sapiens

<400> SEQUENCE: 91

Asn Val Leu Arg Asn Arg Ile Asn Asp Asn Gln Lys Val Ser Lys
1               5                   10                  15

<210> SEQ ID NO 92
<211> LENGTH: 15
<212> TYPE: PRT
<213> ORGANISM: Homo sapiens

<400> SEQUENCE: 92

Arg Asn Arg Ile Asn Asp Asn Gln Lys Val Ser Lys Thr Arg Gly
1               5                   10                  15

<210> SEQ ID NO 93
<211> LENGTH: 15
<212> TYPE: PRT
<213> ORGANISM: Homo sapiens

<400> SEQUENCE: 93

Ile Asn Asp Asn Gln Lys Val Ser Lys Thr Arg Gly Lys Ala Lys
1               5                   10                  15

<210> SEQ ID NO 94
<211> LENGTH: 15
<212> TYPE: PRT
<213> ORGANISM: Homo sapiens

<400> SEQUENCE: 94

Asn Gln Lys Val Ser Lys Thr Arg Gly Lys Ala Lys Val Thr Gly
1               5                   10                  15

<210> SEQ ID NO 95
<211> LENGTH: 15
<212> TYPE: PRT
<213> ORGANISM: Homo sapiens

<400> SEQUENCE: 95

Val Ser Lys Thr Arg Gly Lys Ala Lys Val Thr Gly Arg Trp Lys
1               5                   10                  15

<210> SEQ ID NO 96
<211> LENGTH: 297
<212> TYPE: PRT
<213> ORGANISM: Homo sapiens

<400> SEQUENCE: 96

Ser Asp Ile Glu Glu Val Val Glu Glu Tyr Glu Glu Glu Gln Glu
```

```
                1               5                   10                  15
Glu Ala Ala Val Glu Glu Glu Asp Trp Arg Glu Asp Glu
                    20                  25                  30
Gln Glu Glu Ala Ala Glu Glu Asp Ala Glu Ala Glu Thr Glu
                35                  40                  45
Glu Thr Arg Ala Glu Glu Asp Glu Glu Glu Glu Ala Lys Glu Ala
 50                  55                  60
Glu Asp Gly Pro Met Glu Glu Ser Lys Pro Lys Pro Arg Ser Phe Met
 65                  70                  75                  80
Pro Asn Leu Val Pro Pro Lys Ile Pro Asp Gly Glu Arg Val Asp Phe
                    85                  90                  95
Asp Asp Ile His Arg Lys Arg Met Glu Lys Asp Leu Asn Glu Leu Gln
                    100                 105                 110
Ala Leu Ile Glu Ala His Phe Glu Asn Arg Lys Lys Glu Glu Glu
                    115                 120                 125
Leu Val Ser Leu Lys Asp Arg Ile Glu Arg Arg Ala Glu Arg Ala
                    130                 135                 140
Glu Gln Gln Arg Ile Arg Asn Glu Arg Glu Lys Glu Arg Gln Asn Arg
145                 150                 155                 160
Leu Ala Glu Glu Arg Ala Arg Arg Glu Glu Glu Asn Arg Arg Lys
                    165                 170                 175
Ala Glu Asp Glu Ala Arg Lys Lys Lys Ala Leu Ser Asn Met Met His
                    180                 185                 190
Phe Gly Gly Tyr Ile Gln Lys Gln Ala Gln Thr Glu Arg Lys Ser Gly
                    195                 200                 205
Lys Arg Gln Thr Glu Arg Glu Lys Lys Lys Ile Leu Ala Glu Arg
                    210                 215                 220
Arg Lys Val Leu Ala Ile Asp His Leu Asn Glu Asp Gln Leu Arg Glu
225                 230                 235                 240
Lys Ala Lys Glu Leu Trp Gln Ser Ile Tyr Asn Leu Glu Ala Glu Lys
                    245                 250                 255
Phe Asp Leu Gln Glu Lys Phe Lys Gln Gln Lys Tyr Glu Ile Asn Val
                    260                 265                 270
Leu Arg Asn Arg Ile Asn Asp Asn Gln Lys Val Ser Lys Thr Arg Gly
                    275                 280                 285
Lys Ala Lys Val Thr Gly Arg Trp Lys
                    290                 295

<210> SEQ ID NO 97
<211> LENGTH: 209
<212> TYPE: PRT
<213> ORGANISM: Homo sapiens

<400> SEQUENCE: 97

Ala Asp Gly Ser Ser Asp Ala Ala Arg Glu Pro Arg Pro Ala Pro Ala
 1               5                   10                  15
Pro Ile Arg Arg Arg Ser Ser Asn Tyr Arg Ala Tyr Ala Thr Glu Pro
                    20                  25                  30
His Ala Lys Lys Lys Ser Lys Ile Ser Ala Ser Arg Lys Leu Gln Leu
                35                  40                  45
Lys Thr Leu Leu Leu Gln Ile Ala Lys Gln Glu Leu Glu Arg Glu Ala
                    50                  55                  60
Glu Glu Arg Arg Gly Glu Lys Gly Arg Ala Leu Ser Thr Arg Cys Gln
 65                  70                  75                  80
Pro Leu Glu Leu Ala Gly Leu Gly Phe Ala Glu Leu Gln Asp Leu Cys
```

```
                85                  90                  95
Arg Gln Leu His Ala Arg Val Asp Lys Val Asp Glu Glu Arg Tyr Asp
            100                 105                 110

Ile Glu Ala Lys Val Thr Lys Asn Ile Thr Glu Ile Ala Asp Leu Thr
        115                 120                 125

Gln Lys Ile Phe Asp Leu Arg Gly Lys Phe Lys Arg Pro Thr Leu Arg
    130                 135                 140

Arg Val Arg Ile Ser Ala Asp Ala Met Met Gln Ala Leu Leu Gly Ala
145                 150                 155                 160

Arg Ala Lys Glu Ser Leu Asp Leu Arg Ala His Leu Lys Gln Val Lys
                165                 170                 175

Lys Glu Asp Thr Glu Lys Glu Asn Arg Glu Val Gly Asp Trp Arg Lys
            180                 185                 190

Asn Ile Asp Ala Leu Ser Gly Met Glu Gly Arg Lys Lys Lys Phe Glu
        195                 200                 205

Ser

<210> SEQ ID NO 98
<211> LENGTH: 15
<212> TYPE: PRT
<213> ORGANISM: Homo sapiens

<400> SEQUENCE: 98

Ala Asp Gly Ser Ser Asp Ala Ala Arg Glu Pro Arg Pro Ala Pro
1               5                   10                  15

<210> SEQ ID NO 99
<211> LENGTH: 15
<212> TYPE: PRT
<213> ORGANISM: Homo sapiens

<400> SEQUENCE: 99

Ser Ser Asp Ala Ala Arg Glu Pro Arg Pro Ala Pro Ala Pro Ile
1               5                   10                  15

<210> SEQ ID NO 100
<211> LENGTH: 15
<212> TYPE: PRT
<213> ORGANISM: Homo sapiens

<400> SEQUENCE: 100

Ala Ala Arg Glu Pro Arg Pro Ala Pro Ala Pro Ile Arg Arg Arg
1               5                   10                  15

<210> SEQ ID NO 101
<211> LENGTH: 15
<212> TYPE: PRT
<213> ORGANISM: Homo sapiens

<400> SEQUENCE: 101

Glu Pro Arg Pro Ala Pro Ala Pro Ile Arg Arg Arg Ser Ser Asn
1               5                   10                  15

<210> SEQ ID NO 102
<211> LENGTH: 15
<212> TYPE: PRT
<213> ORGANISM: Homo sapiens

<400> SEQUENCE: 102

Pro Ala Pro Ala Pro Ile Arg Arg Arg Ser Ser Asn Tyr Arg Ala
1               5                   10                  15
```

<210> SEQ ID NO 103
<211> LENGTH: 15
<212> TYPE: PRT
<213> ORGANISM: Homo sapiens

<400> SEQUENCE: 103

Ala Pro Ile Arg Arg Ser Ser Asn Tyr Arg Ala Tyr Ala Thr
1               5                   10                  15

<210> SEQ ID NO 104
<211> LENGTH: 15
<212> TYPE: PRT
<213> ORGANISM: Homo sapiens

<400> SEQUENCE: 104

Arg Arg Arg Ser Ser Asn Tyr Arg Ala Tyr Ala Thr Glu Pro His
1               5                   10                  15

<210> SEQ ID NO 105
<211> LENGTH: 15
<212> TYPE: PRT
<213> ORGANISM: Homo sapiens

<400> SEQUENCE: 105

Ser Ser Asn Tyr Arg Ala Tyr Ala Thr Glu Pro His Ala Lys Lys
1               5                   10                  15

<210> SEQ ID NO 106
<211> LENGTH: 15
<212> TYPE: PRT
<213> ORGANISM: Homo sapiens

<400> SEQUENCE: 106

Tyr Arg Ala Tyr Ala Thr Glu Pro His Ala Lys Lys Lys Ser Lys
1               5                   10                  15

<210> SEQ ID NO 107
<211> LENGTH: 15
<212> TYPE: PRT
<213> ORGANISM: Homo sapiens

<400> SEQUENCE: 107

Tyr Ala Thr Glu Pro His Ala Lys Lys Lys Ser Lys Ile Ser Ala
1               5                   10                  15

<210> SEQ ID NO 108
<211> LENGTH: 15
<212> TYPE: PRT
<213> ORGANISM: Homo sapiens

<400> SEQUENCE: 108

Glu Pro His Ala Lys Lys Lys Ser Lys Ile Ser Ala Ser Arg Lys
1               5                   10                  15

<210> SEQ ID NO 109
<211> LENGTH: 15
<212> TYPE: PRT
<213> ORGANISM: Homo sapiens

<400> SEQUENCE: 109

Ala Lys Lys Lys Ser Lys Ile Ser Ala Ser Arg Lys Leu Gln Leu
1               5                   10                  15

<210> SEQ ID NO 110
<211> LENGTH: 15

```
<212> TYPE: PRT
<213> ORGANISM: Homo sapiens

<400> SEQUENCE: 110

Lys Ser Lys Ile Ser Ala Ser Arg Lys Leu Gln Leu Lys Thr Leu
1               5                   10                  15

<210> SEQ ID NO 111
<211> LENGTH: 15
<212> TYPE: PRT
<213> ORGANISM: Homo sapiens

<400> SEQUENCE: 111

Ile Ser Ala Ser Arg Lys Leu Gln Leu Lys Thr Leu Leu Leu Gln
1               5                   10                  15

<210> SEQ ID NO 112
<211> LENGTH: 15
<212> TYPE: PRT
<213> ORGANISM: Homo sapiens

<400> SEQUENCE: 112

Ser Arg Lys Leu Gln Leu Lys Thr Leu Leu Leu Gln Ile Ala Lys
1               5                   10                  15

<210> SEQ ID NO 113
<211> LENGTH: 15
<212> TYPE: PRT
<213> ORGANISM: Homo sapiens

<400> SEQUENCE: 113

Leu Gln Leu Lys Thr Leu Leu Leu Gln Ile Ala Lys Gln Glu Leu
1               5                   10                  15

<210> SEQ ID NO 114
<211> LENGTH: 15
<212> TYPE: PRT
<213> ORGANISM: Homo sapiens

<400> SEQUENCE: 114

Lys Thr Leu Leu Leu Gln Ile Ala Lys Gln Glu Leu Glu Arg Glu
1               5                   10                  15

<210> SEQ ID NO 115
<211> LENGTH: 15
<212> TYPE: PRT
<213> ORGANISM: Homo sapiens

<400> SEQUENCE: 115

Leu Leu Gln Ile Ala Lys Gln Glu Leu Glu Arg Glu Ala Glu Glu
1               5                   10                  15

<210> SEQ ID NO 116
<211> LENGTH: 15
<212> TYPE: PRT
<213> ORGANISM: Homo sapiens

<400> SEQUENCE: 116

Ile Ala Lys Gln Glu Leu Glu Arg Glu Ala Glu Glu Arg Arg Gly
1               5                   10                  15

<210> SEQ ID NO 117
<211> LENGTH: 15
<212> TYPE: PRT
<213> ORGANISM: Homo sapiens
```

```
<400> SEQUENCE: 117

Gln Glu Leu Glu Arg Glu Ala Glu Glu Arg Arg Gly Glu Lys Gly
1               5                   10                  15

<210> SEQ ID NO 118
<211> LENGTH: 15
<212> TYPE: PRT
<213> ORGANISM: Homo sapiens

<400> SEQUENCE: 118

Glu Arg Glu Ala Glu Glu Arg Arg Gly Glu Lys Gly Arg Ala Leu
1               5                   10                  15

<210> SEQ ID NO 119
<211> LENGTH: 15
<212> TYPE: PRT
<213> ORGANISM: Homo sapiens

<400> SEQUENCE: 119

Ala Glu Glu Arg Arg Gly Glu Lys Gly Arg Ala Leu Ser Thr Arg
1               5                   10                  15

<210> SEQ ID NO 120
<211> LENGTH: 15
<212> TYPE: PRT
<213> ORGANISM: Homo sapiens

<400> SEQUENCE: 120

Arg Arg Gly Glu Lys Gly Arg Ala Leu Ser Thr Arg Cys Gln Pro
1               5                   10                  15

<210> SEQ ID NO 121
<211> LENGTH: 15
<212> TYPE: PRT
<213> ORGANISM: Homo sapiens

<400> SEQUENCE: 121

Glu Lys Gly Arg Ala Leu Ser Thr Arg Cys Gln Pro Leu Glu Leu
1               5                   10                  15

<210> SEQ ID NO 122
<211> LENGTH: 15
<212> TYPE: PRT
<213> ORGANISM: Homo sapiens

<400> SEQUENCE: 122

Arg Ala Leu Ser Thr Arg Cys Gln Pro Leu Glu Leu Ala Gly Leu
1               5                   10                  15

<210> SEQ ID NO 123
<211> LENGTH: 15
<212> TYPE: PRT
<213> ORGANISM: Homo sapiens

<400> SEQUENCE: 123

Ser Thr Arg Cys Gln Pro Leu Glu Leu Ala Gly Leu Gly Phe Ala
1               5                   10                  15

<210> SEQ ID NO 124
<211> LENGTH: 15
<212> TYPE: PRT
<213> ORGANISM: Homo sapiens

<400> SEQUENCE: 124

Cys Gln Pro Leu Glu Leu Ala Gly Leu Gly Phe Ala Glu Leu Gln
```

```
                        1               5                  10                 15

<210> SEQ ID NO 125
<211> LENGTH: 15
<212> TYPE: PRT
<213> ORGANISM: Homo sapiens

<400> SEQUENCE: 125

Leu Glu Leu Ala Gly Leu Gly Phe Ala Glu Leu Gln Asp Leu Cys
1               5                   10                  15

<210> SEQ ID NO 126
<211> LENGTH: 15
<212> TYPE: PRT
<213> ORGANISM: Homo sapiens

<400> SEQUENCE: 126

Ala Gly Leu Gly Phe Ala Glu Leu Gln Asp Leu Cys Arg Gln Leu
1               5                   10                  15

<210> SEQ ID NO 127
<211> LENGTH: 15
<212> TYPE: PRT
<213> ORGANISM: Homo sapiens

<400> SEQUENCE: 127

Gly Phe Ala Glu Leu Gln Asp Leu Cys Arg Gln Leu His Ala Arg
1               5                   10                  15

<210> SEQ ID NO 128
<211> LENGTH: 15
<212> TYPE: PRT
<213> ORGANISM: Homo sapiens

<400> SEQUENCE: 128

Glu Leu Gln Asp Leu Cys Arg Gln Leu His Ala Arg Val Asp Lys
1               5                   10                  15

<210> SEQ ID NO 129
<211> LENGTH: 15
<212> TYPE: PRT
<213> ORGANISM: Homo sapiens

<400> SEQUENCE: 129

Asp Leu Cys Arg Gln Leu His Ala Arg Val Asp Lys Val Asp Glu
1               5                   10                  15

<210> SEQ ID NO 130
<211> LENGTH: 15
<212> TYPE: PRT
<213> ORGANISM: Homo sapiens

<400> SEQUENCE: 130

Arg Gln Leu His Ala Arg Val Asp Lys Val Asp Glu Glu Arg Tyr
1               5                   10                  15

<210> SEQ ID NO 131
<211> LENGTH: 15
<212> TYPE: PRT
<213> ORGANISM: Homo sapiens

<400> SEQUENCE: 131

His Ala Arg Val Asp Lys Val Asp Glu Glu Arg Tyr Asp Ile Glu
1               5                   10                  15
```

```
<210> SEQ ID NO 132
<211> LENGTH: 15
<212> TYPE: PRT
<213> ORGANISM: Homo sapiens

<400> SEQUENCE: 132

Val Asp Lys Val Asp Glu Glu Arg Tyr Asp Ile Glu Ala Lys Val
1               5                   10                  15

<210> SEQ ID NO 133
<211> LENGTH: 15
<212> TYPE: PRT
<213> ORGANISM: Homo sapiens

<400> SEQUENCE: 133

Val Asp Glu Glu Arg Tyr Asp Ile Glu Ala Lys Val Thr Lys Asn
1               5                   10                  15

<210> SEQ ID NO 134
<211> LENGTH: 15
<212> TYPE: PRT
<213> ORGANISM: Homo sapiens

<400> SEQUENCE: 134

Glu Arg Tyr Asp Ile Glu Ala Lys Val Thr Lys Asn Ile Thr Glu
1               5                   10                  15

<210> SEQ ID NO 135
<211> LENGTH: 15
<212> TYPE: PRT
<213> ORGANISM: Homo sapiens

<400> SEQUENCE: 135

Asp Ile Glu Ala Lys Val Thr Lys Asn Ile Thr Glu Ile Ala Asp
1               5                   10                  15

<210> SEQ ID NO 136
<211> LENGTH: 15
<212> TYPE: PRT
<213> ORGANISM: Homo sapiens

<400> SEQUENCE: 136

Ala Lys Val Thr Lys Asn Ile Thr Glu Ile Ala Asp Leu Thr Gln
1               5                   10                  15

<210> SEQ ID NO 137
<211> LENGTH: 15
<212> TYPE: PRT
<213> ORGANISM: Homo sapiens

<400> SEQUENCE: 137

Thr Lys Asn Ile Thr Glu Ile Ala Asp Leu Thr Gln Lys Ile Phe
1               5                   10                  15

<210> SEQ ID NO 138
<211> LENGTH: 15
<212> TYPE: PRT
<213> ORGANISM: Homo sapiens

<400> SEQUENCE: 138

Ile Thr Glu Ile Ala Asp Leu Thr Gln Lys Ile Phe Asp Leu Arg
1               5                   10                  15

<210> SEQ ID NO 139
<211> LENGTH: 15
<212> TYPE: PRT
```

<213> ORGANISM: Homo sapiens

<400> SEQUENCE: 139

```
Ile Ala Asp Leu Thr Gln Lys Ile Phe Asp Leu Arg Gly Lys Phe
1               5                   10                  15
```

<210> SEQ ID NO 140
<211> LENGTH: 15
<212> TYPE: PRT
<213> ORGANISM: Homo sapiens

<400> SEQUENCE: 140

```
Leu Thr Gln Lys Ile Phe Asp Leu Arg Gly Lys Phe Lys Arg Pro
1               5                   10                  15
```

<210> SEQ ID NO 141
<211> LENGTH: 15
<212> TYPE: PRT
<213> ORGANISM: Homo sapiens

<400> SEQUENCE: 141

```
Lys Ile Phe Asp Leu Arg Gly Lys Phe Lys Arg Pro Thr Leu Arg
1               5                   10                  15
```

<210> SEQ ID NO 142
<211> LENGTH: 15
<212> TYPE: PRT
<213> ORGANISM: Homo sapiens

<400> SEQUENCE: 142

```
Asp Leu Arg Gly Lys Phe Lys Arg Pro Thr Leu Arg Arg Val Arg
1               5                   10                  15
```

<210> SEQ ID NO 143
<211> LENGTH: 15
<212> TYPE: PRT
<213> ORGANISM: Homo sapiens

<400> SEQUENCE: 143

```
Gly Lys Phe Lys Arg Pro Thr Leu Arg Arg Val Arg Ile Ser Ala
1               5                   10                  15
```

<210> SEQ ID NO 144
<211> LENGTH: 15
<212> TYPE: PRT
<213> ORGANISM: Homo sapiens

<400> SEQUENCE: 144

```
Lys Arg Pro Thr Leu Arg Arg Val Arg Ile Ser Ala Asp Ala Met
1               5                   10                  15
```

<210> SEQ ID NO 145
<211> LENGTH: 15
<212> TYPE: PRT
<213> ORGANISM: Homo sapiens

<400> SEQUENCE: 145

```
Thr Leu Arg Arg Val Arg Ile Ser Ala Asp Ala Met Met Gln Ala
1               5                   10                  15
```

<210> SEQ ID NO 146
<211> LENGTH: 15
<212> TYPE: PRT
<213> ORGANISM: Homo sapiens

<400> SEQUENCE: 146

```
Arg Val Arg Ile Ser Ala Asp Ala Met Met Gln Ala Leu Leu Gly
1               5                   10                  15
```

<210> SEQ ID NO 147
<211> LENGTH: 15
<212> TYPE: PRT
<213> ORGANISM: Homo sapiens

<400> SEQUENCE: 147

```
Ile Ser Ala Asp Ala Met Met Gln Ala Leu Leu Gly Ala Arg Ala
1               5                   10                  15
```

<210> SEQ ID NO 148
<211> LENGTH: 15
<212> TYPE: PRT
<213> ORGANISM: Homo sapiens

<400> SEQUENCE: 148

```
Asp Ala Met Met Gln Ala Leu Leu Gly Ala Arg Ala Lys Glu Ser
1               5                   10                  15
```

<210> SEQ ID NO 149
<211> LENGTH: 15
<212> TYPE: PRT
<213> ORGANISM: Homo sapiens

<400> SEQUENCE: 149

```
Met Gln Ala Leu Leu Gly Ala Arg Ala Lys Glu Ser Leu Asp Leu
1               5                   10                  15
```

<210> SEQ ID NO 150
<211> LENGTH: 15
<212> TYPE: PRT
<213> ORGANISM: Homo sapiens

<400> SEQUENCE: 150

```
Leu Leu Gly Ala Arg Ala Lys Glu Ser Leu Asp Leu Arg Ala His
1               5                   10                  15
```

<210> SEQ ID NO 151
<211> LENGTH: 15
<212> TYPE: PRT
<213> ORGANISM: Homo sapiens

<400> SEQUENCE: 151

```
Ala Arg Ala Lys Glu Ser Leu Asp Leu Arg Ala His Leu Lys Gln
1               5                   10                  15
```

<210> SEQ ID NO 152
<211> LENGTH: 15
<212> TYPE: PRT
<213> ORGANISM: Homo sapiens

<400> SEQUENCE: 152

```
Lys Glu Ser Leu Asp Leu Arg Ala His Leu Lys Gln Val Lys Lys
1               5                   10                  15
```

<210> SEQ ID NO 153
<211> LENGTH: 15
<212> TYPE: PRT
<213> ORGANISM: Homo sapiens

<400> SEQUENCE: 153

```
Leu Asp Leu Arg Ala His Leu Lys Gln Val Lys Lys Glu Asp Thr
1               5                   10                  15
```

```
<210> SEQ ID NO 154
<211> LENGTH: 15
<212> TYPE: PRT
<213> ORGANISM: Homo sapiens

<400> SEQUENCE: 154

Arg Ala His Leu Lys Gln Val Lys Lys Glu Asp Thr Glu Lys Glu
1               5                   10                  15

<210> SEQ ID NO 155
<211> LENGTH: 15
<212> TYPE: PRT
<213> ORGANISM: Homo sapiens

<400> SEQUENCE: 155

Leu Lys Gln Val Lys Lys Glu Asp Thr Glu Lys Glu Asn Arg Glu
1               5                   10                  15

<210> SEQ ID NO 156
<211> LENGTH: 15
<212> TYPE: PRT
<213> ORGANISM: Homo sapiens

<400> SEQUENCE: 156

Val Lys Lys Glu Asp Thr Glu Lys Glu Asn Arg Glu Val Gly Asp
1               5                   10                  15

<210> SEQ ID NO 157
<211> LENGTH: 15
<212> TYPE: PRT
<213> ORGANISM: Homo sapiens

<400> SEQUENCE: 157

Glu Asp Thr Glu Lys Glu Asn Arg Glu Val Gly Asp Trp Arg Lys
1               5                   10                  15

<210> SEQ ID NO 158
<211> LENGTH: 15
<212> TYPE: PRT
<213> ORGANISM: Homo sapiens

<400> SEQUENCE: 158

Glu Lys Glu Asn Arg Glu Val Gly Asp Trp Arg Lys Asn Ile Asp
1               5                   10                  15

<210> SEQ ID NO 159
<211> LENGTH: 15
<212> TYPE: PRT
<213> ORGANISM: Homo sapiens

<400> SEQUENCE: 159

Asn Arg Glu Val Gly Asp Trp Arg Lys Asn Ile Asp Ala Leu Ser
1               5                   10                  15

<210> SEQ ID NO 160
<211> LENGTH: 15
<212> TYPE: PRT
<213> ORGANISM: Homo sapiens

<400> SEQUENCE: 160

Val Gly Asp Trp Arg Lys Asn Ile Asp Ala Leu Ser Gly Met Glu
1               5                   10                  15

<210> SEQ ID NO 161
```

```
<211> LENGTH: 15
<212> TYPE: PRT
<213> ORGANISM: Homo sapiens

<400> SEQUENCE: 161

Trp Arg Lys Asn Ile Asp Ala Leu Ser Gly Met Glu Gly Arg Lys
1               5                   10                  15

<210> SEQ ID NO 162
<211> LENGTH: 15
<212> TYPE: PRT
<213> ORGANISM: Homo sapiens

<400> SEQUENCE: 162

Asn Ile Asp Ala Leu Ser Gly Met Glu Gly Arg Lys Lys Lys Phe
1               5                   10                  15

<210> SEQ ID NO 163
<211> LENGTH: 14
<212> TYPE: PRT
<213> ORGANISM: Homo sapiens

<400> SEQUENCE: 163

Ala Leu Ser Gly Met Glu Gly Arg Lys Lys Lys Phe Glu Ser
1               5                   10
```